US007105617B2

(12) United States Patent
Weck et al.

(10) Patent No.: US 7,105,617 B2
(45) Date of Patent: Sep. 12, 2006

(54) METAL 8-HYDROXYQUINOLINE-FUNCTIONALIZED POLYMERS AND RELATED MATERIALS AND METHODS OF MAKING AND USING THE SAME

(75) Inventors: Marcus Weck, Atlanta, GA (US); Amy Meyers, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 83 days.

(21) Appl. No.: 10/773,980

(22) Filed: Feb. 6, 2004

(65) Prior Publication Data

US 2005/0131175 A1 Jun. 16, 2005

Related U.S. Application Data

(60) Provisional application No. 60/500,000, filed on Sep. 4, 2003, provisional application No. 60/445,701, filed on Feb. 6, 2003.

(51) Int. Cl.
*C08F 4/80* (2006.01)
*C07F 5/06* (2006.01)

(52) U.S. Cl. ............... 526/171; 526/282; 526/308; 526/240; 546/2

(58) Field of Classification Search ............... 526/171, 526/282, 308, 240; 546/2
See application file for complete search history.

(56) References Cited

U.S. PATENT DOCUMENTS

| | | | |
|---|---|---|---|
| 5,141,671 | A | 8/1992 | Bryan et al. |
| 5,719,467 | A | 2/1998 | Antoniadis et al. |
| 6,228,436 | B1 | 5/2001 | Affinito |
| 2002/0028350 | A1 | 3/2002 | Toguchi et al. |
| 2002/0032288 | A1 | 3/2002 | Tanaka et al. |

FOREIGN PATENT DOCUMENTS

| | | |
|---|---|---|
| EP | 0992564 | 4/2000 |
| EP | 1000998 | 5/2000 |
| JP | 09255686 | 3/1997 |
| JP | 09316441 | 12/1997 |
| JP | 10053759 | 2/1998 |
| JP | 2000021573 | 1/2000 |
| JP | 2001284052 | 10/2001 |
| WO | WO 03/044878 | 5/2003 |
| WO | WO 03/048268 | 6/2003 |

OTHER PUBLICATIONS

Burrows et al., Appl. Phys. Lett. 64 (20) (May 15, 1994).*
Meyers et al., Macromolecules 2003, 36, 1766-68.*
Lu et al., Journal of Polymers : Part A : Polymer Chemistry, vol. 38 2887-2892 (2000).*
Meyers et al., Chem Mater. 2004 16 1183-1188.*
Burroughes et al., Nature 347, 539-541 (Oct. 11, 1990).*

Takeshi Tominaga et al., "Luminescent Component", XP002287238, STN Database Accession No. 2001: 778307 Abstract, JP 2001 297881, October 26, 2001, Chemical Abstracts Service, Columbus, Ohio.
Shuji Iwasaki et al., "Zinc Complex and Organic Electroluminescent (EL) Device Using the Complex", XP002287239, STN Database Accession No. 2001: 573264 Abstract, JP 2001 213866, Aug. 7, 2001, Cheamical Abstracts Service, Columbus, Ohio.
Hodaka Tsuge et al., "Organic Electroluminescent Component", XP002287240, STN Database Accession No. 2000: 638398 Abstract, JP 2000 252072, Sep. 14, 2000, Chemical Abstracts Service, Columbus, Ohio.
Takeshi Tominaga et al., "Electroluminescent Component", XP002287241, STN Database Accession No. 2000:274718 Abstract, JP 2000 123972, Apr. 28, 2000, Chemical Abstracts Service, Columbus, Ohio.
Kido, Junji et al., "Orange Color Electroluminescence from Bis (2-styryl-8-Quinolinolato)zinc(II)", Chemistry Letters 1997, The Chemical Society of Japan, 1997.
Zhongmin, Su et al., "Electronic Property and Molecule Design for Luminescent Metal Complexes of Tris(8-Hdyroxquinoline) Gallium", XP009033203 Science in China, Series B: Chemistry, vol. 43, No. 6, Dec. 2000.
Raj, D.S., "Coordination Polymers Based on Bis-Ligand: 1,7-DI(8-Hydroxy-5-Quinolinyl)AZA-1, 3, 5-Heptatriene-3-OL(DHQAHT)", XP009033212, Oriental Journal of Chemistry, vol. 17, No. 3, 2001.
Meyers, Amy et al., "Design and Synthesis of Alq3-Functionalized Polymers", XP002287215, vol. 36, No. 6, American Chemical Society, pp. 1766-1768, 2003.
Duann, Yeh-Fang et al., "The Characteristic of Photoluminescence of tris-(7-Substituted-8-Hydroxyquinoline) Aluminum Complexes and Polymeric Complexes", XP009033202, Applied Organometallic Chemistry, vol. 17, pp. 952-957, 2003.
Meyers, Amy et al., "Solution and Solid-State Characterization of Alq3-Functionalized Polymers", XP002287214, Chemistry of Materials, vol. 16, No. 7, pp. 1183-1188, 2004.

(Continued)

*Primary Examiner*—Robert D. Harlan
(74) *Attorney, Agent, or Firm*—Womble Carlyle Sandridge & Rice, PLLC

(57) ABSTRACT

This invention relates to the synthesis of $Mq_n$-containing monomeric compounds, comprising a polymerizable moiety, an $Mq_n$-moiety, and an optional chemical spacer therebetween, wherein q, in each instance, comprises an 8-hydroxyquinoline residue, M is a metal such as Mg, Zn, Al, Ga, or In, and n is 2 or 3 as the valence of the metal requires. For example, the polymerization of $Znq_2$- or $Alq_3$-containing monomers, in the presence or absence of a co-monomer, provided a $Znq_2$- or $Alq_3$-containing polymer, which retained the optical properties of $Znq_2$ or $Alq_3$ in solution, respectively. The $Mq_n$-containing polymers may be used in, among other things, the fabrication of light-emitting diodes (LEDs).

53 Claims, 11 Drawing Sheets

OTHER PUBLICATIONS

Chemical Journal of Chinese Universities, XP009033211, vol. 21, No. 9, pp. 1416-1421, Sep. 9, 2000.

Chen, C.H. et al., "Metal Chelates as Emitting Materials for Organic Electroluminescence", Coordination Chemistry Reviews 171, pp. 161-174, 1998.

Sheats, James R. et al., "Organic Electroluminescent Devices", Science, New Series, vol. 273, No. 5277, pp. 884-888, Aug. 16, 1996.

Tang, C.W. et al., "Organic Electroluminescent Diodes", Appl. Phys. Lett. 51, pp. 913-915, Sep. 21, 1987.

Tang, C.W. et al., "Electroluminescence of Doped Organic Thin Films", J. Appl. Phys. 85 (9), pp. 3610-3616, May 1, 1989.

Sheats, James R., "Stacked Organic Light-Emitting Diodes in Full Color", Science, New Series, vol. 277, No. 5323, pp. 191-192, Jul. 11, 1997.

Jianping, Lu et al., "Synthesis and Characterization of a Novel AlQ3-Containing Polymer", Journal of Polymer Science: Part A: Polymer Chemistry, vol. 38, pp. 2887-2892, 2000.

Jang, Hyosook et al., "Synthesis and Characterization of New Luminescent Materials Containing Various Substituted 8-Quinolinolate", Synthetic Metals 121, pp. 1667-1668, 2001.

Hopkins, T.A et al., "Substituted Aluminum and Zin Quinolates with Blue-Shifted Absorbance/Luminescence Bands:Synthesis and Spectroscopic, Photoluminescense, and Electroluminescence Characterization", American Chemical Society, vol. 8, pp. 344-351, 1996.

Colle, Michael et al. "Preparation and Characterization of Blue-luminescent Tris(8-hydroxyquinoline) Aluminum (Alq3)", Advanced Functional Materials, vol. 13, No. 2, pp. 108-112, Feb. 2003.

Brinkmann, Martin et al., "Correlation Between Molecular Packing and Optical Properties in Different Crystalline Polymorphs and Amorphous Thin Films of mer-Tris(8-Hydroxyquinoline)Aluminum(III)", American Chemical Society, vol. 122, pp. 5147-5157, 2000.

Braun, M. et al., "A New Crystalline Phase of the Electroluminescent Material Tris(8-hydroxyquinoline) Aluminum Exhibiting Blueshifted Fluorescence", Amerian Institue of Physics, vol. 114, No. 21, pp. 9625-9632, Jun. 1, 2001.

Fischer, Hanns, "The Persistent Radical Effect: A Principle for Selective Radical Reactions and Living Radical Polymerizations", American Chemical Society, vol. 101, pp. 3581-3610, Nov. 7, 2001.

Hawker, Craig J. et al., "New Polymer Synthesis by Nitroxide Mediated Living Radical Polymerizations", American Chemical Society, vol. 101, pp. 3661-3688, Oct. 25, 2001.

Kamigaito, Masami et al., "Metal-Catalyzed Living Radical Polymerization", American Chemical Society, vol. 101, pp. 3689-3745, Dec. 12, 2001.

Buchmeiser, Michael R., "Homogeneous Matathesis Polymerization by Well-Defined Group VI and Group VIII Transition-Metal Alkylidenes: Fundamental and Applications in the Preparation of Advanced Materials", American Chemical Society, vol. 100, pp. 1565-1604, Mar. 16, 2000.

Hawker, Craig J, "Living" Free Radical Polymerization: A Unique Technique for the Preparation of Controlled Macromolecular Architectures, Accounts of Chemical Research, vol. 30, No. 9, pp. 373-382, Mar. 18, 1997.

Sapochak, Linda S. et al, "Electroluminescent Zinc(II) Bis(8-hydroxquinoline): Structural Effects on Electronic States and Device Performance", American Chemical Society, vol. 124, No. 21, pp. 6119-6125, Feb. 5, 2002.

Sapochak, Linda S. et al., "Effects of Systematic Methyl Substitution of Metal (III)Tris(n-Methyl-8-Quinolinolato) Chelates on Material Properties for Optimum Electroluminescence Device Performance", American Chemical Society, vol. 123, No. 26, pp. 6300-6306, Jun. 9, 2001.

Stubbs, Ludger P. et al., "Towards a Unviersal Polymer Backbone: Design and Synthesis of Polymeric Scaffolds Containing Terminal Hydrogen-Bonding Recognition Motifs at Each Repeating Unit", Chemistry A European Journal, vol. 9, No. 4, pp. 992-999, 2003.

* cited by examiner

FIGURE 9

Tungsten-Based Initiators

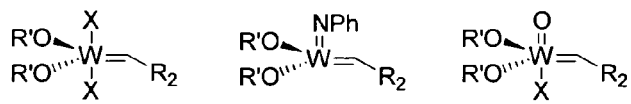

X = Cl, Br, I
R = n-Bu, sec-Bu, t-Bu, Ph, Et, i-Pr
R' = $CH_2$-t-Bu, 2,6-i-$Pr_2$-$C_6H_3$, $CMe(CF_3)_2$,

Molybdenum-Based Initiators

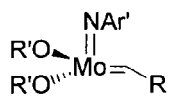

Ar' = phenyl, 2,6-$Me_2$-$C_6H_3$, 2,6-i-$Pr_2$-$C_6H_3$
R = Et, Ph, $CH_3Si$, $CMe_2Ph$, t-Bu, $CMe_3$
R' = $CMe_3$, $CMe_2$-$CF_3$, $CMe(CF_3)_2$, $C(CF_3)_2$, Ar

Ruthenium-Based Initiator

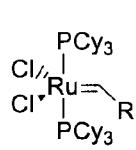 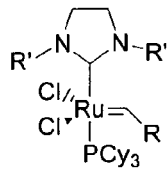 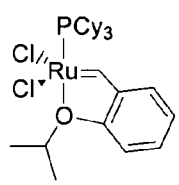 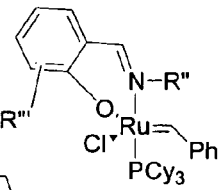

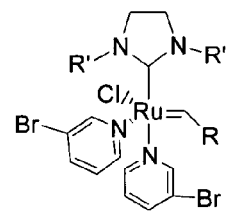

R = Me, Et, Ph, 4-$NO_2$-Ph, 4-$NMe_2$-Ph
4-MePh, 4-MeOPh, 4-ClPh, 4-BrPh

R' = Ms, $CHCH_3Ph$,

R" = 2,6-i-$Pr_2$-$C_6H_3$, 2,6-$Me_2$-4-MeO-$C_6H_3$, 2,6-$Me_2$-4-Br-$C_6H_3$, 2,6-$Cl_2$4-$CF_3C_6H_3$

R''' = H, 4-$NO_2$, 6-Me-4-$NO_3$

METAL 8-HYDROXYQUINOLINE-FUNCTIONALIZED POLYMERS AND RELATED MATERIALS AND METHODS OF MAKING AND USING THE SAME

PRIOR RELATED U.S. APPLICATION DATA

This application claims priority to U.S. patent application Ser. No. 60/445,701, filed Feb. 6, 2003, and U.S. patent application Ser. No. 60/500,000 filed Sep. 4, 2003, each of which is incorporated herein by reference in its entirety.

STATEMENT OF GOVERNMENT LICENSE RIGHTS

The inventors received partial funding support through the Georgia Institute of Technology Molecular Design Institute, under prime contract N00014-95-1-1116 from the Office of Naval Research, and partial funding support through the National Science Foundation through a CAREER award (CHE-0239385). The Federal Government may retain certain license rights in this invention.

TECHNICAL FIELD OF THE INVENTION

This invention relates to the field of electro-optical materials, including organic light-emitting diodes (OLEDs) and the emission and electron-transport layer of OLEDs.

BACKGROUND OF THE INVENTION

Aluminum tris(8-hydroxyquinoline) ($Alq_3$) is a very stable and highly fluorescent solid-state material, which has utility as the emission and electron-transport layer in organic light-emitting diodes (OLEDs). See, for example: Tang, C. W.; VanSlyke, S. A. *Appl. Phys. Lett.* 1987, 51, 913–915; Tang, C. W.; VanSlyke, S. A.; Chen, C. H. *J. Appl. Phys.* 1989, 65, 3610–3616; O'Brien, D. F.; Baldo, M. A.; Thompson, M. E.; Forrest, S. R. *Appl. Phys. Lett.* 1999, 74, 442–444; Kido, J.; Hongawa, K.; Okuyama, K.; Nagai, K. *Appl. Phys. Lett.* 1994, 64, 815–817; Jang, H.; Do, L. -M.; Kim, Y.; Zyung, T.; Do, Y. *Synth. Met.* 2001, 121, 1667–1668, each of which is incorporated herein by reference in its entirety. One of the limitations of using $Alq_3$ in OLEDs is its limited processability. See, for example: Friend, R. H.; Gymer, R. W.; Holmes, A. B.; Burroughes, J. H.; Marks, R. N.; Taliani, C.; Bradley, D. D. C.; Santos, D. A. D.; Bredas, J. L.; Logdlund, M.; Salaneck, W. R. *Nature* 1999, 397, 121–128; Chen, C. H.; Shi, J. *Coord. Chem. Rev.* 1998, 171, 161–174; each of which is incorporated herein by reference in its entirety. Currently, OLEDs are typically fabricated by solution-processing, yet $Alq_3$ must typically be vacuum deposited. What are needed are new compounds, materials, compositions, and methods that can address this limited processability problem such that $Alq_3$ can be more amenable to use in OLEDs.

SUMMARY OF THE INVENTION

As disclosed herein, this invention encompasses the synthesis and utility of a polymer-supported metal-(8-hydroxyquinoline) complexes $Mq_n$ and derivatives and analogs of polymer-supported metal-(8-hydroxyquinoline) complexes $Mq_n$, as well as methods of making and using these materials. In one aspect, for example, M is a metal selected from Mg, Zn, Al, Ga, or In; q is independently selected from 8-hydroxyquinoline or a substituted analog thereof, and n depends upon the stoichiometry required by the metal to form a complex of Mg(II), Zn(II), Al(III), Ga(III), or In(III). Thus, in one aspect, throughout this application, $Mq_n$-containing monomers or polymers are exemplified for complexes of $Alq_3$. Accordingly, $Alq_3$-containing monomers or polymers are disclosed as examples of more general monomers containing $Mgq_2$, $Znq_2$, $Alq_3$, $Gaq_3$, or $Inq_3$; or polymers containing $Mgq_2$, $Znq_2$, $Alq_3$, $Gaq_3$, $Inq_3$, or combinations thereof.

In one aspect, by combining the fluorescent properties of $Mq_n$, such as $Alq_3$, with the processability of a polymer, the present invention can address the limited processability problem of $Alq_3$, while taking advantage of its stability and its fluorescent properties. Because $Alq_3$-functionalized monomers are incorporated into polymers and these $Alq_3$-containing polymers can be used in OLEDs, these materials may potentially be fabricated using low-cost manufacturing techniques such as solution-processing and possibly in ink-jet printing. Further these materials may be used more generally as electro-optical materials for a variety of applications.

In one aspect, the present invention provides a synthesis of an $Mq_n$-containing or $Mq_n$-functionalized compound, including a monomeric compound, wherein the $Mq_n$-functionalized compound comprises a polymerizable moiety and an $Mq_n$-moiety, and wherein q, in each instance, comprises an 8-hydroxyquinoline residue, M is selected from Mg, Zn, Al, Ga, or In, and n is 2 or 3, depending upon the valence of the metal. In this aspect, the $Mq_n$-functionalized compound can further comprise a chemical spacer between the polymerizable moiety and the $Mq_n$-moiety, wherein the chemical spacer comprises between 1 and about 30 carbon atoms.

In one aspect, the polymerizable moiety of the $Mq_n$-functionalized compound, for example an $Alq_3$-functionalized compound, can comprise a cyclic olefin, typically an olefin that is capable of undergoing ring-opening metathesis polymerization (ROMP), although other polymerization methods can also be used. In another aspect, this polymerizable moiety can comprise a strained cyclic olefin. In one aspect, for example, the ROMP of the $Alq_3$-containing compound could be completed within about 12 hours under mild polymerization conditions. In yet another aspect, solubility and other properties of the resulting $Alq_3$-functionalized polymer were tailored by the incorporation of a co-monomer. This method typically provided co-polymers that retained the optical properties of $Alq_3$ in solution. While not intending to be bound by theory, this observation indicated that the polymer coil or backbone of the $Alq_3$-functionalized polymer did not interfere with the luminescence properties of the $Alq_3$ pendant group.

In yet another aspect, the present invention provides a method of making an $Mq_n$-functionalized polymer, comprising: preparing a $q_n$-functionalized monomer; polymerizing the monomer in the presence or absence of a comonomer to form a $q_n$-functionalized polymer; and reacting the polymer with a metal complex to form a $Mq_n$-functionalized polymer.

In another aspect, the present invention provides an $Mq_n$-functionalized compound comprising a polymerizable moiety and an $Mq_n$-moiety, wherein q, in each instance, comprises an 8-hydroxyquinoline residue, M is selected from Mg, Zn, Al, Ga, or In, and n is 2 or 3, depending upon the valence of the metal. In another aspect, this invention provides an $Mq_n$-functionalized polymer comprising the polymerization product of an $Mq_n$-functionalized monomer.

In this aspect, the $Mq_n$-functionalized polymer can comprise the homopolymerization product of an $Mq_n$-functionalized monomer, or the copolymerization product of an $Mq_n$-functionalized monomer and a comonomer. Further, the $Mq_n$-containing monomer can be functionalized with at least one electron-donating group, at least one electron-withdrawing group, or a combination thereof.

In another aspect of this invention, the $Mq_n$-moiety of the monomer or the polymer can be functionalized with at least one electron-donating group, at least one electron-withdrawing group, or a combination thereof. In this aspect, for example, the $Mq_n$-moiety can be functionalized with at least one group independently selected from: a hydrocarbyl group, an oxygen group, a sulfur group, a nitrogen group, a phosphorus group, an arsenic group, a carbon group, a silicon group, a germanium group, a tin group, a lead group, a boron group, an aluminum group, an inorganic group, an organometallic group, or a substituted analog thereof, any one of which having from 1 to about 30 carbon atoms; a halide; hydrogen; or any combination thereof. The inclusion of hydrogen in this list is intended to reflect that the quinoline moiety can optionally be partially saturated.

In another aspect, this invention can encompass a light-emitting diode comprising the polymerization product of the $Mq_n$-functionalized monomer.

Another aspect of this invention is a composition comprising the polymerization product of an $Alq_3$-functionalized monomer, wherein the $Alq_3$-functionalized monomer can comprise a polymerizable moiety and an $Alq_3$-moiety, and wherein q, in each instance, comprises an 8-hydroxyquinoline residue, which, in accordance with this invention, can include a residue of an 8-hydroxyquinoline-like compound, or a functionalized analog of an an 8-hydroxyquinoline or an 8-hydroxyquinoline-like compound. In one aspect, for example, the polymerization product of an $Alq_3$-functionalized monomer is typically substantially non-crosslinked. Also in this aspect, the $Alq_3$-moiety of the $Alq_3$-functionalized monomer can be functionalized with at least one electron-donating group, at least one electron-withdrawing group, or a combination thereof.

In yet another aspect, this invention provides a composition that can comprise the polymerization product of at least one $Alq_3$-functionalized monomer and at least one comonomer, wherein the $Alq_3$-functionalized monomer comprises a polymerizable moiety and an $Alq_3$-moiety, and wherein q, in each instance, comprises an 8-hydroxyquinoline residue, which, in accordance with this invention, can include a residue of an 8-hydroxyquinoline-like compound.

In another aspect, the present invention provides a method of making an $Alq_3$-functionalized polymer, comprising:
polymerizing an $Alq_3$-functionalized monomer in the presence or absence of at least one comonomer;
wherein the $Alq_3$-functionalized monomer comprises a polymerizable moiety and an $Alq_3$-moiety; and
wherein q, in each instance, comprises an 8-hydroxyquinoline residue.

In still another aspect, the present invention provides a method of functionalizing a polymer with an $Alq_3$ moiety, comprising:
providing an $Alq_3$-functionalized monomer; and
polymerizing an $Alq_3$-functionalized monomer in the presence or absence of at least one comonomer;
wherein the $Alq_3$-functionalized monomer comprises a polymerizable moiety and an $Alq_3$-moiety; and
wherein q, in each instance, comprises an 8-hydroxyquinoline residue.

These and other features, aspects, embodiments, and advantages of the present invention will become apparent after a review of the following detailed description of the disclosed features.

BRIEF DESCRIPTION OF THE FIGURES

FIG. 9 provides examples of catalysts that can be used for polymerizing the functionalized monomers to the functionalized polymers, based on a ring-opening metathesis polymerization (ROMP) catalytic process.

DETAILED DESCRIPTION OF THE INVENTION

Figure 1:
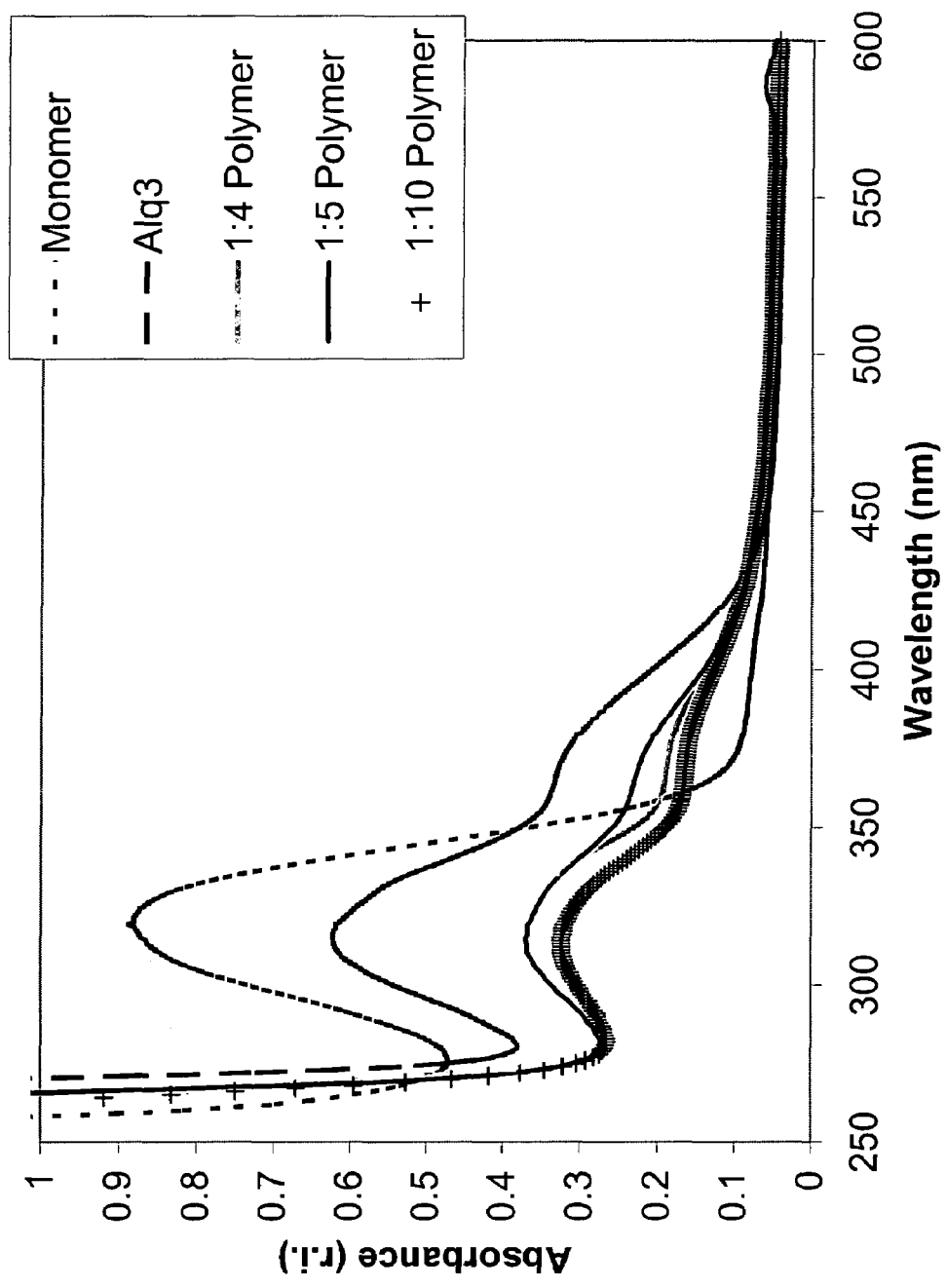
FIG. 1 illustrates the UV/Visible absorption spectra of $Alq_3$, the $Alq_3$-containing monomer 9, and the series of 9:12 copolymers in $CHCl_3$ solution, as described in Table 1.

The present invention addresses some of the current limitations in using $Alq_3$ and related $Mq_n$ compounds in electro-optical materials, including OLEDs, such as its limited processability, by providing a series of $Mq_n$-containing monomers, which comprise a polymerizable moiety and an $Mq_n$-moiety which can be functionalized, and by providing an $Mq_n$-containing polymer comprising the polymerization product of an $Mq_n$-functionalized monomer. Further, the $Mq_n$-containing polymer can comprise the homopolymerization product of an $Mq_n$-functionalized monomer, or the copolymerization product of an $Mq_n$-functionalized monomer and a comonomer, in which the comonomer and the polymerization conditions, including the ratio of comonomer to $Mq_n$-containing monomer, may be used to tailor the properties of the resulting polymer. This invention further encompasses a light-emitting diode comprising a $Mq_n$-functionalized polymer.

Thus, in one aspect, for example, this invention provides $Mq_n$-containing polymers, where the $Mq_n$ complex is embedded within a polymer matrix. In this aspect, the $Mq_n$, such as $Alq_3$, is typically covalently attached to the polymer backbone, which can be accomplished by covalently attaching the $Mq_n$ moiety to the polymerizable monomer, prior to its polymerization. By providing a fully-functionalized monomer that can be polymerized in a controlled fashion, this process substantially eliminates any crosslinking, and hence provides a fully-functionalized polymer without substantial crosslinking. Additionally, the polymer structure can be controlled and altered by using co-monomers to tune the polymeric properties.

Preparation of $Mq_n$-Functionalized Monomers

In one aspect the $Mq_n$-containing monomer typically includes two structural motifs: 1) a polymerizable unit or moiety that provides the required degree of control during the polymerization process; and 2) an $Mq_n$-moiety or residue, which typically comprises Mg(II), Zn(II), Al(III), Ga(III), or In(III) coordinated with two or three, independently selected, 8-hydroxyquinoline-type residues, as disclosed herein. The term 8-hydroxyquinoline residue is used to refer to, among other things, an 8-hydroxyquinoline ligand that can be functionalized with at least one electron-donating group, at least one electron-withdrawing group, or a combination thereof; can be deprotonated; or can be not functionalized; and the like; or any combination of these. This term is also used to refer to 8-hydroxyquinoline-like ligands such as, for example, ligands in which either another heteroatom is present in one of the 6-membered rings of the 8-hydroxyquinoline ligand, or a partially hydrogenated 8-hydroxyquinoline-like ligand. Further, the $Mq_n$-containing monomer typically includes a third, optional, structural motif, namely: 3) an alkyl spacer between the polymerizable unit and the $Mq_n$ to decouple the backbone from the $Mq_n$ group.

In one aspect, norborene could be as the polymerizable unit. Norbornene can be polymerized using ring-opening metathesis polymerization (ROMP), a method that has a high tolerance to many functional groups. See, for example: Fürstner, A. *Angew. Chem. Int. Ed.* 2000, 39, 3012–3043; Piotti, M. E. *Curr. Opin. Solid State Mater. Sci.* 1999, 4, 539–547; Bielawski, C. W.; Grubbs, R. H. *Angew. Chem. Int. Ed.* 2000, 39, 2903–2906; and Sanford, M. S.; Ulman, M.; Grubbs, R. H. *J. Am. Chem. Soc.* 2001, 123, 749–750; each of which is incorporated herein by reference, in its entirety. Furthermore, ROMP is often a living polymerization method resulting in polymers with controlled molecular weights, low polydispersities, and also allows for the formation of block co-polymers. See also, for example: Ivin, K. J. *Olefin Metathesis* Academic Press: London, 1996; Ivin, K. J. and Mol, J. C. *Olefin Metathesis and Metathesis Polymerization* Academic Press: New York, 1997; each of which is incorporated herein by reference, in its entirety.

Scheme 1

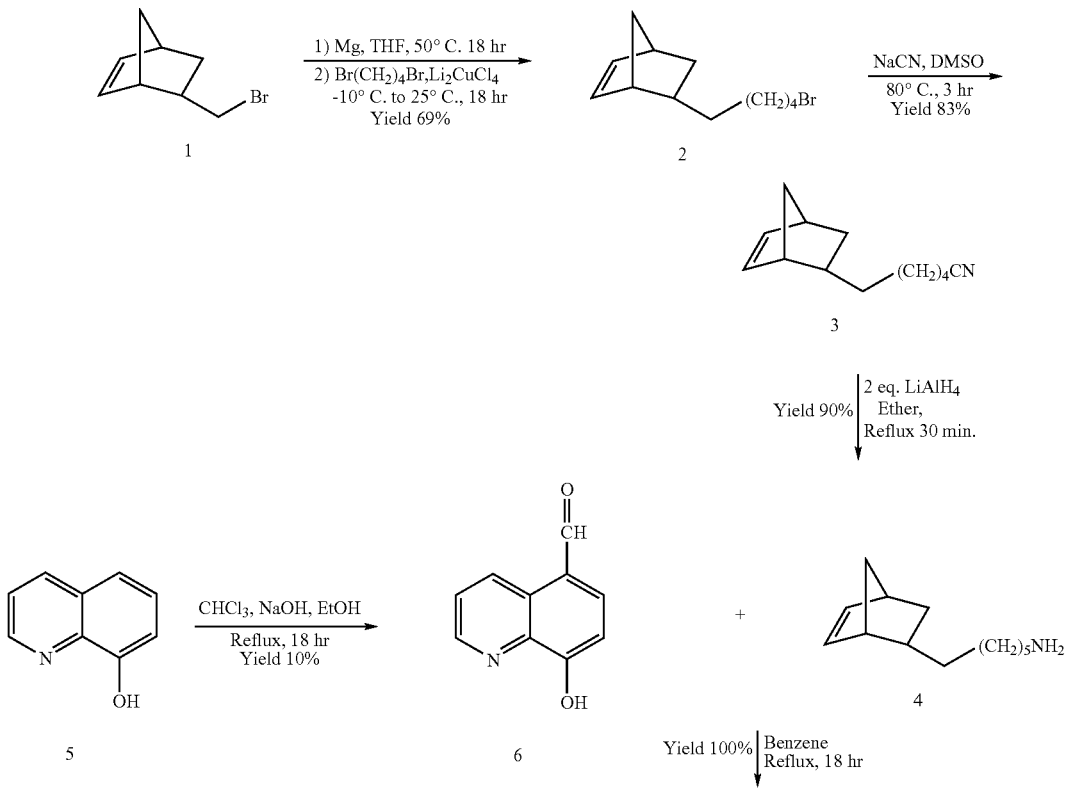

-continued

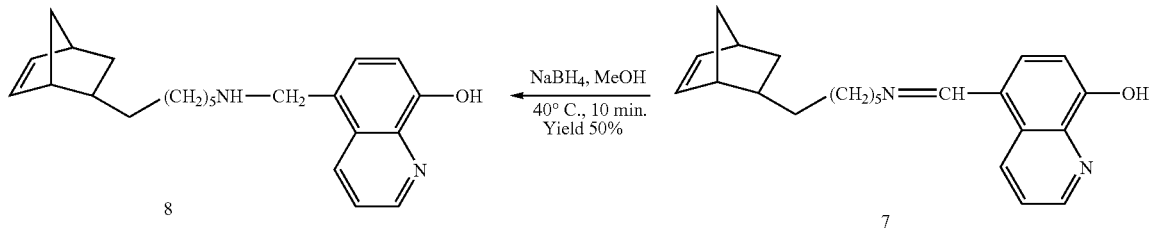

In one aspect, for example, the synthesis of a Mq$_n$-containing monomer encompasses the synthesis of a metal-free monomer as presented in Scheme 1, followed by metallating the monomer. As presented in Scheme 1 and in the Examples, this reaction sequence began with the functionalization of norborene to form bromomethyl norborene 1, formed using a Diels-Alder reaction between allyl bromide and cyclopentadiene. Attachment of a bromoalkyl chain using Grignard chemistry, followed by the conversion of the bromide to the nitrile and subsequent reduction of the nitrile, resulted in the precursor 4 in an overall yield of 51%. Compound 4 was then coupled to 6, itself prepared from compound 5 (8-hydroxyquinoline) as shown, followed by the reduction of the resulting imine to yield monomer 8. (See: Clemo, G. R.; Howe, R. *J. Chem. Soc.* 1955, 3552–3553; which is incorporated herein by reference in its entirety.)

As illustrated in Scheme 2, the formation of the Mq$_n$-functionalized monomer, such as the Alq$_3$-functionalized monomer 9 was achieved, for example, by adding monomer 8 to ten equivalents of triethylaluminum, followed by twenty equivalents of 8-hydroxyquinoline. This reaction resulted in the formation of one equivalent of 9 and nine equivalents of non-functionalized Alq$_3$. In one aspect, this procedure was developed to substantially achieve full metallation of each monomer without coordination of two monomer units onto the same aluminum center, thereby substantially preventing any cross-linking during the polymerization. The statistical probability of having two monomer units attached to the same aluminum center is 0.1%. While this number is negligible and no cross-linking was observed, a very small amount of cross-linking at this point could not be excluded.

Scheme 2

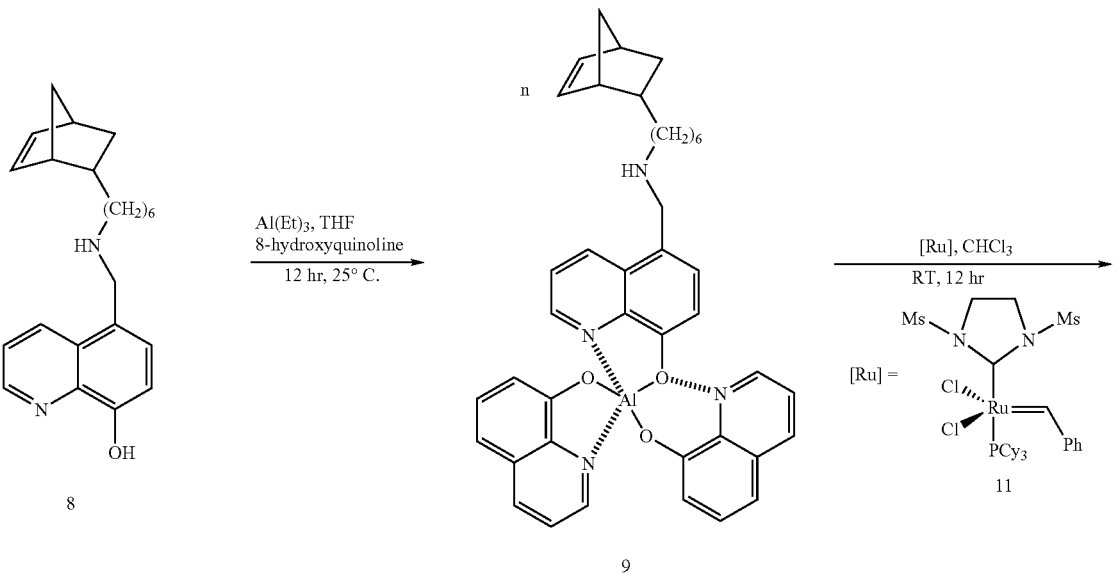

-continued

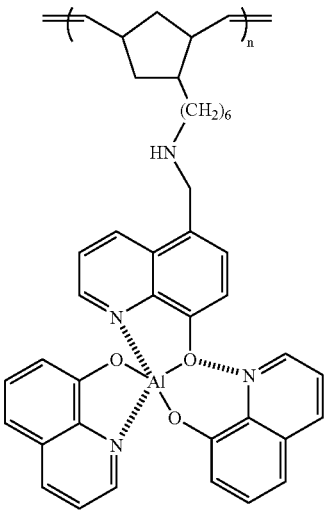

10

Thus, in one aspect, this invention provides an $Mq_n$-functionalized compound comprising a polymerizable moiety and an $Mq_n$-moiety, wherein q, in each instance, comprises an 8-hydroxyquinoline residue, and M is selected from Mg, Zn, Al, Ga, or In; and n is selected from 2 or 3, as the stoichiometry of the complex dictates based upon the valence of the metal.

In another aspect, this invention provides an $Alq_3$-functionalized compound comprising a polymerizable moiety and an $Alq_3$-moiety, wherein q, in each instance, comprises an 8-hydroxyquinoline residue. In this aspect, the $Alq_3$-moiety can be functionalized with at least one electron-donating group, at least one electron-withdrawing group, or a combination thereof, which can be used to tune the optical properties of the $Alq_3$-functionalized compounds, monomers, and polymers. Thus, it is known that the usual blue-green luminescence of $Alq_3$ can be either blue- or red-shifted through the addition of substituents to the 8-hydroxyquinoline residue.

In another aspect, the $Mq_n$-functionalized monomer can further comprise a chemical spacer between the polymerizable moiety and the $Mq_n$-moiety, and the chemical spacer can optionally be functionalized with at least one electron-donating group, at least one electron-withdrawing group, or a combination thereof. Thus, in one aspect, the chemical spacer comprises an alkyl linkage or spacer group, having between 1 and about 30 carbon atoms. In another aspect, the chemical spacer comprises an alkyl linkage or spacer group, having greater than or equal to about 4 carbon atoms. While not intending to be bound by theory, it is believed that this spacer was employed to assist in decoupling the motion of the backbone from the pendant $Mq_n$-group.

Also in this aspect, for example, the $Mq_n$-moiety can be functionalized with at least one group independently selected from: a hydrocarbyl group, an oxygen group, a sulfur group, a nitrogen group, a phosphorus group, an arsenic group, a carbon group, a silicon group, a germanium group, a tin group, a lead group, a boron group, an aluminum group, an inorganic group, an organometallic group, or a substituted analog thereof, any one of which having from 1 to about 30 carbon atoms; a halide; hydrogen; or any combination thereof, as long as these groups do not terminate the fluorescent properties of the resulting monomer and the resulting polymer. This list of possible substitutents includes hydrogen, therefore the notion of a partially saturated analog or derivative of 8-hydroxyquinoline is encompassed by this invention. Further the substituents are independently selected, therefore, examples of these groups are provided below which are selected in each instance they appear in the functionalized $Alq_3$-moiety, as long as these groups do not terminate the fluorescent properties of the resulting monomer and the resulting polymer.

Examples of each of these substituent groups include, but are not limited to, the following groups. In each example presented below, unless otherwise specified, R is independently selected from a hydrocarbyl group, including, but not limited to, an aliphatic group; an aromatic group; a cyclic group; any combination thereof; any substituted derivative thereof, including but not limited to, a halide-, an alkoxide-, or an amide-substituted derivative thereof, any one of which has from 1 to about 30 carbon atoms; or hydrogen. Also included in these groups are any unsubstituted, branched, or linear analogs thereof.

Examples of hydrocarbyl groups include aliphatic groups which, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and linear analogs or derivatives thereof, in each instance having from one to about 30 carbon atoms. Thus, aliphatic groups include, but are not limited to, hydrocarbyls such as paraffins and alkenyls. For example, aliphatic groups as used herein include methyl, ethyl, propyl, n-butyl, tert-butyl, sec-butyl, isobutyl, amyl, isoamyl, hexyl, cyclohexyl, heptyl, octyl, nonyl, decyl, dodecyl, 2-ethylhexyl, pentenyl, butenyl, and the like.

Examples of hydrocarbyl groups also include aromatic groups which, in each instance, include, but are not limited to, phenyl, naphthyl, anthracenyl, and the like, including substituted derivatives thereof, in each instance having from 6 to about 30 carbons. Substituted derivatives of aromatic compounds include, but are not limited to, tolyl, xylyl, mesityl, and the like, including any heteroatom substituted derivative thereof.

Examples of hydrocarbyl groups further include cyclic organic groups which, in each instance, include, but are not limited to, cycloparaffins, cycloolefins, cycloacetylenes, arenes such as phenyl, bicyclic groups and the like, including substituted derivatives thereof, in each instance having from about 3 to about 30 carbon atoms. Thus heteroatom-substituted cyclic groups such as furanyl are included herein.

In each instance, hydrocarbyl groups further include groups that contain both aliphatic and cyclic portions, examples of which include, but are not limited to, groups such as: —$(CH_2)_m C_6 H_q R_{5-q}$ wherein m is an integer from 1 to about 10, q is an integer from 1 to 5, inclusive; $(CH_2)_m C_6 H_q R_{10-q}$ wherein m is an integer from 1 to about 10, q is an integer from 1 to 10, inclusive; and $(CH_2)_m C_5 H_q R_{9-q}$ wherein m is an integer from 1 to about 10, q is an integer from 1 to 9, inclusive. In each instance and as defined above, R is independently selected from: an aliphatic group; an aromatic group; a cyclic group; any combination thereof, any substituted derivative thereof, including but not limited to, a halide-, an alkoxide-, or an amide-substituted derivative thereof; any one of which has from 1 to about 30 carbon atoms; or hydrogen. In one aspect, aliphatic and cyclic groups include, but are not limited to: —$CH_2C_6H_5$; —$CH_2C_6H_4F$; —$CH_2C_6H_4Cl$; —$CH_2C_6H_4Br$; —$CH_2C_6H_4I$; —$CH_2C_6H_4OMe$; —$CH_2C_6H_4OEt$; —$CH_2C_6H_4NH_2$; —$CH_2C_6H_4NMe_2$; —$CH_2C_6H_4NEt_2$; —$CH_2CH_2C_6H_5$; —$CH_2CH_2C_6H_4F$; —$CH_2CH_2C_6H_4Cl$; —$CH_2CH_2C_6H_4Br$; —$CH_2CH_2C_6H_4I$; —$CH_2CH_2C_6H_4OMe$; —$CH_2CH_2C_6H_4OEt$; —$CH_2CH_2C_6H_4NH_2$; —$CH_2CH_2C_6H_4NMe_2$; —$CH_2CH_2C_6H_4NEt_2$; any regioisomer thereof, and any substituted derivative thereof.

Examples of halides, in each instance, include fluoride, chloride, bromide, and iodide.

In each instance, oxygen groups are oxygen-containing groups, examples of which include, but are not limited to, alkoxy or aryloxy groups (—OR), —OC(O)R, —OC(O)H, —$OSiR_3$, —$OPR_2$, —$OAlR_2$, and the like, including substituted derivatives thereof, wherein R in each instance is selected from alkyl, cycloalkyl, aryl, aralkyl, substituted alkyl, substituted aryl, or substituted aralkyl having from 1 to about 30 carbon atoms. Examples of alkoxy or aryloxy groups (—OR) groups include, but are not limited to, methoxy, ethoxy, propoxy, butoxy, phenoxy, substituted phenoxy, and the like.

In each instance, sulfur groups are sulfur-containing groups, examples of which include, but are not limited to, —SR, —$OSO_2R$, —$OSO_2OR$, —SCN, —$SO_2R$, and the like, including substituted derivatives thereof, wherein R in each instance is selected from alkyl, cycloalkyl, aryl, aralkyl, substituted alkyl, substituted aryl, or substituted aralkyl having from 1 to about 30 carbon atoms.

In each instance, nitrogen groups are nitrogen-containing groups, which include, but are not limited to, —$NH_2$, —NHR, —$NR_2$, —$NO_2$, —$N_3$, and the like, including substituted derivatives thereof, wherein R in each instance is selected from alkyl, cycloalkyl, aryl, aralkyl, substituted alkyl, substituted aryl, or substituted aralkyl having from 1 to about 30 carbon atoms.

In each instance, phosphorus groups are phosphorus-containing groups, which include, but are not limited to, —$PH_2$, —PHR, —$PR_2$, —$P(O)R_2$, —$P(OR)_2$, —$P(O)(OR)_2$, and the like, including substituted derivatives thereof, wherein R in each instance is selected from alkyl, cycloalkyl, aryl, aralkyl, substituted alkyl, substituted aryl, or substituted aralkyl having from 1 to about 30 carbon atoms.

In each instance, arsenic groups are arsenic-containing groups, which include, but are not limited to, —AsHR, —$AsR_2$, —$As(O)R_2$, —$As(OR)_2$, —$As(O)(OR)_2$, and the like, including substituted derivatives thereof, wherein R in each instance is selected from alkyl, cycloalkyl, aryl, aralkyl, substituted alkyl, substituted aryl, or substituted aralkyl having from 1 to about 30 carbon atoms.

In each instance, carbon groups are carbon-containing groups, which include, but are not limited to, alkyl halide groups that comprise halide-substituted alkyl groups with 1 to about 30 carbon atoms, aralkyl groups with 1 to about 30 carbon atoms, —C(O)H, —C(O)R, —C(O)OR, cyano, —C(NR)H, —C(NR)R, —C(NR)OR, and the like, including substituted derivatives thereof, wherein R in each instance is selected from alkyl, cycloalkyl, aryl, aralkyl, substituted alkyl, substituted aryl, or substituted aralkyl having from 1 to about 30 carbon atoms.

In each instance, silicon groups are silicon-containing groups, which include, but are not limited to, silyl groups such alkylsilyl groups, arylsilyl groups, arylalkylsilyl groups, siloxy groups, and the like, which in each instance have from 1 to about 30 carbon atoms. For example, silicon groups include trimethylsilyl and phenyloctylsilyl groups.

In each instance, germanium groups are germanium-containing groups, which include, but are not limited to, germyl groups such alkylgermyl groups, arylgermyl groups, arylalkylgermyl groups, germyloxy groups, and the like, which in each instance have from 1 to about 30 carbon atoms.

In each instance, tin groups are tin-containing groups, which include, but are not limited to, stannyl groups such alkylstannyl groups, arylstannyl groups, arylalkylstannyl groups, stannoxy groups, and the like, which in each instance have from 1 to about 30 carbon atoms. Thus, tin groups include, but are not limited to, stannoxy groups.

In each instance, lead groups are lead-containing groups, which include, but are not limited to, alkyllead groups, aryllead groups, arylalkyllead groups, and the like, which in each instance, have from 1 to about 30 carbon atoms.

In each instance, boron groups are boron-containing groups, which include, but are not limited to, —$BR_2$, —$BX_2$, —BRX, wherein X is a monoanionic group such as halide, hydride, alkoxide, alkyl thiolate, and the like, and wherein R in each instance is selected from alkyl, cycloalkyl, aryl, aralkyl, substituted alkyl, substituted aryl, or substituted aralkyl having from 1 to about 30 carbon atoms.

In each instance, aluminum groups are aluminum-containing groups, which include, but are not limited to, —$AlR_2$, —$AlX_2$, —AlRX, wherein X is a monoanionic group such as halide, hydride, alkoxide, alkyl thiolate, and the like, and wherein R in each instance is selected from alkyl, cycloalkyl, aryl, aralkyl, substituted alkyl, substituted aryl, or substituted aralkyl having from 1 to about 30 carbon atoms.

Examples of inorganic groups that may be used as substituents for substituted cyclopentadienyls, substituted indenyls, substituted fluorenyls, and substituted boratabenzenes, in each instance, include, but are not limited to, —$SO_2X$, —$OAlX_2$, —$OSiX_3$, —$OPX_2$, —SX, —$OSO_2X$, —$AsX_2$, —$As(O)X_2$, —$PX_2$, and the like, wherein X is a monoanionic group such as halide, hydride, amide, alkoxide, alkyl thiolate, and the like, and wherein any alkyl, cycloalkyl, aryl, aralkyl, substituted alkyl, substituted aryl, or substituted aralkyl group or substituent on these ligands has from 1 to about 30 carbon atoms.

Examples of organometallic groups that may be used as substituents for substituted cyclopentadienyls, substituted indenyls, and substituted fluorenyls, in each instance, include, but are not limited to, organoboron groups, organoaluminum groups, organogallium groups, organosilicon groups, organogermanium groups, organotin groups, organolead groups, organo-transition metal groups, and the like, having from 1 to about 30 carbon atoms.

In another aspect, this invention provides an $Mq_n$-functionalized compound comprising a polymerizable moiety and an $Mq_n$-moiety, wherein q, in each instance. comprises an 8-hydroxyquinoline residue, and M is selected from Mg, Zn, Al, Ga, or In; and n is selected from 2 or 3, depending upon the valence of the metal. The $Mq_n$-moiety can be functionalized with at least one electron-donating group, at least one electron-withdrawing group, or a combination thereof. In yet another aspect, $Mq_n$-moiety can be functionalized with at least one group independently selected from: a hydrocarbyl group, an oxygen group, a sulfur group, a nitrogen group, a phosphorus group, an arsenic group, a carbon group, a silicon group, a germanium group, a tin group, a lead group, a boron group, an aluminum group, an inorganic group, an organometallic group, or a substituted analog thereof, any one of which having from 1 to about 30 carbon atoms; a halide; hydrogen; or any combination thereof.

In still another aspect, this invention provides an $Mq_n$-functionalized compound comprising a polymerizable moiety and an $Mq_n$-moiety, wherein q, in each instance, comprises an 8-hydroxyquinoline residue, and M is selected from Mg, Zn, Al, Ga, or In; and n is selected from 2 or 3 according to the valence of the metal, wherein the compound has the formula

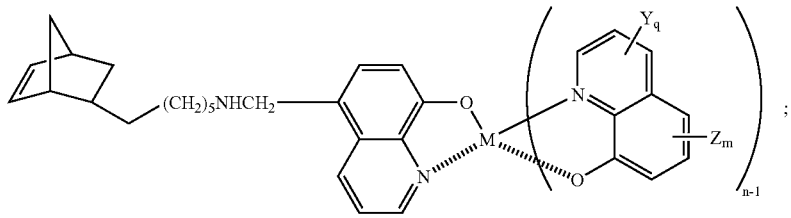

wherein Y and Z are independently selected from —F, —Cl, —Br, —I, —$R^1$, —$CR^1$=O, —CH=CHC(O)$R^1$, —C(O)$R^1$, —C(O)O$R^1$, —CN, —C(N$R^1$)$R^1$, —C(N$R^1$)O$R^1$, —CH$_2$C$_6$H$_4$X, —CH$_2$C$_6$H$_3$X$_2$, —CH$_2$C$_6$H$_4$$R^1$, —CH$_2$C$_6$H$_3$$R_2^1$, —CH$_2$CH$_2$C$_6$H$_4$X, —CH$_2$CH$_2$C$_6$H$_3$X$_2$, CH$_2$CH$_2$C$_6$H$_4$$R^1$, —CH$_2$CH$_2$C$_6$H$_3$$R_2^1$, —CH=C$R_2^1$, —C≡C$R^1$, —O$R^1$, —OC(O)$R^1$, —Si$R_3^1$, —OSi$R_3^1$, —NO$_2$, —N$R_2^1$, —N$_3$, —N=C$R_2^1$, —N=N$R^1$, —S$R^1$, —SX, —OSO$_2$$R^1$, —OSO$_2$O$R^1$, —SCN, —SO$_2$$R^1$, —P$R_2^1$, —PX$_2$, —P(O)$R_2^1$, —P(O$R^1$)$_2$, —P(O)(O$R^1$)$_2$, —OSi$R_3^1$, —OP$R_2^1$, —OAl$R_2^1$, —As$R_2^1$, —As(O)$R_2^1$, —As(O$R^1$)$_2$, —As(O)(O$R^1$)$_2$, Sn$R_3$, OSn$R_3^1$, SnX$_3^1$, OSnX$_3^1$, —B$R_2^1$, —BX$_2$, —B$R^1$X, —SO$_2$X, —OAlX$_2$, —OSiX$_3$, —OPX$_2$, —OSO$_2$X, —AsX$_2$, or —As(O)X$_2$;

wherein $R^1$, in each instance, is independently selected from H or a substituted or unsubstituted hydrocarbyl group having from 1 to about 30 carbon atoms;

wherein X, in each instance, is independently selected from F, Cl, Br, I, H, O$R^1$, —S$R^1$, or N$R_2^1$; and wherein q and m are independently selected from an integer from 0 to 3.

The present invention further encompasses a method of making a $Mq_n$-functionalized polymer, comprising:
preparing a $q_n$-functionalized monomer;
polymerizing the monomer in the presence or absence of a comonomer to form a $q_n$-functionalized polymer; and
reacting the polymer with a metal complex to form a $Mq_n$-functionalized polymer;
wherein M is selected from Mg, Zn, Al, Ga, or In; and n is selected from 2 or 3, depending upon the valence of the metal. In another aspect, M is selected from Zn or Al.

In another aspect, this invention provides an $Alq_3$-functionalized compound wherein the compound has the following formula:

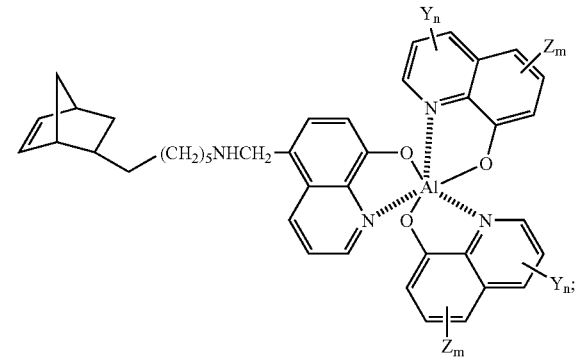

wherein Y and Z are independently selected from —F, —Cl, —Br, —I, —$R^1$, —$CR^1$=O, —CH=CHC(O)$R^1$, —C(O)$R^1$, —C(O)O$R^1$, —CN, —C(N$R^1$)$R^1$, —C(N$R^1$)O$R^1$, —CH$_2$C$_6$H$_4$X, —CH$_2$C$_6$H$_3$X$_2$, —CH$_2$C$_6$H$_4$$R^1$, —CH$_2$C$_6$H$_3$$R_2^1$, —CH$_2$CH$_2$C$_6$H$_4$X, —CH$_2$CH$_2$C$_6$H$_3$X$_2$, CH$_2$CH$_2$C$_6$H$_4$$R^1$, —CH$_2$CH$_2$C$_6$H$_3$$R_2^1$, —CH=C$R_2^1$, —C≡C$R^1$, —O$R^1$, —OC(O)$R^1$, —Si$R_3^1$, —OSi$R_3^1$, —NO$_2$, —N$R_2^1$, —N$_3$, —N=C$R_2^1$, —N=N$R^1$, —S$R^1$, —SX, —OSO$_2$$R^1$, —OSO$_2$O$R^1$, —SCN, —SO$_2$$R^1$, —P$R_2^1$, —PX$_2$, —P(O)$R_2^1$, —P(O$R^1$)$_2$, —P(O)(O$R^1$)$_2$, —OSi$R_3^1$, —OP$R_2^1$, —OAl$R_2^1$, —As$R_2^1$, —As(O)$R_2^1$, —As(O$R^1$)$_2$, —As(O)(O$R^1$)$_2$, Sn$R_3$, OSn$R_3^1$, SnX$_3^1$, OSnX$_3^1$, —B$R_2^1$, —BX$_2$, —B$R^1$X, —SO$_2$X, —OAlX$_2$, —OSiX$_3$, —OPX$_2$, —OSO$_2$X, —ASX$_2$, or —AS(O)X$_2$;

wherein $R^1$, in each instance, is independently selected from H or a substituted or unsubstituted hydrocarbyl group having from 1 to about 30 carbon atoms;

wherein X, in each instance, is independently selected from F, Cl, Br, I, H, O$R^1$, —S$R^1$, or N$R_2^1$; and wherein n and m are independently selected from an integer from 0 to 3. Thus, this list of possible substitutents includes hydrogen, therefore the notion of a partially saturated analog or derivative of 8-hydroxyquinoline is encompassed by this invention.

In yet another aspect, the present invention provides an Alq$_3$-functionalized compound including, but not limited to:

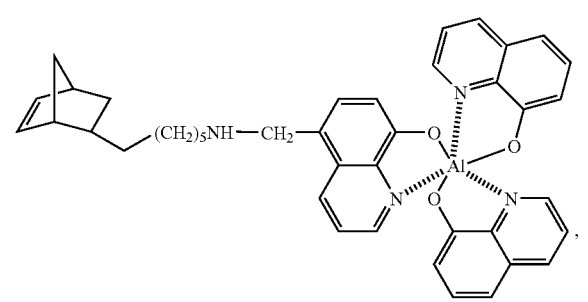

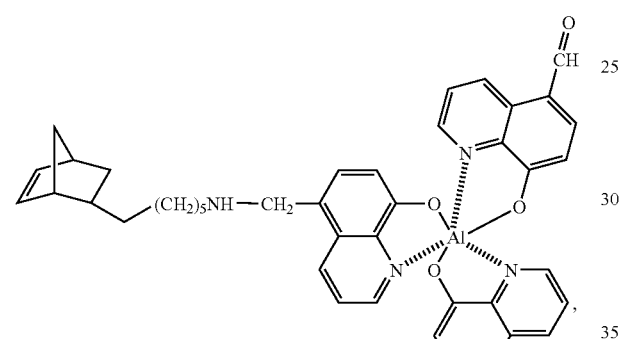

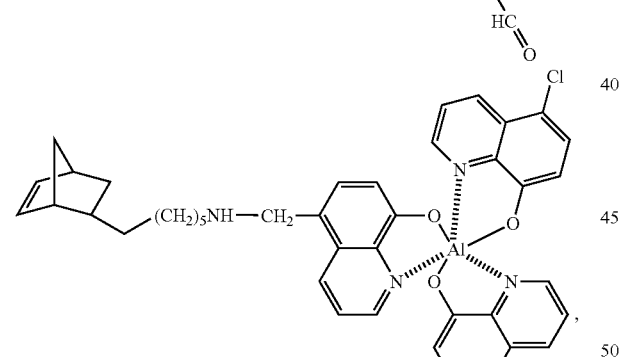

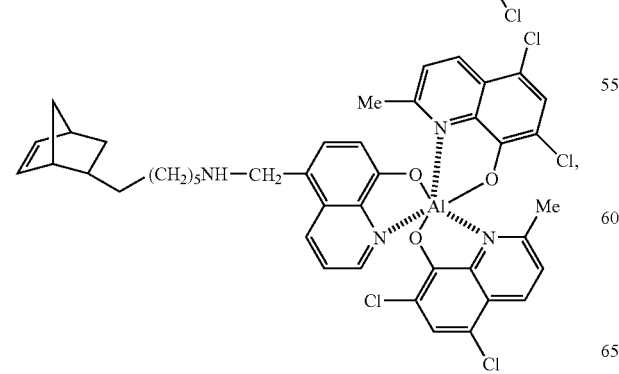

-continued

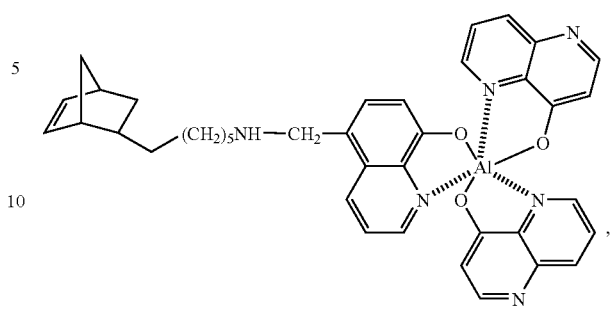

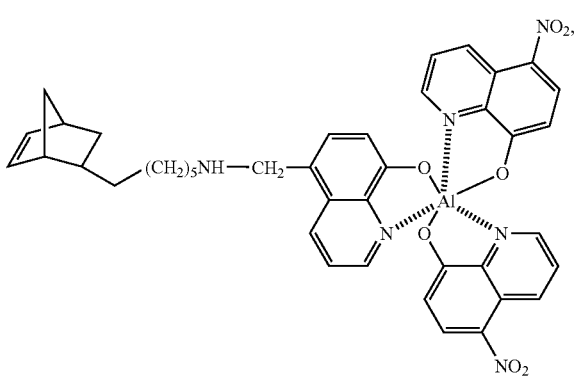

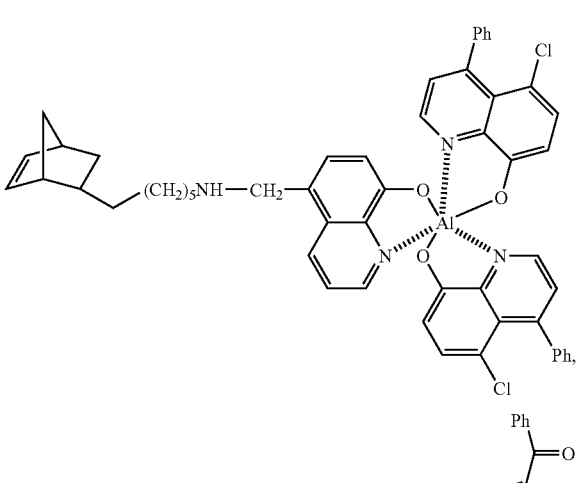

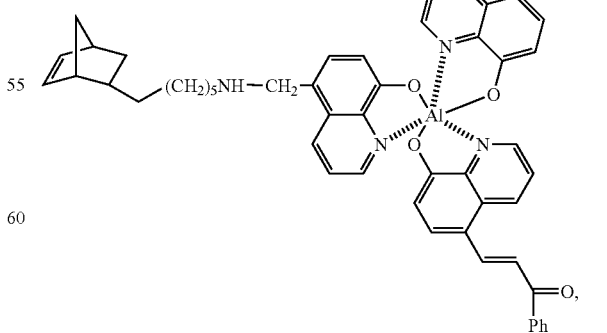

-continued

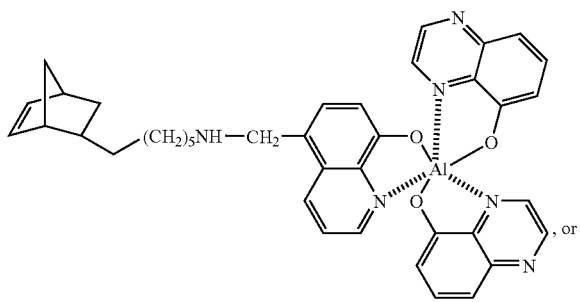

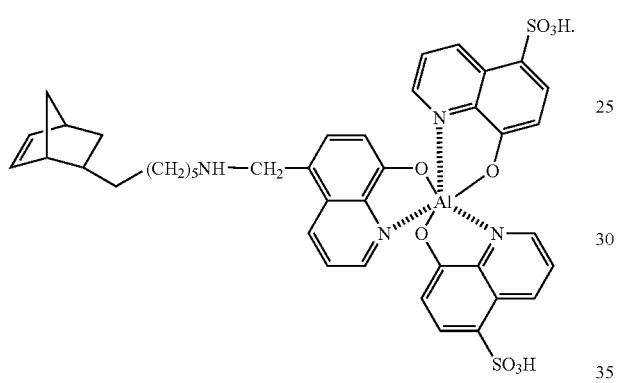

In yet another aspect, the present invention provides an Mq$_n$-functionalized compound comprising a polymerizable moiety and an Mq$_n$-moiety, wherein the polymerizable moiety comprises norbornene, norbornadiene, cyclopentene, cyclooctene, cyclooctadiene, or a functionalized analog thereof. In yet another aspect, the polymerizable moiety comprises norborene.

In still another aspect, the present invention provides an Mq$_n$-functionalized compound comprising a polymerizable moiety and an Mq$_n$-moiety, which further comprises a chemical spacer between the polymerizable moiety and the Mq$_n$-moiety, having between 1 and about 30 carbon atoms. In this aspect, for example, the chemical spacer is selected from —(CH$_2$)$_n$NR$^1$CH$_2$—, wherein n in the formula of the spacer is from 1 to about 12, and R$^1$ is selected from H or a hydrocarbyl or substituted hydrocarbyl having from 1 to about 30 carbon atoms. Thus, the chemical spacer can be —(CH$_2$)$_n$NHCH$_2$—.

In still another aspect, this invention provides a light-emitting diode comprising the polymerization product of any Mq$_n$-functionalized compound disclosed herein.

Preparation of Mq$_n$-Functionalized Homo- and CoPolymers

The formation of the Alq$_3$-functionalized monomer 9 was achieved, for example, by adding monomer 8 to ten equivalents of triethylaluminum, followed by twenty equivalents of 8-hydroxyquinoline, as illustrated in Scheme 2 and in the Examples provided herein. This reaction resulted in the formation of one equivalent of 9 and nine equivalents of non-functionalized Alq$_3$. This 9:1 mixture (Alq$_3$:9) could be used directly in the polymerizations, which were carried out in chloroform at room temperature using the ruthenium catalyst 11. Under these conditions, a 50:1 monomer to catalyst ratio was fully polymerized to polymer 10 within 12 hours. After complete polymerization, the excess Alq$_3$ was removed from the polymer through extensive washings with methanol and methylene chloride, yielding a polymer without any impurities. The formation of the Znq$_2$-functionalized monomer was achieved similarly, using ZnEt$_2$ in place of AlEt$_3$ in Scheme 2.

The formation of the other Mq$_n$-functionalized monomers, wherein Mq$_n$ is selected from Mgq$_2$, Gaq$_3$, or Inq$_3$, may be achieved in a similar manner as that disclosed in Scheme 2, for example, by adding monomer 8 to an excess (about 10 equivalents) of metal halides, including, but not limited to, MgCl$_2$, GaCl$_3$, or InCl$_3$, respectively, followed by an excess (about twenty equivalents) of 8-hydroxyquinoline. Other halides such as bromides and iodides may be used as well. These Mq$_n$-functionalized monomers may then be polymerized as indicated in Scheme 2.

Scheme 3

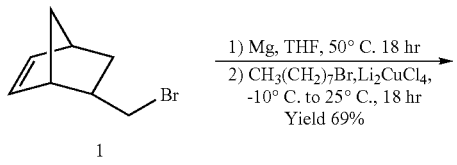

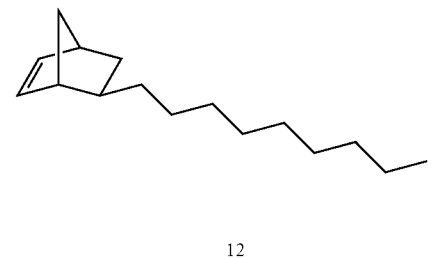

Solubility of the Alq$_3$-functionalized homopolymer proved to be limited, and redissolving the polymer proved to be difficult, possibly due to the highly charged character of the polymer. However, solubility of the Alq$_3$-functionalized polymer could be increased by co-polymerizing 9 with 5-nonylnorbornene 12, a non-functionalized monomer, which was synthesized as shown in Scheme 3, and presented in the Examples.

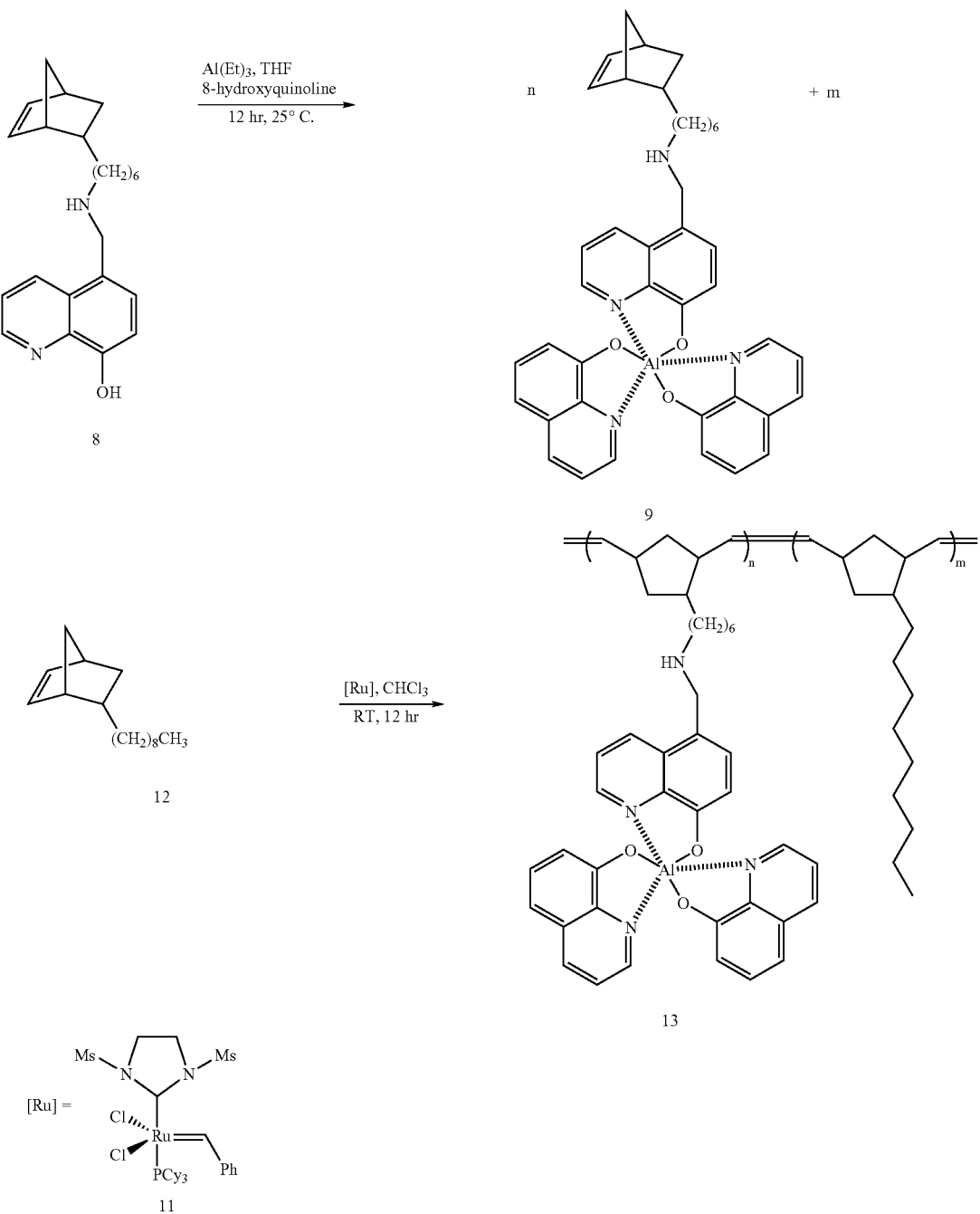

Scheme 4

Using comonomers such as compound 12, Alq$_3$-functionalized copolymers could be prepared according to Scheme 4. Znq$_2$-functionalized copolymers could be prepared similarly, according to Scheme 4. The other Mq$_n$-functionalized copolymers can also be polymerized as indicated in Scheme 4 for the Alq$_3$ system. Thus, in this aspect, solubility of the Alq$_3$-functionalized copolymer exceeded that of the Alq$_3$-functionalized homopolymer. However, in one aspect, this invention provides for the formation of an Alq$_3$-functionalized homopolymer and further provides for the formation of an Alq$_3$-functionalized copolymer, wherein the molar ratio of the functional monomer to spacer monomer is from about 1,000:1 to about 1:1,000. In another aspect, the molar ratio of the functional monomer to spacer monomer is from about 1:1 to about 1:100, and in another aspect, from about 1:3 to about 1:20. In yet another aspect, the molar ratio of the functional monomer to spacer monomer is from about 1:4 to about 1:10.

In another aspect, the molar ratio of functional monomer to spacer monomer (9:12) was examined to determine ratios wherein 9 can be incorporated in a relatively high percentage, while retaining a useful measure of solubility. This ratio was investigated through the synthesis of a series of co-polymers, as illustrated in Table 1. All co-polymers with a 9:12 ratio of at least about 1:1 could be fully solubilized in a 0.1% (v/v) chloroform/trifluoroacetic acid mixture. All resolubilized co-polymers were characterized using gel-permeation chromatography and showed polydispersities from about 1.5 to about 1.8. Differential scanning calorimetry did not show a glass-transition temperature or a melting temperature for these copolymers, while thermogravimetric analysis showed the onset of polymer decomposition at 250° C.

TABLE 1

Absorption and Photoluminescence data for 8, Alq$_3$, and a series of co-polymers; and co-polymer characterization data for 9:12) polymers.

| Sample | UV/Vis conc. (mg/mL) | UV/Vis $\lambda_{max}$ (nm) | Fluorescence conc. (mg/mL) | Fluorescence $\lambda_{max}$ (nm) [Intensity] | Mn | Mw | PDI |
|---|---|---|---|---|---|---|---|
| Monomer 8 | 0.02 | 319 | — | — | — | — | — |
| Alq$_3$ | 0.1 | 316, 372 | 0.09 | 509 | — | — | — |
| 1:4 (9:12) Polymer | 0.5 | 313, 370 | 0.05 | 512 [2633836] | 68000 | 104000 | 1.53 |
| 1:5 (9:12) Polymer | 0.5 | 313, 371 | 0.05 | 509 [2364129] | 55000 | 94000 | 1.71 |
| 1:10 (9:12) Polymer | 0.5 | 313, 373 | 0.05 | 506 [1727476] | 57000 | 100000 | 1.74 |

In one aspect, this invention provides a composition comprising the polymerization product of an Mq$_n$-functionalized monomer, wherein the Mq$_n$-functionalized monomer comprises a polymerizable moiety and an Mq$_n$-moiety, wherein q, in each instance, comprises an 8-hydroxyquinoline residue; M is selected from Mg, Zn, Al, Ga, or In; and n is selected from 2 or 3 according to the valence of the metal. In another aspect, this polymerization product can be substantially non-crosslinked. Further, and in another aspect, the Mq$_n$-moiety can be functionalized with at least one electron-donating group, at least one electron-withdrawing group, or a combination thereof. In another aspect, the polymerizable moiety can comprise norborene. This invention further provides a light-emitting diode comprising the polymerization product of an Mq$_n$-functionalized monomer, wherein the Mq$_n$-functionalized monomer comprises a polymerizable moiety and an Mq$_n$-moiety, wherein q, in each instance, comprises an 8-hydroxyquinoline residue; M is selected from Mg, Zn, Al, Ga, or In; and n is selected from 2 or 3.

In yet another aspect of this invention, this invention provides a composition comprising the polymerization product of at least one Mq$_n$-functionalized monomer and at least one comonomer, wherein the Mq$_n$-functionalized monomer comprises a polymerizable moiety and an Mq$_n$-moiety; wherein q, in each instance, comprises an 8-hydroxyquinoline residue; M is selected from Mg, Zn, Al, Ga, or In; and n is selected from 2 or 3 according to the valence of the metal. In another aspect, the polymerizable moiety can comprise norborene, norbornadiene, cyclopentene, cyclooctene, cyclooctadiene, or a substituted analog thereof. In yet another aspect, the polymerizable moiety can comprise norborene or a substituted analog thereof.

In yet another aspect, this invention provides a composition comprising the polymerization product of at least one Mq$_n$-functionalized monomer and at least one comonomer, wherein the Mq$_n$-functionalized monomer comprises a polymerizable moiety and an Mq$_n$-moiety, and wherein the Mq$_n$-moiety can be functionalized with at least one electron-donating group, at least one electron-withdrawing group, or a combination thereof. In another aspect, the Mq$_n$-moiety can be functionalized with at least one group independently selected from: a hydrocarbyl group, an oxygen group, a sulfur group, a nitrogen group, a phosphorus group, an arsenic group, a carbon group, a silicon group, a germanium group, a tin group, a lead group, a boron group, an aluminum group, an inorganic group, an organometallic group, or a substituted analog thereof, any one of which having from 1 to about 30 carbon atoms; a halide; hydrogen; or any combination thereof.

In a further aspect of this invention, the Mq$_n$-moiety can be functionalized with at least one group independently selected from —F, —Cl, —Br, —I, —R$^1$, —CR$^1$═O, —CH═CHC(O)R$^1$, —C(O)R$^1$, —C(O)OR$^1$, —CN, —C(NR$^1$)R$^1$, —C(NR$^1$)OR$^1$, —CH$_2$C$_6$H$_4$X, —CH$_2$C$_6$H$_3$X$_2$, —CH$_2$C$_6$H$_4$R$^1$, —CH$_2$C$_6$H$_3$R$_2^1$, —CH$_2$CH$_2$C$_6$H$_4$X, —CH$_2$CH$_2$C$_6$H$_3$X$_2$, CH$_2$CH$_2$C$_6$H$_4$R$^1$, —CH$_2$CH$_2$C$_6$H$_3$R$_2^1$, —CH═CR$_2^1$, —C—CR$^1$, —OR$^1$, —OC(O)R$^1$, —SiR$_3^1$, —OSiR$_3^1$, —NO$_2$, —NR$_2^1$, —N$_3$, —N═CR$_2^1$, —N═NR$^1$, —SR$^1$, —SX, —OSO$_2$R$^1$, —OSO$_2$OR$^1$, —SCN, —SO$_2$R$^1$, —PR$_2^1$, —PX$_2$, —P(O)R$_2^1$, —P(OR$^1$)$_2$, —P(O)(OR$^1$)$_2$, —OSiR$_3^1$, —OPR$_2^1$, —OAlR$_2^1$, —AsR$_2^1$, —As(O)R$_2^1$, —As(OR$^1$)$_2$, —As(O)(OR$^1$)$_2$, SnR$_3^1$, OSnR$_3^1$, SnX$_3^1$, OSnX$_3^1$, —BR$_2^1$, —BX$_2$, —BR$^1$X, —SO$_2$X, —OAlX$_2$, —OSiX$_3$, —OPX$_2$, —OSO$_2$X, —AsX$_2$, or —As(O)X$_2$; wherein R$^1$, in each instance, is independently selected from H or a substituted or unsubstituted hydrocarbyl group having from 1 to about 30 carbon atoms; and wherein X, in each instance, is independently selected from F, Cl, Br, I, H, OR$^1$, —SR$^1$, or NR$_2^1$.

In still a further aspect, the Mq$_n$-moiety can be functionalized by at least one group independently selected from alkyl, cycloalkyl, alkenyl, alkynyl, aryl, aralkyl, formyl, acyl, imide, amide, imine, alkoxide, aryloxide, alkylthiolate, arylthiolate, alkoxyalkyl, haloalkyl, carboxylate, or a substituted analog thereof, any one of which having up to about 30 carbon atoms.

Still a further aspect of this invention is an Mq$_n$-moiety that can be functionalized by at least one group independently selected from methyl, ethyl, propyl, cyclopropyl, n-butyl, tert-butyl, sec-butyl, isobutyl, cyclobutyl, amyl, isoamyl, pentyl, cyclopentyl, hexyl, cyclohexyl, cycloheptyl, heptyl, octyl, cyclooctyl, nonyl, decyl, dodecyl, 2-ethylhexyl, pentenyl, butenyl, benzyl, phenyl, tolyl, naphthyl, anthracenyl, F, Cl, Br, I, OMe, OEt, O-n-Pr, O-i-Pr, O-n-Bu, O-t-Bu, O-s-Bu, OPh, OC$_6$H$_4$Me, OC$_6$H$_3$Me$_2$, NMe$_2$, NEt$_2$, NPh$_2$, NHMe, NHEt, NHPh, —CH═O, —CH═CHC(O)

Ph, or a substituted analog thereof, any one of which having up to about 30 carbon atoms.

In still another aspect, this invention provides an $Mq_n$-functionalized monomer comprising a polymerizable moiety and an $Mq_n$-moiety, wherein q, in each instance, comprises an 8-hydroxyquinoline residue, and wherein the $Mq_n$-functionalized monomer further comprises a chemical spacer between the polymerizable moiety and the $Mq_n$-moiety, having between 1 and about 30 carbon atoms. In this formula, M is selected from Mg, Zn, Al, Ga, or In; and n is selected from 2 or 3 as dictated by the valence of the metal. Also in this aspect, this invention further provides a composition comprising the polymerization product of at least one $Mq_n$-functionalized monomer and at least one comonomer, wherein the $Mq_n$-functionalized monomer comprises a polymerizable moiety and an $Mq_n$-moiety, and wherein the $Mq_n$-functionalized monomer further comprises a chemical spacer between the polymerizable moiety and the $Mq_n$-moiety, having between 1 and about 30 carbon atoms. In one aspect, the chemical spacer can be selected from $-(CH_2)_nNHCH_2-$ or $-(CH_2)_nNR^2CH_2-$, wherein n in the formula of the spacer is from 1 to about 12, and $R^1$ is selected from a hydrocarbyl or substituted hydrocarbyl having from 1 to about 30 carbon atoms.

In a further aspect, this invention provides the polymerization product of at least one $Mq_n$-functionalized monomer and at least one comonomer, wherein the polymerization product comprises a block copolymer. This invention provides the polymerization product of at least one $Mq_n$-functionalized monomer and at least one comonomer, wherein the polymerization product comprises a random copolymer.

In still a further aspect, this invention provides a composition comprising the polymerization product of at least one $Alq_3$-functionalized monomer and at least one comonomer, wherein the $Alq_3$-functionalized monomer comprises a polymerizable moiety and an $Alq_3$-moiety, and wherein q, in each instance, comprises an 8-hydroxyquinoline residue, wherein the $Alq_3$-functionalized monomer can be selected from:

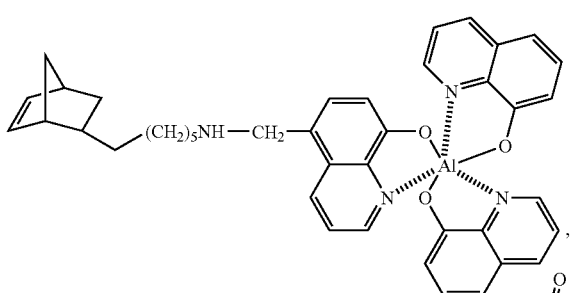

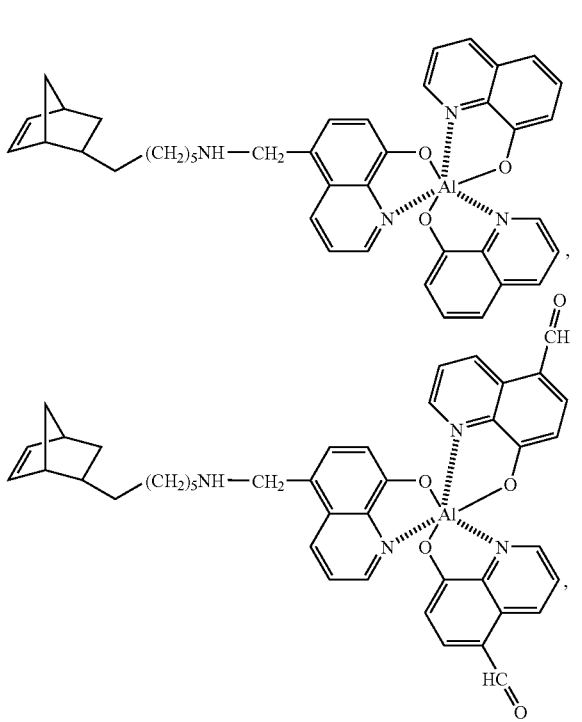

-continued

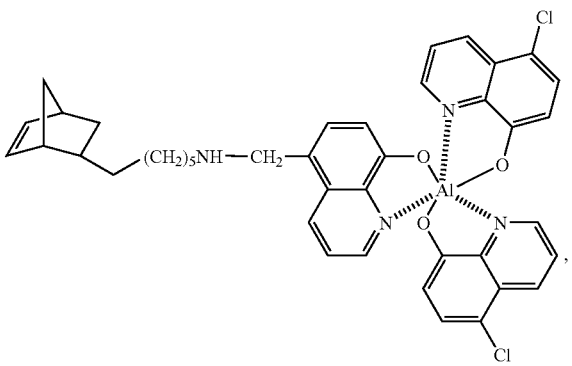

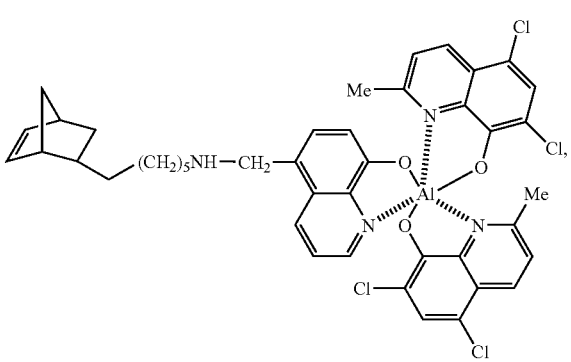

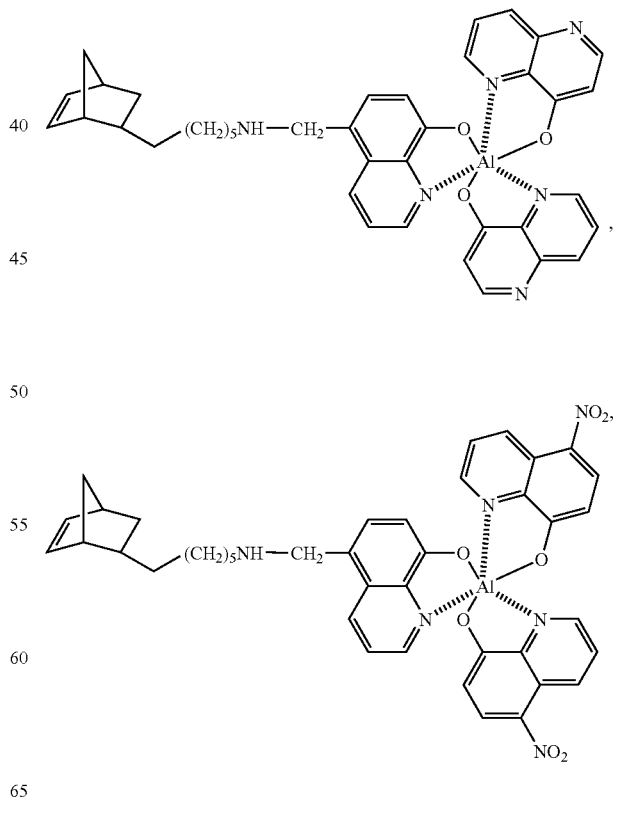

-continued

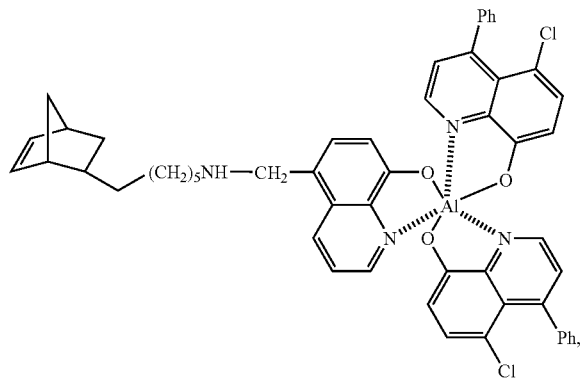

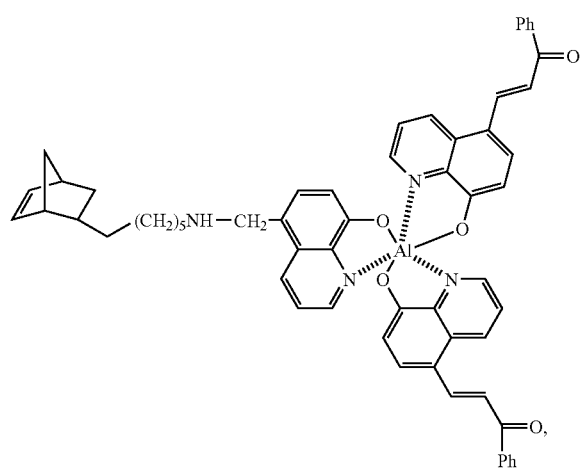

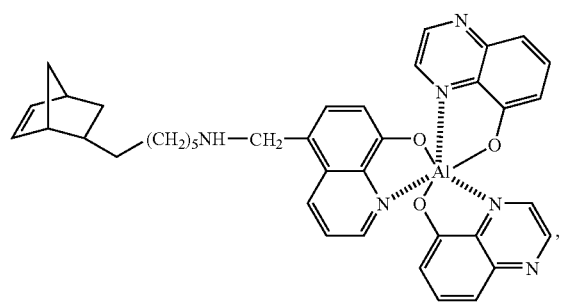

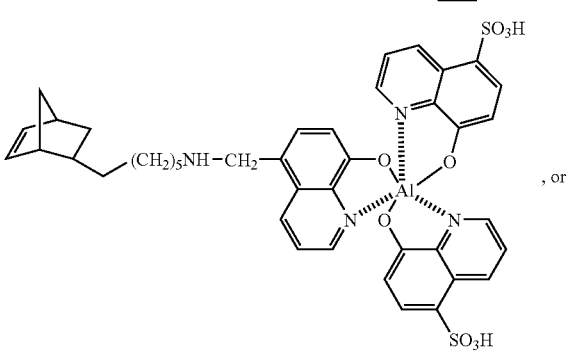

any combination thereof. In another aspect, the at least one comonomer can comprise a compound with the formula

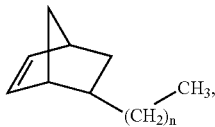

wherein n is an integer from 1 to about 12.

In a further aspect, this invention provides a composition comprising the polymerization product of at least one $Alq_3$-functionalized monomer and at least one comonomer, wherein the $Alq_3$-functionalized monomer comprises a polymerizable moiety and an $Alq_3$-moiety, and wherein the polymerization product can be characterized by a polydispersity (Mw/Mn) from about 1.5 to about 1.8. In another aspect, this invention provides a light-emitting diode comprising the polymerization product of at least one $Alq_3$-functionalized monomer and at least one comonomer, wherein the $Alq_3$-functionalized monomer comprises a polymerizable moiety and an $Alq_3$-moiety.

In still a further aspect, this invention provides a method of making an $Mq_n$-functionalized polymer, comprising:

polymerizing an $Mq_n$-functionalized monomer in the presence or absence of at least one comonomer;

wherein the $Mq_n$-functionalized monomer comprises a polymerizable moiety and an $Mq_n$-moiety; and wherein q, in each instance, comprises an 8-hydroxyquinoline residue; M is selected from Mg, Zn, Al, Ga, or In; and n is selected from 2 or 3 as dictated by the valence of the metal. In another aspect, the $Mq_n$-functionalized monomer can be polymerized in the presence of at least one comonomer. In this aspect, in the method disclosed herein, the $Mq_n$-functionalized monomer can be polymerized in the presence of at least one comonomer, and wherein the molar ratio of $Mq_n$-functionalized monomer to comonomer is from about 1:1 to about 1:20. Also in this aspect, the $Mq_n$-functionalized monomer can be polymerized in the presence of at least one comonomer comprising

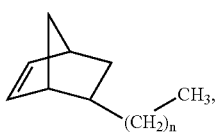

wherein n is an integer from 1 to about 12.

In another aspect, this invention provides a method of making an $Mq_n$-functionalized polymer, comprising:

polymerizing an $Mq_n$-functionalized monomer in the presence or absence of at least one comonomer;

wherein the $Mq_n$-functionalized monomer comprises a polymerizable moiety and an $Mq_n$-moiety; wherein the polymerizable moiety of the $Mq_n$-functionalized monomer can be selected from norborene, norbornadiene, cyclopentene, cyclooctene, cyclooctadiene, or a functionalized analog thereof. In this aspect, the method of making an $Mq_n$- functionalized polymer can comprise any polymerization method that converts the monomers and optional comonomers into polymers, including, but not limited to, a ring-opening metathesis polymerization (ROMP) method, a radical polymerization method, a controlled radical polymerization method, including, but not limited to, living radical polymerization methods, and the like. See, for example: Fischer, H. *Chem. Rev.* 2001, 101, 3581–3610; Hawker, C. J.; Bosman, A. W.; Harth, E. *Chem. Rev.* 2001, 101, 3661–3688; Kagigaito, M.; Ando, T.; Sawamoto, M. *Chem. Rev.* 2001, 101, 3689–3745; each of which is incorporated herein by reference in its entirety.

In still another aspect, the present invention provides a method of making an $Mq_n$-functionalized polymer, comprising polymerizing an $Mq_n$-functionalized monomer in the presence or absence of at least one comonomer, wherein the polymerization can be conducted in the presence of a catalyst comprising a transition metal carbene compound. In this aspect, the polymerization can be conducted in the presence of any ring-opening metathesis polymerization (ROMP) catalyst, as long as the monomers, functional groups, or conditions required for polymerization do not terminate the activity of the catalyst. In this aspect, the polymerization can be conducted in the presence of Grubbs' catalysts such as $Ru(CHPh)Cl_2[CHN_2(mesityl)_2C_2H_4](PCy_3)$ 11, as shown in the reaction schemes.

In still another aspect, the present invention provides a method of making an $Mq_n$-functionalized polymer comprising polymerizing an $Mq_n$-functionalized monomer in the presence or absence of at least one comonomer, wherein the $Mq_n$-moiety of the $Mq_n$-functionalized monomer can be functionalized with at least one group independently selected from: a hydrocarbyl group, an oxygen group, a sulfur group, a nitrogen group, a phosphorus group, an arsenic group, a carbon group, a silicon group, a germanium group, a tin group, a lead group, a boron group, an aluminum group, an inorganic group, an organometallic group, or a substituted analog thereof, any one of which having from 1 to about 30 carbon atoms; a halide; hydrogen; or any combination thereof.

In another aspect, this invention provides a method of making an $Mq_n$-functionalized polymer comprising polymerizing an $Mq_n$-functionalized monomer in the presence or absence of at least one comonomer, wherein the $Mq_n$-moiety of the $Mq_n$-functionalized monomer can be functionalized with at least one group independently selected from —F, —Cl, —Br, —I, —$R^1$, —$CR^1$=O, —CH=CHC(O)$R^1$, —C(O)$R^1$, —C(O)O$R^1$, —CN, —C(N$R^1$)$R^1$, —C(N$R^1$)O$R^1$, —$CH_2C_6H_4$X, —$CH_2C_6H_3X_2$, —$CH_2C_6H_4R^1$, —$CH_2C_6H_3R_2^1$, —$CH_2CH_2C_6H_4$X, —$CH_2CH_2C_6H_3X_2$, $CH_2CH_2C_6H_4R^1$, —$CH_2CH_2C_6H_3R_2^1$, —CH=$CR_2^1$, —C≡$CR^1$, —O$R^1$, —OC(O)$R^1$, —$SiR_3^1$, —$OSiR_3^1$, —$NO_2$, —$NR_2^1$, —$N_3$, —N=$CR_2^1$, —N=$NR^1$, —$SR^1$, —SX, —$OSO_2R^1$, —$OSO_2OR^1$, —SCN, —$SO_2R^1$, —$PR_2^1$, —$PX_2$, —$P(O)R_2^1$, —$P(OR^1)_2$, —$P(O)(OR^1)_2$, —$OSiR_3^1$, —$OPR_2^1$, —$OAlR_2^1$, —$AsR_2^1$, —$As(O)R_2^1$, —$As(OR^1)_2$, —$As(O)(OR^1)_2$, $SnR_3^1$, $OSnR_3^1$, $SnX_3^1$, $OSnX_3^1$, —$BR_2^1$, —$BX_2$, —$BR^1$X, —$SO_2$X, —$OAlX_2$, —$OSiX_3$, —$OPX_2$, —$OSO_2$X, —$AsX_2$, or —$As(O)X_2$; wherein $R^1$, in each instance, is independently selected from H or a substituted or unsubstituted hydrocarbyl group having from 1 to about 30 carbon atoms; and wherein X, in each instance, is independently selected from F, Cl, Br, I, H, $OR^1$, —$SR^1$, or $NR_2^1$.

In yet another aspect, this invention provides a method of making an $Mq_n$-functionalized polymer comprising polymerizing an $Mq_n$-functionalized monomer in the presence or absence of at least one comonomer, wherein the $Mq_n$-moiety of the $Mq_n$-functionalized monomer can be functionalized with at least one group independently selected from alkyl, cycloalkyl, alkenyl, alkynyl, aryl, aralkyl, formyl, acyl, imide, amide, imine, alkoxide, aryloxide, alkylthiolate, arylthiolate, alkoxyalkyl, haloalkyl, carboxylate, or a substituted analog thereof, any one of which having up to about 30 carbon atoms.

In still another aspect, this invention provides a method of making an $Mq_n$-functionalized polymer comprising polymerizing an $Mq_n$-functionalized monomer in the presence or absence of at least one comonomer, wherein the $Mq_n$-moiety of the $Mq_n$-functionalized monomer can be functionalized with at least one group independently selected from methyl, ethyl, propyl, cyclopropyl, n-butyl, tert-butyl, sec-butyl, isobutyl, cyclobutyl, amyl, isoamyl, pentyl, cyclopentyl, hexyl, cyclohexyl, cycloheptyl, heptyl, octyl, cyclooctyl, nonyl, decyl, dodecyl, 2-ethylhexyl, pentenyl, butenyl, benzyl, phenyl, tolyl, naphthyl, anthracenyl, F, Cl, Br, I, OMe, OEt, O-n-Pr, O-i-Pr, O-n-Bu, O-t-Bu, O-s-Bu, OPh, $OC_6H_4Me$, $OC_6H_3Me_2$, $NMe_2$, $NEt_2$, $NPh_2$, NHMe, NHEt, NHPh, —CH=O, —CH=CHC(O)Ph, or a substituted analog thereof, any one of which having up to about 30 carbon atoms.

In another aspect, this invention provides a method of making an $Alq_3$-functionalized polymer comprising polymerizing an $Alq_3$-functionalized monomer in the presence or absence of at least one comonomer, wherein the $Alq_3$-functionalized monomer further comprises a chemical spacer between the polymerizable moiety and the $Alq_3$-moiety, having between 1 and about 30 carbon atoms. In another aspect, for example, the chemical spacer can be selected from —$(CH_2)_n$$NHCH_2$— or —$(CH_2)_n$$NR^1CH_2$—, wherein n in the chemical spacer formula is from 1 to about 12, and $R^1$ is selected from a hydrocarbyl or substituted hydrocarbyl having from 1 to about 30 carbon atoms.

In still another aspect, this invention provides a method of making an $Alq_3$-functionalized polymer comprising polymerizing an $Alq_3$-functionalized monomer in the presence or absence of at least one comonomer, wherein the polymerization product comprises a block copolymer.

In another aspect, this invention provides a method of making an $Alq_3$-functionalized polymer comprising polymerizing an $Alq_3$-functionalized monomer in the presence or absence of at least one comonomer, wherein the $Alq_3$-functionalized monomer is selected from:

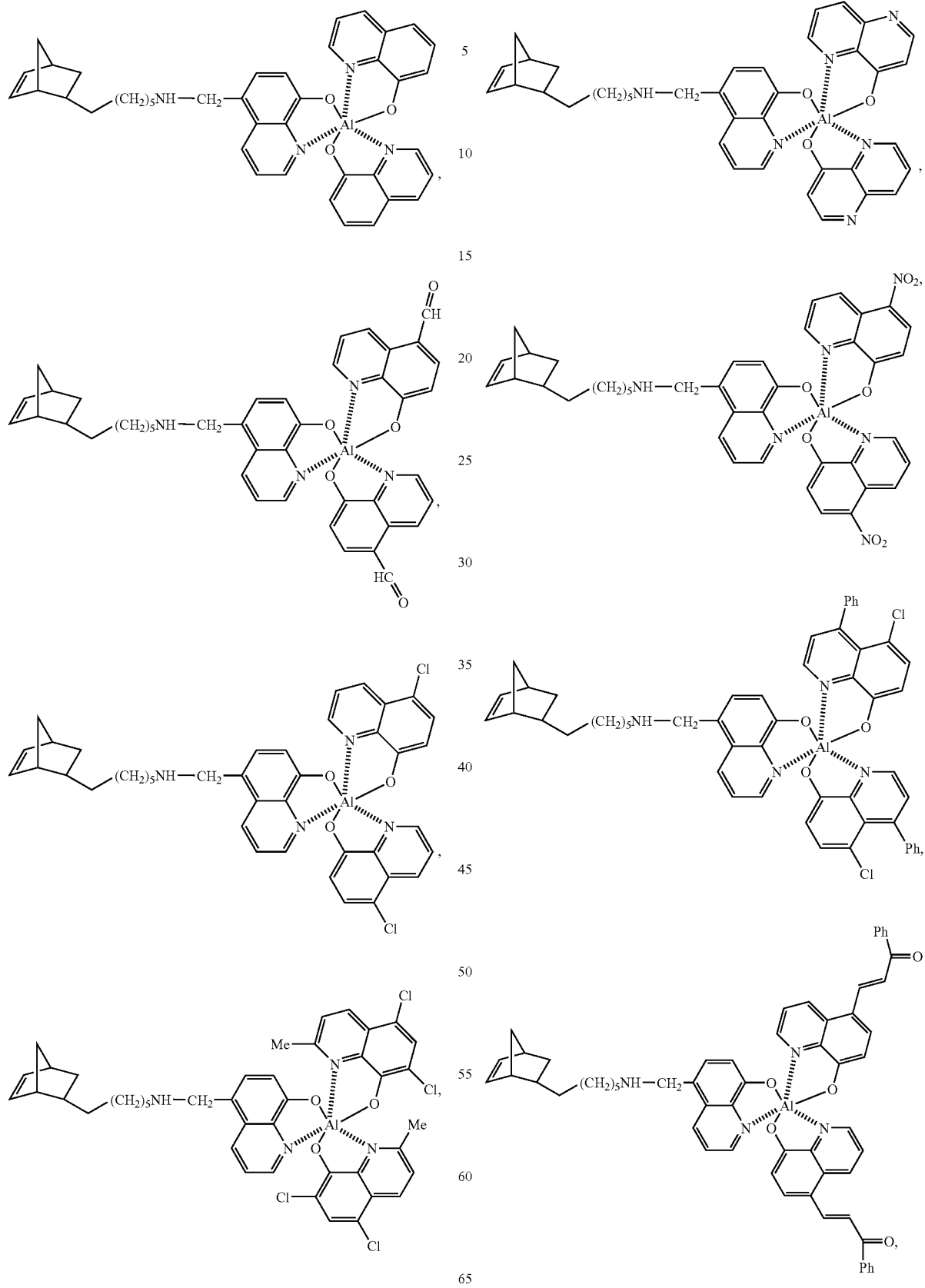

-continued

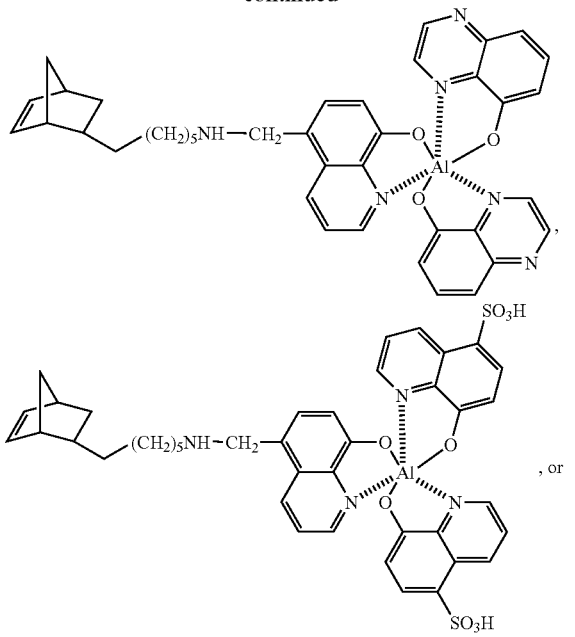

any combination thereof.

In yet another aspect, the present invention provides a method of functionalizing a polymer with an $Alq_3$ moiety, comprising:

providing an $Alq_3$-functionalized monomer; and polymerizing an $Alq_3$-functionalized monomer in the presence or absence of at least one comonomer;

wherein the $Alq_3$-functionalized monomer comprises a polymerizable moiety and an $Alq_3$-moiety; and wherein q, in each instance, comprises an 8-hydroxyquinoline residue.

Optical Properties of Selected $Mq_n$-Functionalized Polymers

The photoluminescence of the $Alq_3$-functionalized copolymers and monomer 9 were investigated and compared to the photo luminescence of $Alq_3$ itself. As a measure of the baseline performance of the copolymers and monomer 9, commercial $Alq_3$ was treated with the same chloroform/trifluoroacetic acid mixture as the copolymers. No changes were detected in the optical properties of $Alq_3$ after this treatment, as compared to the optical properties of $Alq_3$ before this treatment.

The UV/Visible absorption spectrum of monomer 9 shows a $\lambda_{max}$ at 319 nm, corresponding to the low-energy singlet transition of the hydroxyquinoline group. (See: Ravi Kishore, V. V. N.; Aziz, A.; Narasimhan, K. L.; Periasamy, N.; Meenakshi, P. S.; Wategaonkar, S. Synth. Met. 2002, 126, 199–205, which is incorporated by reference herein, in its entirety.) The absorption spectrum of $Alq_3$ showed peaks at 372 nm and at 316 nm, consistent with the reported spectrum. (See: Halls, M. D.; Schlegel, H. B. Chem. Mater. 2001, 13, 2632–2640, which is incorporated by reference herein, in its entirety.) FIG. 1 illustrates the UV/Visible absorption spectra of $Alq_3$, the $Alq_3$-containing monomer 9, and the series of 9:12 copolymers in $CHCl_3$ solution, as described in Table 1. The absorption spectra of all the copolymers examined showed identical peaks as that of $Alq_3$, indicating the same transitions taking place in the copolymer system as the ones known for $Alq_3$. Absorption and photoluminescence data for 9, $Alq_3$, and a series of co-polymers recorded on relatively dilute solutions are presented in Table 2, as compared to the data recorded in Table 1.

TABLE 2

Absorption and photoluminescence data for 9, $Alq_3$, and a series of 9:12 co-polymers recorded on relatively dilute solutions.

| Sample | UV/Vis conc. (mg/mL) | UV/Vis $\lambda_{max}$ (nm) | Fluorescence conc. (mg/mL) | Fluorescence $\lambda_{max}$ (nm) |
|---|---|---|---|---|
| Monomer 9 | 0.045 | 319 | NA | NA |
| $Alq_3$ | 0.12 | 316, 372 | 0.009 | 506 |
| 1:4 Polymer | 0.20 | 313, 375 | 0.020 | 506 |
| 1:5 Polymer | 0.058 | 314, 378 | 0.023 | 505 |
| 1:10 Polymer | 0.072 | 314, 378 | 0.028 | 512 |

Figure 2:
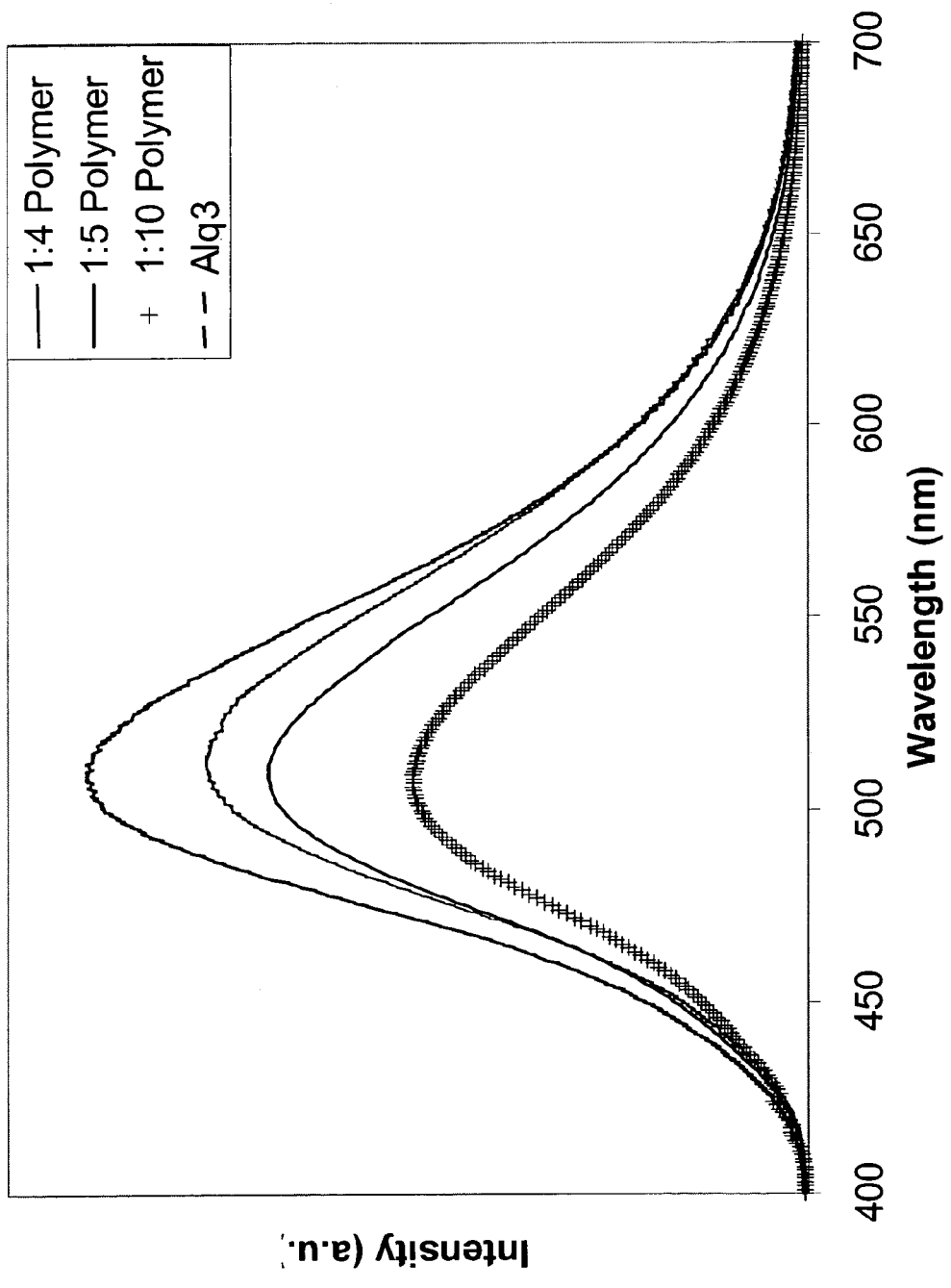
FIG. 2 illustrates the emission spectra of $Alq_3$ and the series of 9:12 copolymers in $CHCl_3$ solution, excited at 380 mn, as described in Table 1.

The emission spectra of $Alq_3$ and the copolymers were collected from 400–700 nm, with an excitation wavelength of 380 nm. FIG. 2 illustrates the emission spectra of $Alq_3$ and the series of 9:12 copolymers in $CHCl_3$ solution, excited at 380 nm, as described in Table 1. As shown in FIG. 2, all copolymers fluoresce at the same wavelength as $Alq_3$ in solution, demonstrating that the emission properties of $Alq_3$ are retained in the polymer matrix.

The ratio of $Alq_3$-monomer to the non-functionalized monomer in the copolymers affected the intensity of the emission. Thus the intensity showed a linear relationship with the percentage of $Alq_3$ present in the copolymer, as indicated by the data provided in Table 1. While not intending to be bound by theory, these studies suggest that the optical properties of $Alq_3$ are preserved in the polymer and not affected by the polymer coil while in solution. Upon spin-casted the copolymer solutions to provide thin films of the $Alq_3$-functionalized polymer, the resulting films exhibited fluorescence emission similar to that of $Alq_3$ in the solid state. Table 2 provides absorption and photoluminescence data for 9, $Alq_3$, and a series of co-polymers recorded on relatively dilute solutions, as compared to the data recorded in Table 1.

While not intending to be bound by theory, when comparing $Alq_3$-functionalized polymers to the other $Mq_n$-functionalized polymers, fluorescence is generally expected to be reduced with increasing atomic number of the metal ion, which is referred to as the heavy atom effect. In addition, as the covalent bond character between metal and quinoline ligand increases, the $Mq_n$ complexes are expected to become more red shifted. For example, and again while not intending to be bound by theory, the analogous Al, Ga, and In complexes would be expected to emit at progressively longer wavelengths (red shifted). See, for example: Chen, C. H.; Shi, J. Coord. Chem. Rev. 1998, 171, 161–174, which is incorporated herein by reference in its entirety.

Preparation of Selected $Mq_n$-Functionalized Polymers With an Electronically-Tuned Ligand Sphere Another aspect of this invention is an $Mq_n$-functionalized polymer with an electronically-tuned ligand sphere about the metal center. In this aspect, this invention provides a composition comprising the polymerization product of an $Mq_n$-functionalized monomer, wherein the $Mq_n$-functionalized monomer can comprise a polymerizable moiety and an $Mq_n$-moiety, wherein q, in each instance, comprises an 8-hydroxyquinoline residue, and M is selected from Mg, Zn, Al, Ga, or In; and n is selected from 2 or 3 according to the valence of the metal. Further to this aspect, this invention provides a composition comprising the polymerization product of an Alq$_3$-functionalized monomer, which can comprise a polymerizable moiety and an Alq$_3$-moiety, and wherein q, in each instance, comprises an 8-hydroxyquinoline residue, which, in accordance with this invention, can include a residue of an 8-hydroxyquinoline-like compound, or a functionalized analog of an an 8-hydroxyquinoline or an 8-hydroxyquinoline-like compound. Further in this aspect, the Alq$_3$-moiety of the Alq$_3$-functionalized monomer can be functionalized with at least one electron-donating group, at least one electron-withdrawing group, or a combination thereof. For example, the ligand sphere around the aluminum center on the polymer can be functionalized with electron-donating or withdrawing groups thereby allowing the emission of the polymer to be tuned from blue to yellow (from about 430 nm to about 549 nm).

In one aspect, this invention provides the ability to tune the emission of the Alq$_3$-functionalized monomer, and hence the Alq$_3$-functionalized polymer, according to the functionalization of the ligand sphere around the aluminum center on the polymer with electron-donating, withdrawing groups, or a combination thereof.

In one aspect, this invention provides for the modification of the 8-hydroxyquinoline ligand with electron-donating or withdrawing groups, thereby changing the HOMO-LUMO gap of the substituted 8-hydroxyquinoline ligands. (See, for example: Hopkins, T. A.; Meerholz, K.; Shaheen, S.; Anderson, M. L.; Schmidt, A.; Kippelen, B.; Padias, A. B.; H. K. Hall, J.; Peyghambarian, N.; Armstrong, N. R. *Chem. Mater.* 1996, 8, 344–351; Jang, H.; Do, L. -M.; Kim, Y.; Zyung, T.; Do, Y. *Synth. Met.* 2001, 121, 1667–1668; each of which is incorporated by reference herein in its entirety.)

In still another aspect, this invention provides for the introduction of heteroatoms into the 8-hydroxyquinoline ring system, which can have a profound effect on the electronic structure and the resulting the emission of the corresponding Mq$_n$-functionalized monomer and Mq$_n$-functionalized polymer. In this aspect, for example, substitution of a nitrogen atom in an 8-hydroxyquinoline ring system, including, but not limited to the 4- or 5-position, can result in either a large blue-shift or a large red-shift, respectively. Also in this aspect, terms such as Mq$_n$, Mq$_n$-functionalized compound, Mq$_n$-functionalized polymer, 8-hydroxyquinoline ligand, and the like, are used to refer to Mq$_n$-like compounds and 8-hydroxyquinoline ligands that are modified with electron-donating or withdrawing groups, and are similarly used to refer to Alq$_3$-like compounds and 8-hydroxyquinoline ligands that are modified by introduction of heteroatoms into the 8-hydroxyquinoline ring system.

Figure 3:
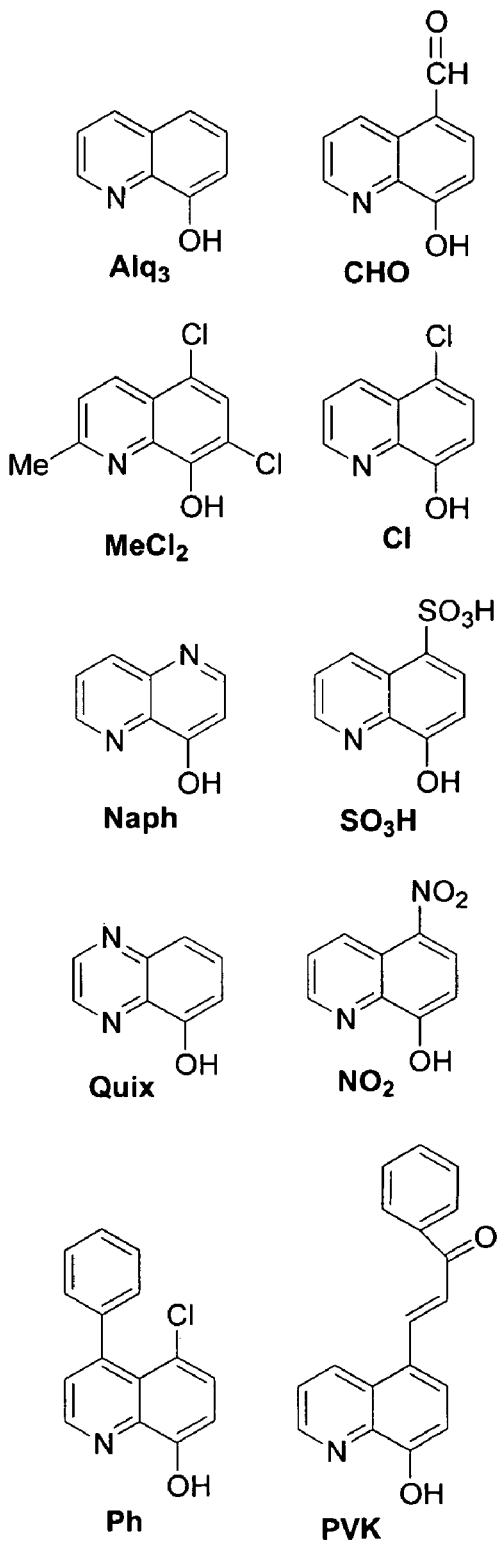
FIG. 3 provides examples of modified 8-hydroxyquinoline ligands used in the preparation of functionalized $Alq_3$-containing monomers and $Alq_3$-containing polymers.

The synthesis of the modified Alq$_3$-functionalized monomers is shown in Scheme 5, in which the 8-hydroxyquinoline ring system is modified with electron-donating or withdrawing groups, or by the introduction of heteroatoms into the 8-hydroxyquinoline ring system. The structures of the resulting monomers are illustrated in Table 3. The functionalized 8-hydroxyquinoline ligands employed in this Scheme, represented by "X", are shown in FIG. 3, along with the abbreviations used to designate these ligands. Thus, as illustrated in Scheme 5, the typical modified Alq$_3$-containing monomer has one 8-hydroxyquinoline ligand coordinating the aluminum that derived from the polymerizable molecule comprising a norbornene moiety, while the other two 8-hydroxyquinoline ligands constitute the 8-hydroxyquinoline ring systems that are modified with electron-donating or withdrawing groups, or by the introduction of heteroatoms. A large number of these functionalized 8-hydroxyquinoline molecules are commercially available from, for example, LaboTest (Niederschöna, Germany) and can be used in this invention.

TABLE 3

Functionalized Alq$_3$Containing Monomers

| Compound Number | Ligand X | Monomer Structure | Ligand X Abbreviation |
|---|---|---|---|
| 15a | (8-hydroxyquinoline structure) | (norbornene-(CH$_2$)$_5$NH·CH$_2$-linked Alq$_3$ structure) | Alq$_3$ |

TABLE 3-continued

Functionalized Alq₃Containing Monomers

Monomer Structure

| Compound Number | Ligand X | | Ligand X Abbreviation |
|---|---|---|---|
| 15b | 5-formyl-8-hydroxyquinoline | | CHO |
| 15c | 5-chloro-8-hydroxyquinoline | | Cl |
| 15d | 5,7-dichloro-2-methyl-8-hydroxyquinoline | | MeCl₂ |

TABLE 3-continued
Functionalized Alq₃Containing Monomers
Monomer Structure
| Compound Number | Ligand X | | Ligand X Abbreviation |
|---|---|---|---|
| 15e | 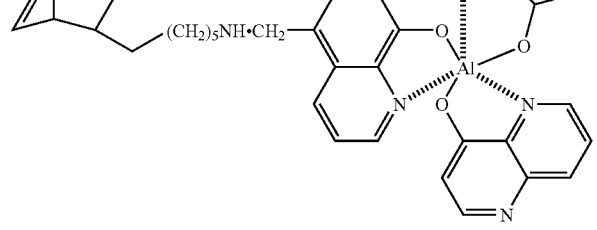 | 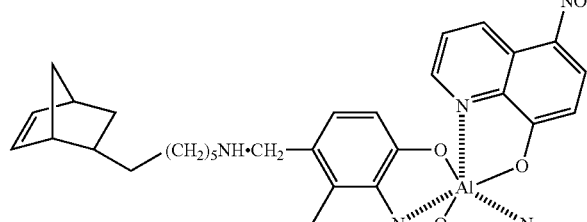 | Naph |
| 15f | 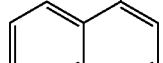 | 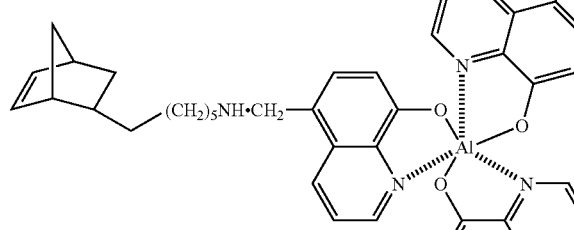 | $NO_2$ |
| 15g |  | 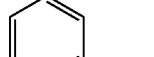 | Ph |

TABLE 3-continued

Functionalized Alq₃Containing Monomers

Monomer Structure

| Compound Number | Ligand X | | Ligand X Abbreviation |
|---|---|---|---|
| 15h | (chalcone-substituted 8-hydroxyquinoline structure) | (Al complex structure with norbornene-(CH₂)₅NH·CH₂ linker and two chalcone-quinolinolate ligands) | PVK |
| 15i | (8-hydroxyquinoxaline structure) | (Al complex structure with norbornene-(CH₂)₅NH·CH₂ linker and two quinoxalinolate ligands) | Quinox |
| 15j | (5-sulfo-8-hydroxyquinoline structure, SO₃H) | (Al complex structure with norbornene-(CH₂)₅NH·CH₂ linker and two SO₃H-substituted quinolinolate ligands) | SO₃H |

As illustrated in Scheme 5 and in the Examples, metallation of monomer 3 was carried out by the addition of 8 to a solution of triethylaluminum, resulting in the formation of the metallated monomer 14. The addition of two equivalents of the modified 8-hydroxyquinoline ligands X to monomer 14 resulted in the formation of monomers 15a–15j (referred to generically as 15) in quantitative yields. Examples of the functionalized 8-hydroxyquinoline ligands include, but are not limited to, those ligands shown in FIG. 3 and Table 3.

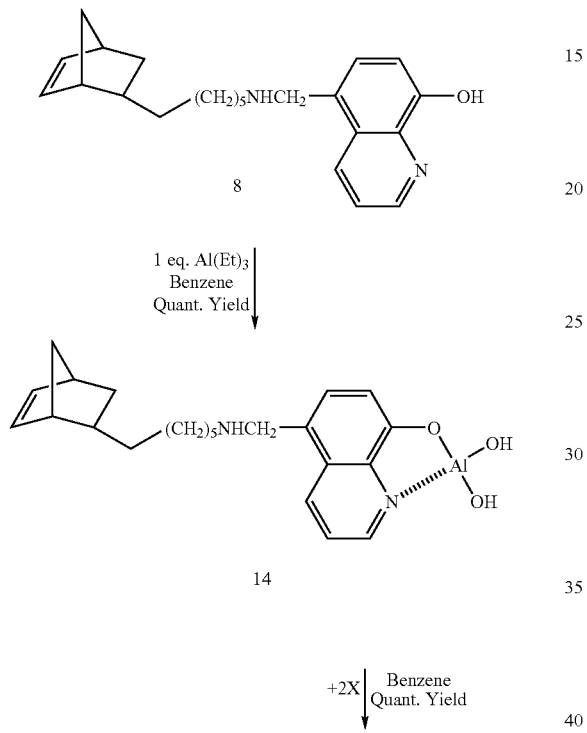

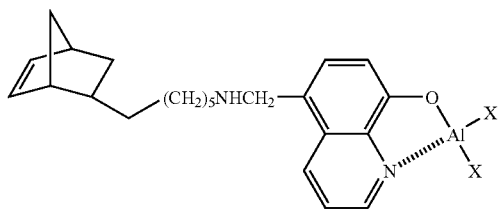

Scheme 6 illustrates that polymerizations were carried out by combining 12 and 15 in chloroform and adding catalyst 11. Thus, co-polymerization with nonylnorbomene was employed to render all polymers highly soluble in common organic solvents. In one aspect, a molar ratio of $AlqX_2$-monomer to nonylnorbornene of about 1:20 was used in all fluorescence studies unless otherwise noted, which provided good results.

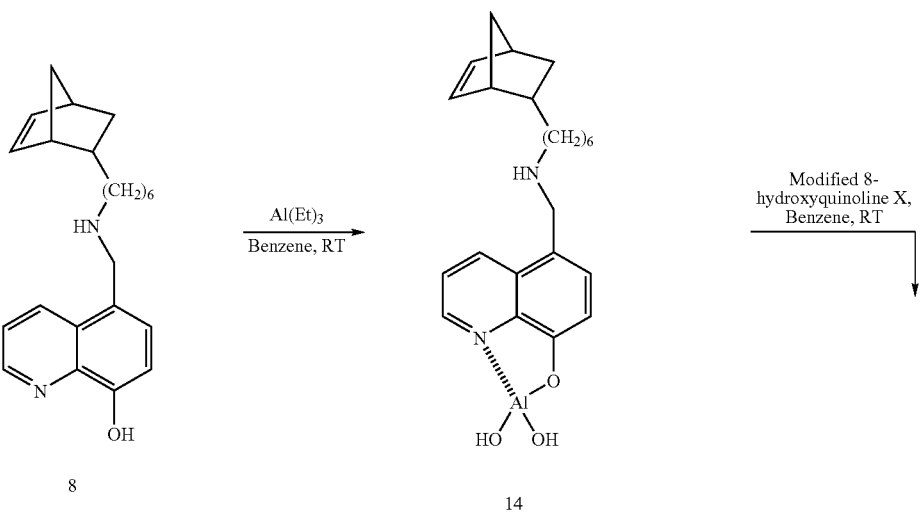

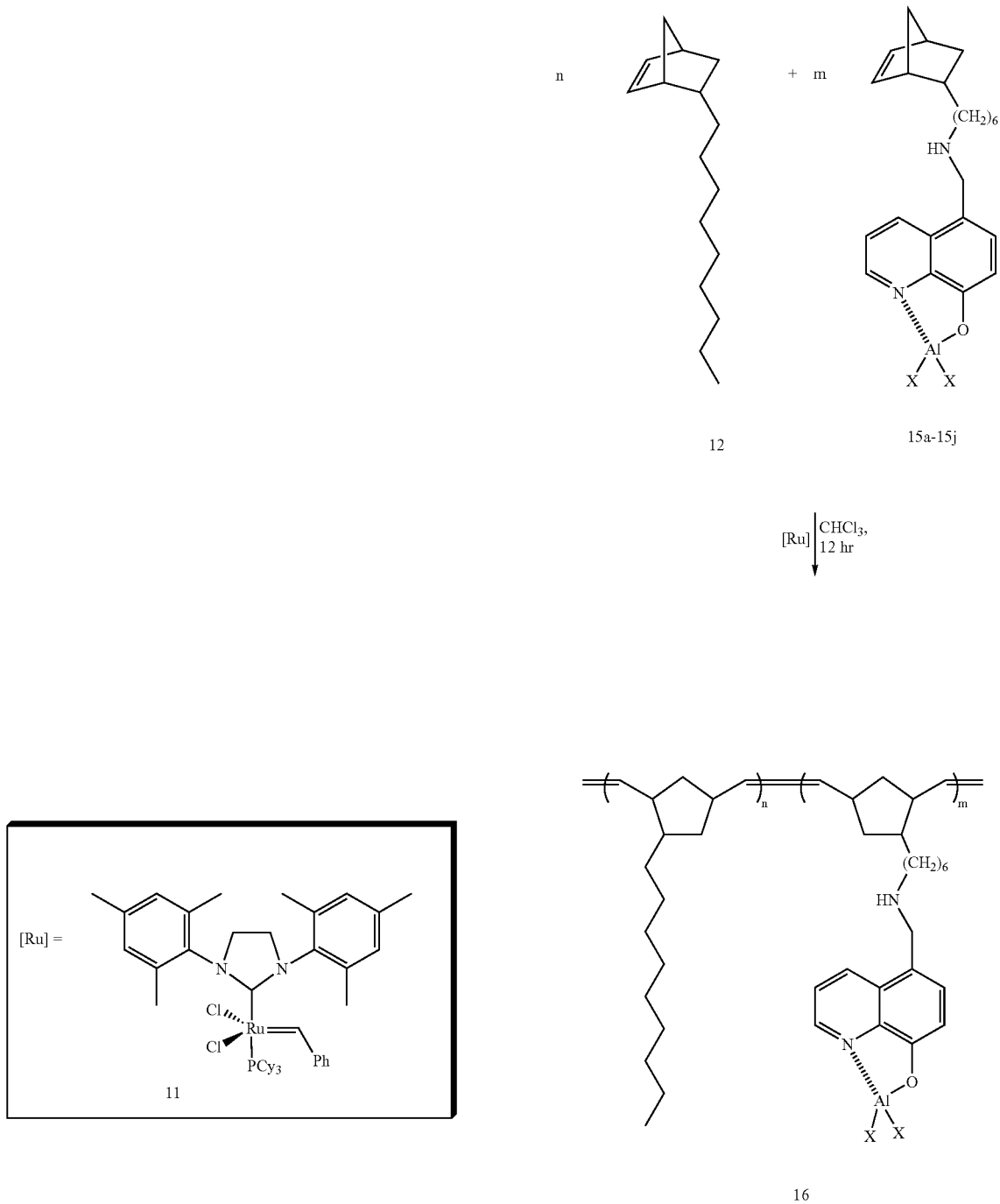

In still another aspect, this invention provides for the use of a variety of polymerizable moieties other than norborene to be used in the preparation of the $Mq_n$-functionalized monomers and the $Mq_n$-functionalized polymers. In one aspect, for example, the preparation of an $Alq_3$-functionalized monomer, comprising a cyclooctene polymerizable moiety, is presented in Scheme 7. The preparation provided in Scheme 7 is applicable to the range of $Mq_n$-functionalized monomers and the $Mq_n$-functionalized polymers.

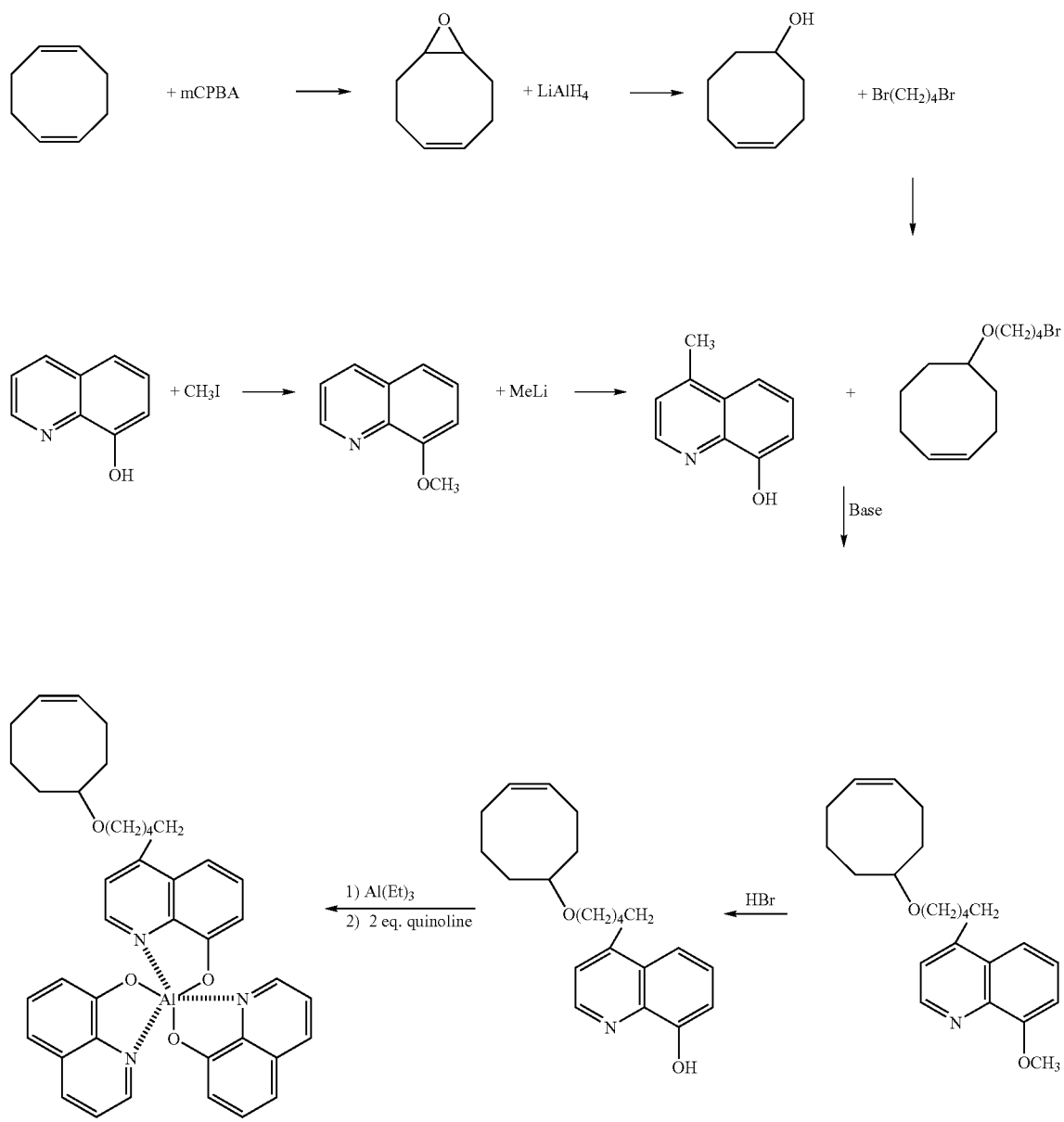

Scheme 7

In still another aspect, this invention provides for the preparation of zinc-containing monomers and polymers, as illustrated in Scheme 8. Thus, Scheme 8 illustrates that polymerizations were carried out by combining 12 and 17 in solution and adding catalyst 11. Thus, co-polymerization with nonylnorbornene was employed to render all polymers highly soluble in common organic solvents. In one aspect, a molar ratio of Znq$_2$-monomer or ZnqX-monomer to nonyl-norbornene of about 1:20 was used in all fluorescence studies unless otherwise noted, which provided good results. As in the aluminum compounds, the design, synthesis, and characterization of the Znq$_2$-copolymers, demonstrated excellent photoluminescence properties, with emission wavelengths ranging from the blue to the yellow, while retaining the solution processability. Accordingly, these copolymers could be used in electroluminescent devices.

To examine and improve solubilities, monomer 8 was co-polymerized with a spacer monomer, nonylnorbornene 12, in ratios of 1:1, 1:5, 1:10, and 1:20 (8/12), resulting in copolymers that were readily soluble. The 1:20 ratios were used to characterize the optical properties of the copolymers, unless otherwise noted.

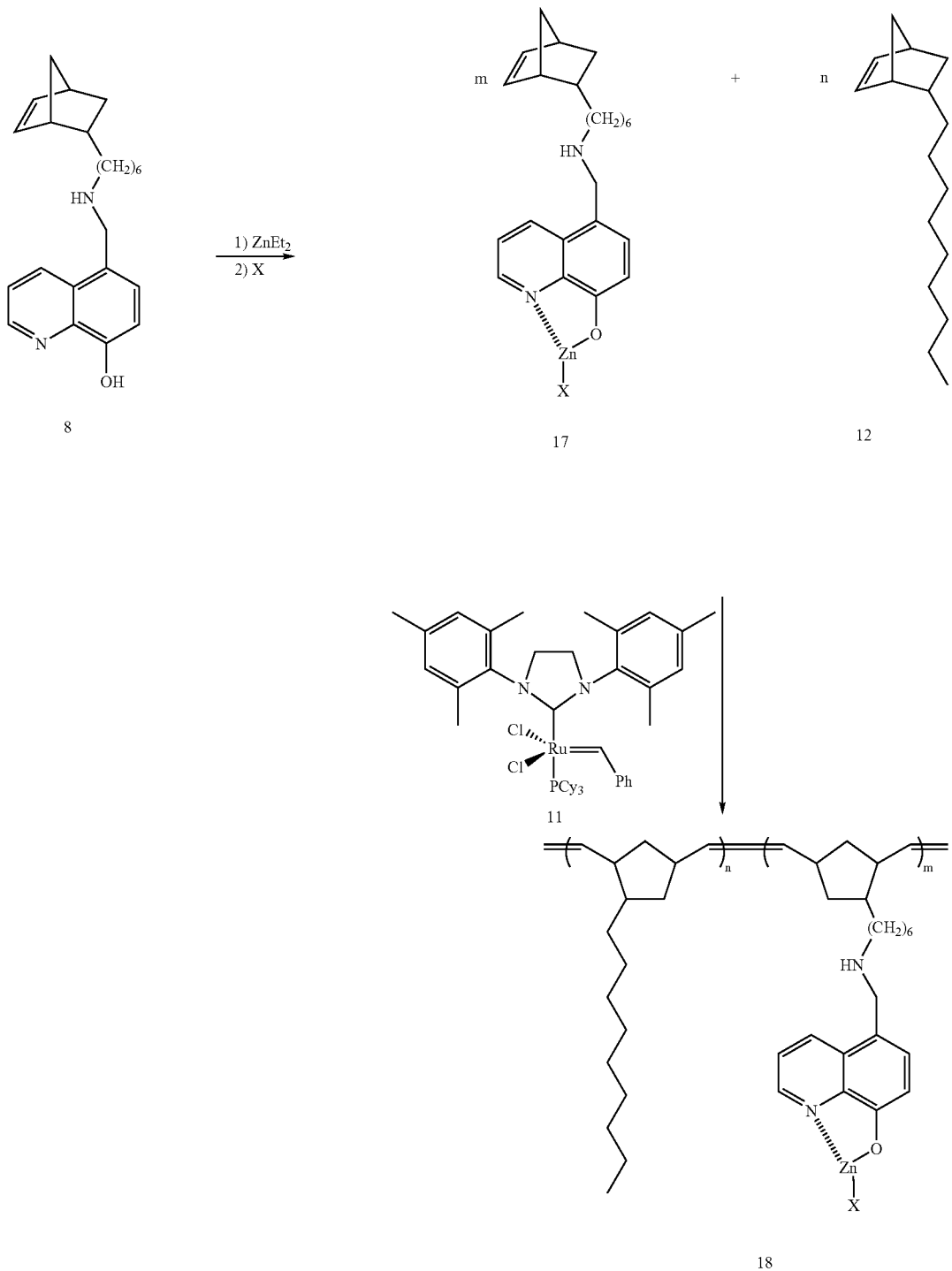

Chemical, Physical, and Optical Properties of Alq$_3$-Functionalized Polymers With an Electronically-Tuned Ligand Sphere The Alq$_3$-functionalized polymers with electronically-tuned ligand spheres were characterized by NMR, gel-permeation chromatography (GPC), differential scanning calorimetry (DSC), and thermogravimetric analysis (TGA), with the results summarized in Table 4. The polymerizations were followed by NMR and were considered complete when no olefin signals were detected. In one aspect, the molecular weights of the polymers, determined by GPC, ranged from about 7000 to about 55000, with polydispersities (PDI) from about 1.26 to about 2.74. All polymers showed a decomposition temperature around 250° C., with no glass transition or any other endotherms being detected under the conditions used.

TABLE 4

The monomer molar ratios, modified ligands, and molecular weight and polydispersity properties of $Alq_3$-functionalized polymers of this invention.

| Polymer[a] | m/n ratio | X | Mn | Mw | PDI |
|---|---|---|---|---|---|
| $Alq_3$110 | 1:10 | $Alq_3$ | 11000 | 16300 | 1.47 |
| $Alq_3$120 | 1:20 | $Alq_3$ | 7600 | 11600 | 1.53 |
| $Alq_3$150 | 1:50 | $Alq_3$ | 24000 | 58400 | 2.43 |
| $Alq_3$500mer[b] | 1:20 | $Alq_3$ | 10400 | 18600 | 1.77 |
| $Alq_3$1000mer[b] | 1:20 | $Alq_3$ | 19400 | 35400 | 1.82 |
| Bu | 1:20 | Bu | 6600 | 16100 | 2.46 |
| CHO110 | 1:10 | CHO | 14200 | 29200 | 2.06 |
| CHO120 | 1:20 | CHO | 24200 | 52600 | 2.16 |
| CHO150 | 1:50 | CHO | 19000 | 42600 | 2.24 |
| Cl | 1:20 | Cl | 17500 | 43000 | 2.45 |
| $MeCl_2$ | 1:20 | $MeCl_2$ | 15000 | 28700 | 1.92 |
| Naph120 | 1:20 | Naph | 21100 | 35100 | 1.67 |
| $NO_2$ | 1:20 | $NO_2$ | 11000 | 17000 | 1.56 |
| Ph | 1:20 | Ph | 17300 | 38300 | 2.21 |
| PVK110 | 1:10 | PVK | 14500 | 27500 | 1.89 |
| PVK120 | 1:20 | PVK | 10200 | 20800 | 2.04 |
| PVK150 | 1:50 | PVK | 20000 | 55000 | 2.74 |
| Quinox | 1:20 | Quinox | 15600 | 31200 | 1.99 |
| $SO_3H$ | 1:20 | $SO_3H$ | 4700 | 7700 | 1.63 |

[a]Polymers are named after the functionalized ligand X and the molar ratio of 15:12. If a number is not present, then the polymer was composed of a 1:20 15:12 ratio.
[b]500mer and 1000mer refer to the number of repeat units in the polymer.

Solution Fluorescence Studies on $Alq_3$ Complexes

Figure 4:
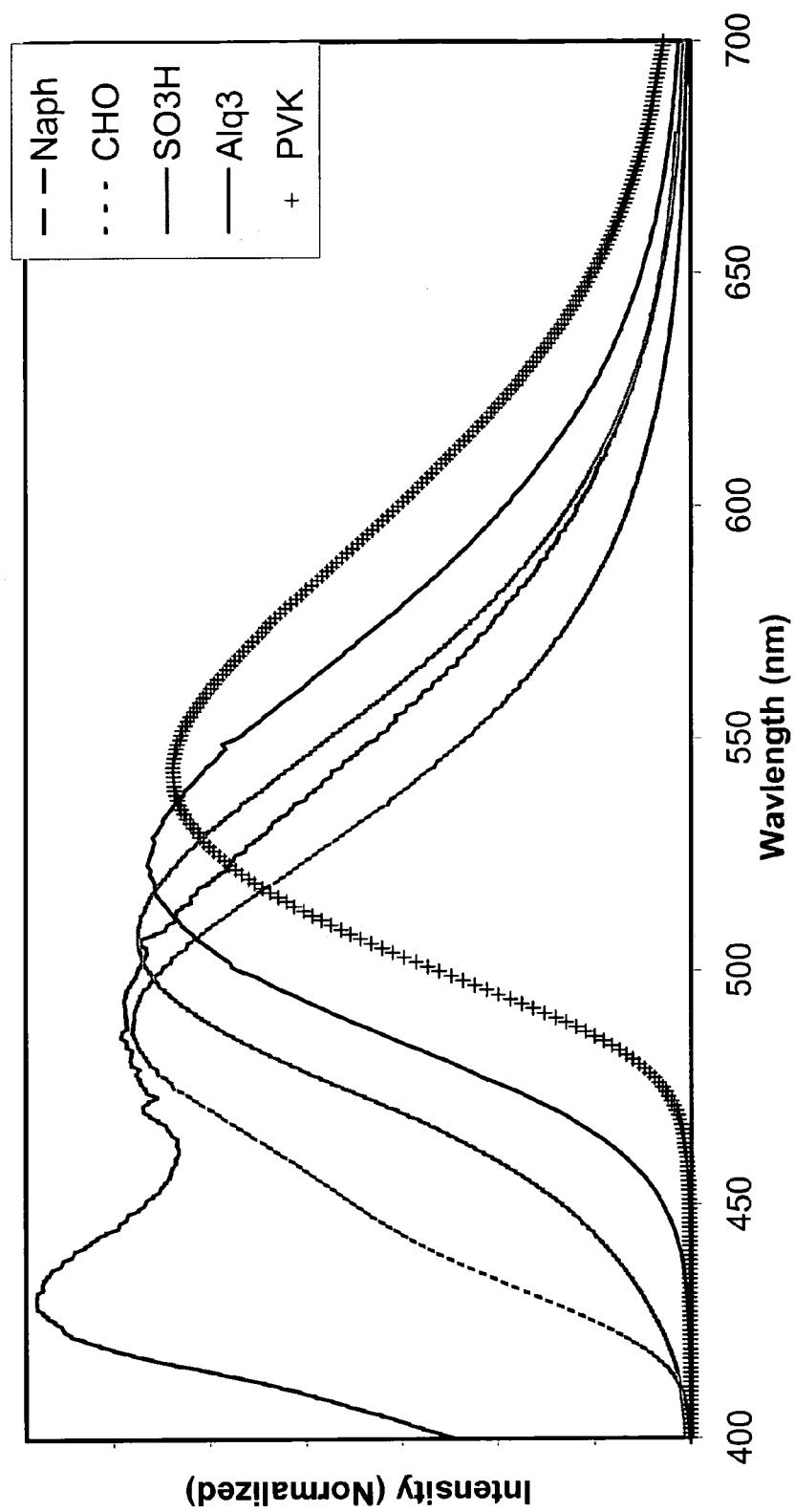
FIG. 4 provides normalized solution emission spectra of selected modified polymers in chloroform.

The normalized solution emission spectra of selected modified polymers in chloroform are presented in FIG. 4. Solution emission results are also summarized in Table 5. The unmodified $Alq_3$-polymer ($Alq_3$) was observed to emit at the same wavelength as pure $Alq_3$ (523 nm). Similar to modified-$Alq_3$, the polymers containing functionalized $Alq_3$ side-chains show either a blue- or red-shifted emission, depending on the functionalization. While most of the modified 8-hydroxyquinoline ligands induce shifts in the emission spectra, the most noticeable shifts result from polymers functionalized with either the 4-hydroxy-1,5-naphthyridine (Naph) or the quinoxalinol (Quinox) ligands. The naphthyridine ligand induces a strong blue-shifted of about 90 nm, while the quinoxalinol ligand induces a red-shifted of about 50 nm. Other dramatic shifts occurred after functionalization with the aldehyde-functionalized ligand (CHO) (−32 nm) and the phenyl-vinyl-ketone-functionalized ligand (PVK) (+21 nm).

Less dramatic blue- or red-shifts were observed for the polymers based on dichloromethyl-($MeCl_2$), chloride-(Cl), and sulfonic acid-($SO_3H$) functionalized hydroxyquinolines. The phenyl-functionalized (Ph) polymer was observed not to shift the emission wavelength, perhaps because the donating ability of the phenyl group was offset by the withdrawing ability of the chloride group. The nitro-polymer ($NO_2$) did show a 20 nm blue-shift, but the intensity of this emission was very low in comparison to all other polymers. While not intending to be bound by theory, these shifts can be rationalized by considering the electron-donating and electron-withdrawing ability of the substituents on the modified ligands.

TABLE 5

Excitation and emission wavelength for the polymers in solution and the solid-state.

| Polymer[a] | Excitation λ (nm) | Solution Emission $\lambda_{max}$ (nm) | Solid-State Emission $\lambda_{max}$ (nm) |
|---|---|---|---|
| $Alq_3$ | 380 | 523 | 511 |
| Bu | 380 | 522 | 515 |
| CHO | 380 | 488 | 510 |
| Cl | 380 | 537 | 520 |
| $MeCl_2$ | 380 | 510 | 505 |
| Naph | 330 | 430, 490 | 437, 498 |
| $NO_2$ | 380 | 510 | n/a |
| Ph | 380 | 524 | n/a |
| PVK | 380 | 543 | 537 |
| Quinox | 400 | 570 | n/a |
| $SO_3H$ | 380 | 508 | 495 |
| Alq500mer[b] | 380 | 523 | 510 |
| Alq1000mer[b] | 380 | 522 | 512 |

[a]Polymers are named after the functionalized ligand X; all polymers comprise a 1:20 ratio of 15:12.
[b]500mer and 1000mer refer to the number of repeat units in the polymer.

The emission spectrum of the Naph-polymer shows two maxima, one at 430 nm and the other one at 490 nm. The two maxima can be attributed to the two different ligands around the aluminum center, namely, two naphthyridine ligands and one hydroxyquinoline ligand. Again, while not intending to be bound by theory, it is likely that the peak at 430 nm arises from an oriented naphthyridine ligand, while the emission peak at 490 nm arises from the hydroxyquinoline ligand. The electronics of the hydroxyquinoline ligand are affected by the naphthyridine ligand, resulting in a blue-shift from the usual 520 nm. This idea was tested by preparing the small molecule counterpart containing two naphthyridine ligands and one hydroxyquinoline ligand around an aluminum center. The emission spectrum of this compound was identical to that of the polymer. This two ligand effect can also be seen in the CHO-polymer, with a small shoulder occurring at 450 nm.

These data from the solution emission studies suggest that the polymer backbone does not interfere with the optical properties of the $Alq_3$ side-chain, and that the emission can be tuned through simple ligand modifications.

Thus, in one aspect of this invention, using electron-donating or electron-withdrawing ligands that can shift the photoluminescence, the emission of the functionalized polymers can be tuned in solution as well as in the solid-state from ranging from about 490 nm up to about 550 nm. The intensity of the solid-state emission can also be altered by adjusting the concentration of the polymer solution before spin-casting, while the emission wavelength can be shifted up to about 30 nm by changing the chromophore density.

Thin-Film Characterization of $Alq_3$-Containing Polymers

Thin films of the functionalized $Alq_3$-containing polymers were fabricated by spin coating techniques and were characterized using optical microscopy, ellipsometry, and fluorescence spectroscopy. The thicknesses of the films ranged from about 200 nm to about 600 nm depending on the concentration of the polymer solution. The uniformity of the films was observed using an inverted microscope while irradiating the films with UV light. These observations indicated that all of the films showed very smooth surfaces with good uniformity and very few defects.

Experiments were conducted to determine if the functionalized $Alq_3$-containing polymers could support a current. Thin films of 1:5, 1:10, and 1:20 $Alq_3$-copolymers were characterized. All three films were conductive, with the conductivity ranging between 4–12 S/cm and the highest conductivity for the 1:5 $Alq_3$ copolymer, as shown in Table 6. This observation suggests that the polymer system of this invention can be used as the electron-transport and emission layer in OLEDs.

TABLE 6

Resistivity measurements and calculated conductivity of the $Alq_3$-polymers.

| Polymer[a] | Resistivity (Ω) | Thickness (cm) | Conductivity (S/cm) |
|---|---|---|---|
| $Alq_3$ 15 | 46 | 0.00042 | 12 |
| $Alq_3$ 110 | 61 | 0.00039 | 9 |
| $Alq_3$ 120 | 92 | 0.00061 | 4 |

[a]Polymers are named after the functionalized ligand X and the ratio of 15:12. For example $Alq_3$ 110 is a 1:10 molar ratio of compound 15:12, wherein the ligand is $Alq_3$.

Solid-State Fluorescence Studies of $Alq_3$-Functionalized Polymers

Figure 5:
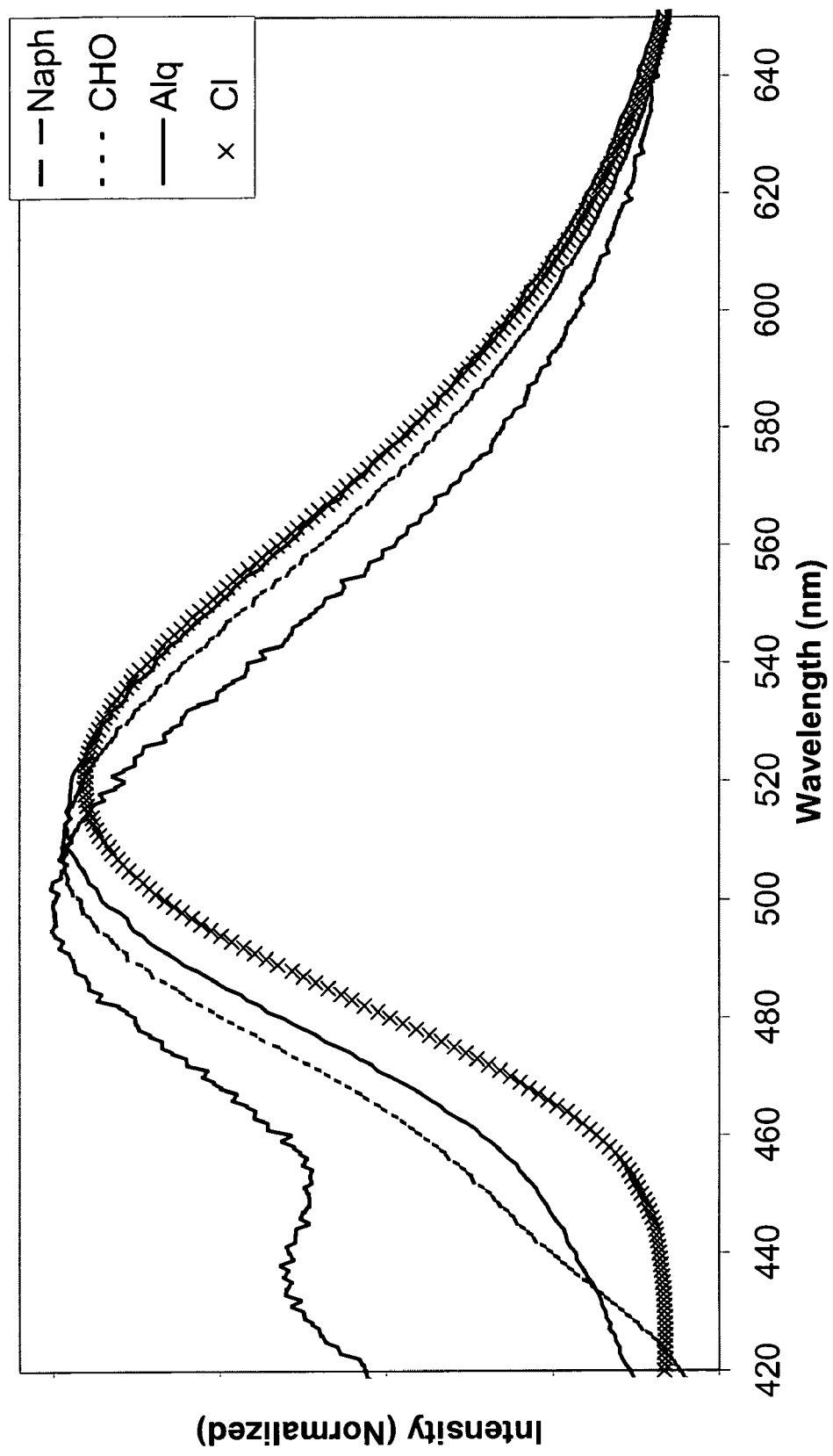
FIG. 5 provides solid-state emission spectra of selected modified polymers on quartz.

The optical properties of all $Alq_3$-functionalized polymers were also investigated in the solid-state. Unless otherwise noted, all polymers were excited at 380 nm (except for the Naph- and Quinox-polymers, which were excited at 330 nm and 400 mn, respectively) and their emission data are shown in Table 7. FIG. 5 shows the normalized fluorescence spectra of selected polymers as thin films on quartz. In the case of each functionalized polymer observed, spectra were observed to show shifts in the emission compared to the unmodified $Alq_3$-polymer. However, in all cases, the shifts were not as pronounced as the shifts observed for the same polymer in solution. Furthermore, under the conditions employed, the Nitro-, Quinox-, and Phenyl-polymers showed no emission at all. Nevertheless, the observed shifts demonstrate that tuning the emission color is possible and that the polymer backbone does not inhibit fluorescence even in the solid-state.

TABLE 7

Solution and solid-state emission wavelength for the polymers of varying chromophore ratios.

| Polymer[a] | Excitation λ (nm) | Solution Emission $\lambda_{max}$ (nm) | Solid-State Emission $\lambda_{max}$ (nm) |
|---|---|---|---|
| $Alq_3$110 | 380 | 522 | 522 |
| $Alq_3$120 | 380 | 523 | 511 |
| $Alq_3$150 | 380 | 522 | 502 |
| CHO110 | 380 | 486 | 522 |
| CHO120 | 380 | 488 | 510 |
| CHO150 | 380 | 487 | 494 |
| PVK110 | 380 | 543 | 549 |
| PVK120 | 380 | 543 | 537 |
| PVK150 | 380 | 544 | 530 |

[a]Polymers are named after the functionalized ligand X and the molar ratio of 15:12.

Figure 6:
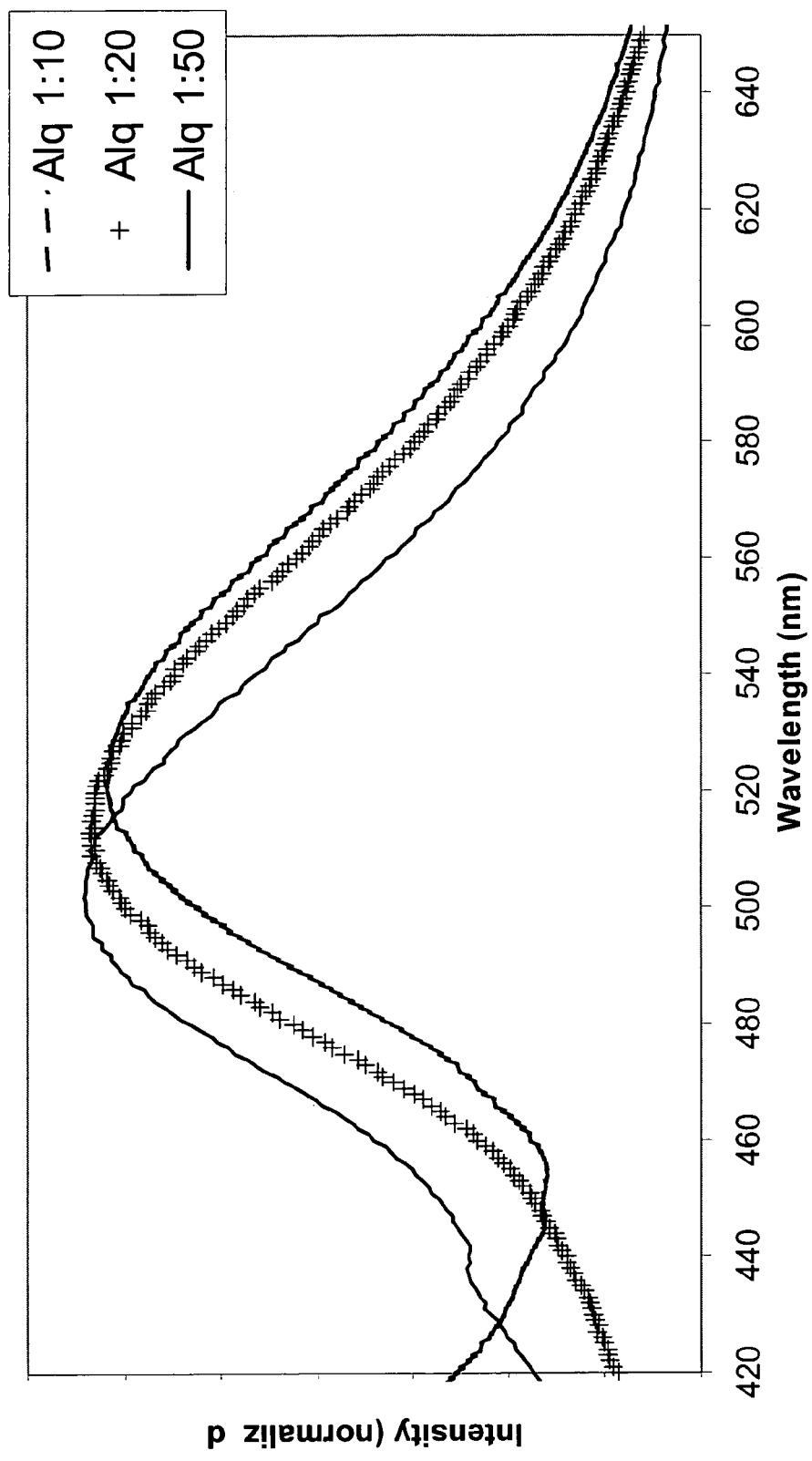
FIG. 6 provides solid-state emission spectra of three different comonomer ratios of the $Alq_3$-polymer.
Figure 7:
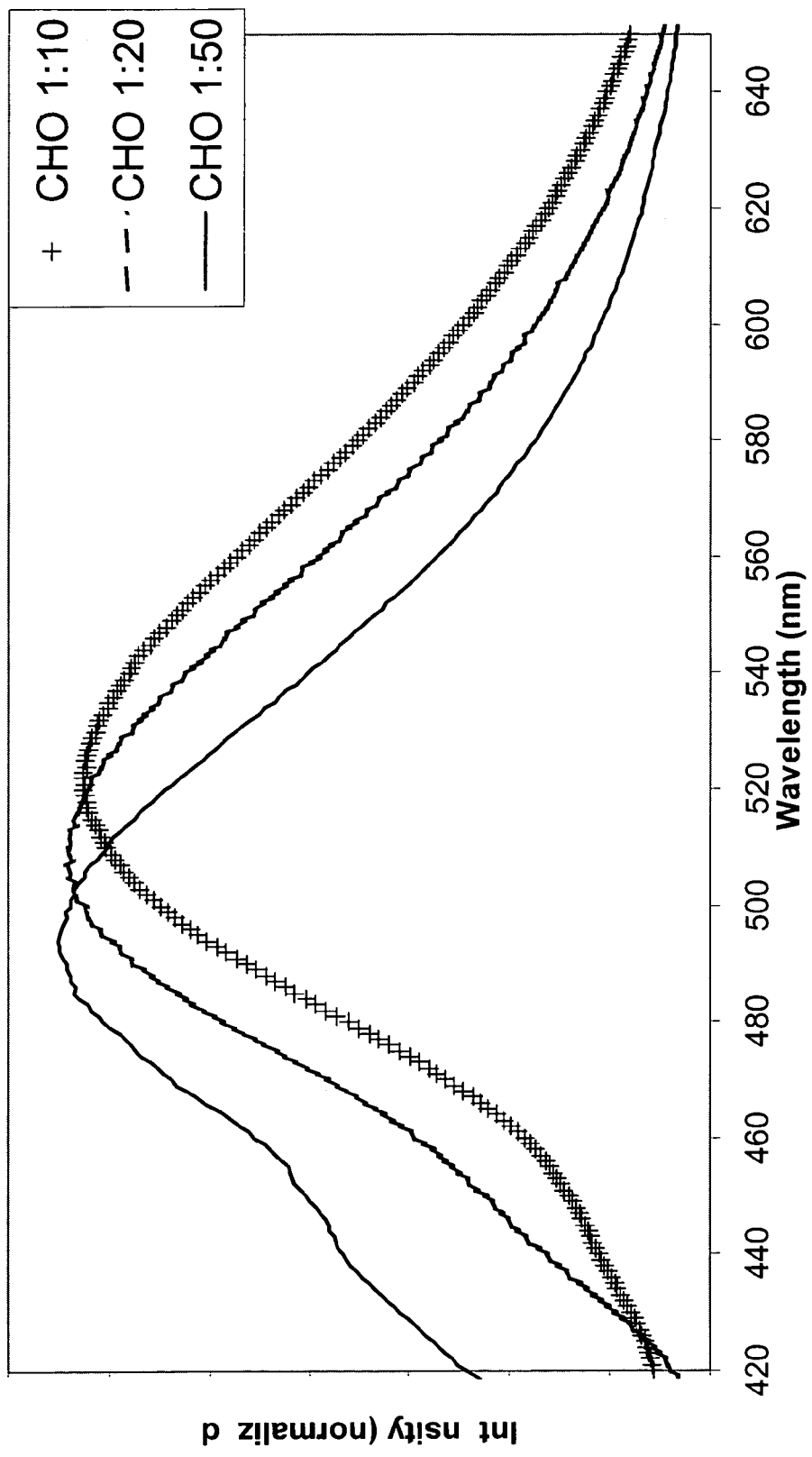
FIG. 7 provides solid-state emission spectra of three different comonomer ratios of the CHO-polymer.
Figure 8:
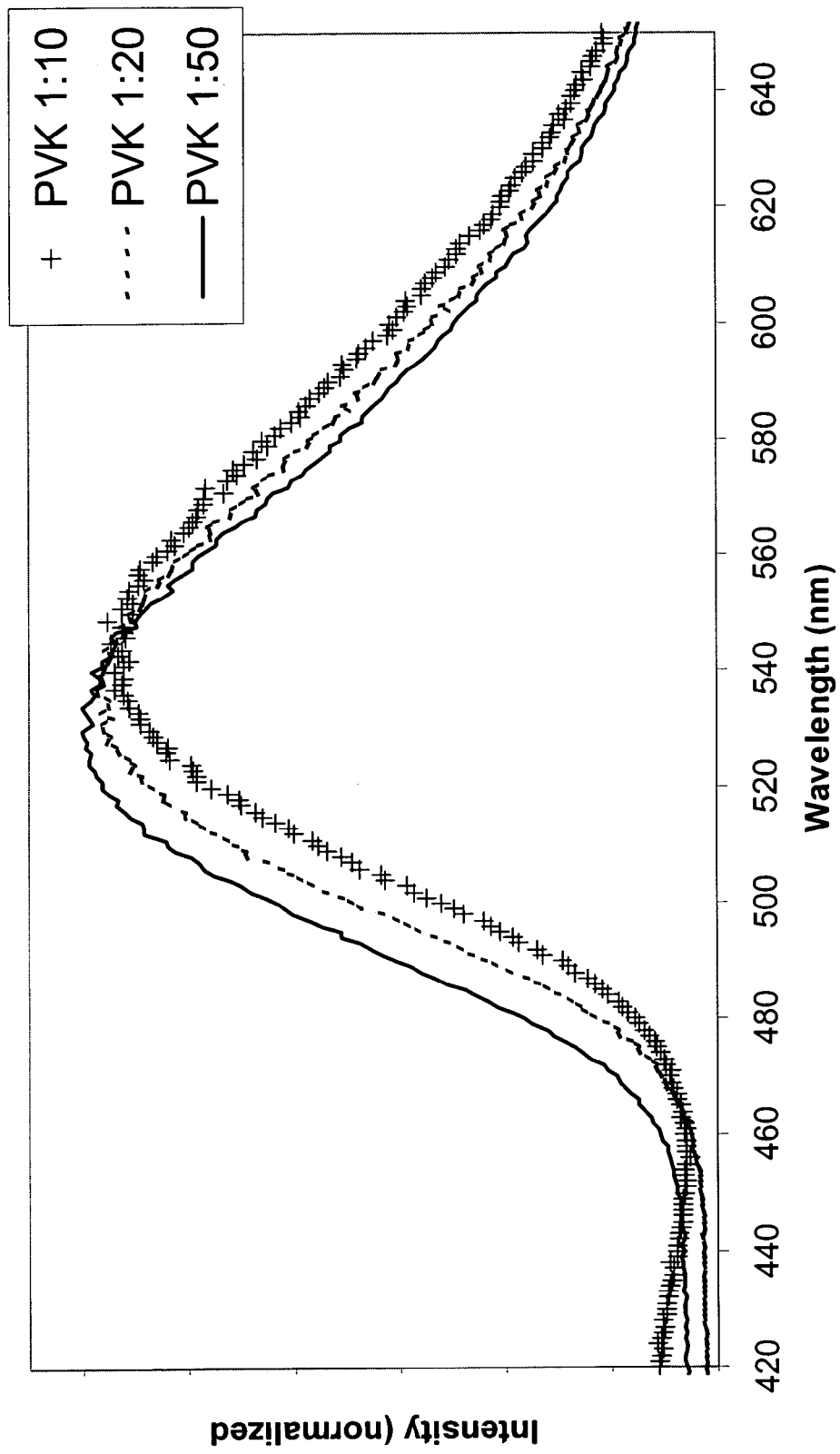
FIG. 8 provides solid-state emission spectra of 3 different comonomer ratios of the PVK-polymer.

In order to investigate the influence of chromophore density on the emission, the ratio of the $AlqX_2$-monomer and nonylnorbornene was varied. The results of this study are shown in FIGS. 6–8 and are summarized in Table 7. FIG. 6 illustrates the solid-state fluorescence spectra of the $Alq_3$-polymer with functionalized $Alq_3$-monomer (15) to nonyl-norbornene (12) ratios of 1:10, 1:20, and 1:50. The emission wavelength is observed to be blue-shifted with decreasing chromophore density. Similar results can also be seen in FIG. 7 for the CHO-polymer and FIG. 8 for the PVK-polymer. While the shifts are different for each polymer, the trend is the same in all cases. However, a 1:100 ratio of 15:12 of the CHO-polymer showed identical emission peaks as that of the 1:50 CHO-polymer, therefore, this chromophore dilution effect appeared to be limited. While not intending to be bound by theory, this observation suggested that the emission wavelength is dependant on the packing of the $AlqX_2$-complex, which is consistent with the notion that the shorter the inter-ligand contacts, the more red-shifted the emission. (See, Brinkmann, M.; Gadret, G.; Muccini, M.; Taliani, C.; Masciocchi, N.; Sirani, A. *J. Am. Chem. Soc.* 2000, 122, 5147–5157, which is incorporated by reference herein in its entirety.)

The effect of molecular weight on the optical properties was also investigated. As shown in Table 5, it was found that the changes in molecular weight have very little effect on the emission of the polymer, both in solution and the solid-state.

FIG. 9 provides examples of catalysts that can be used for polymerizing the functionalized monomers to the functionalized polymers, based on a ring-opening metathesis polymerization (ROMP) catalytic process.

Fluorescence Studies on $Znq_2$ Complexes

Figure 10:
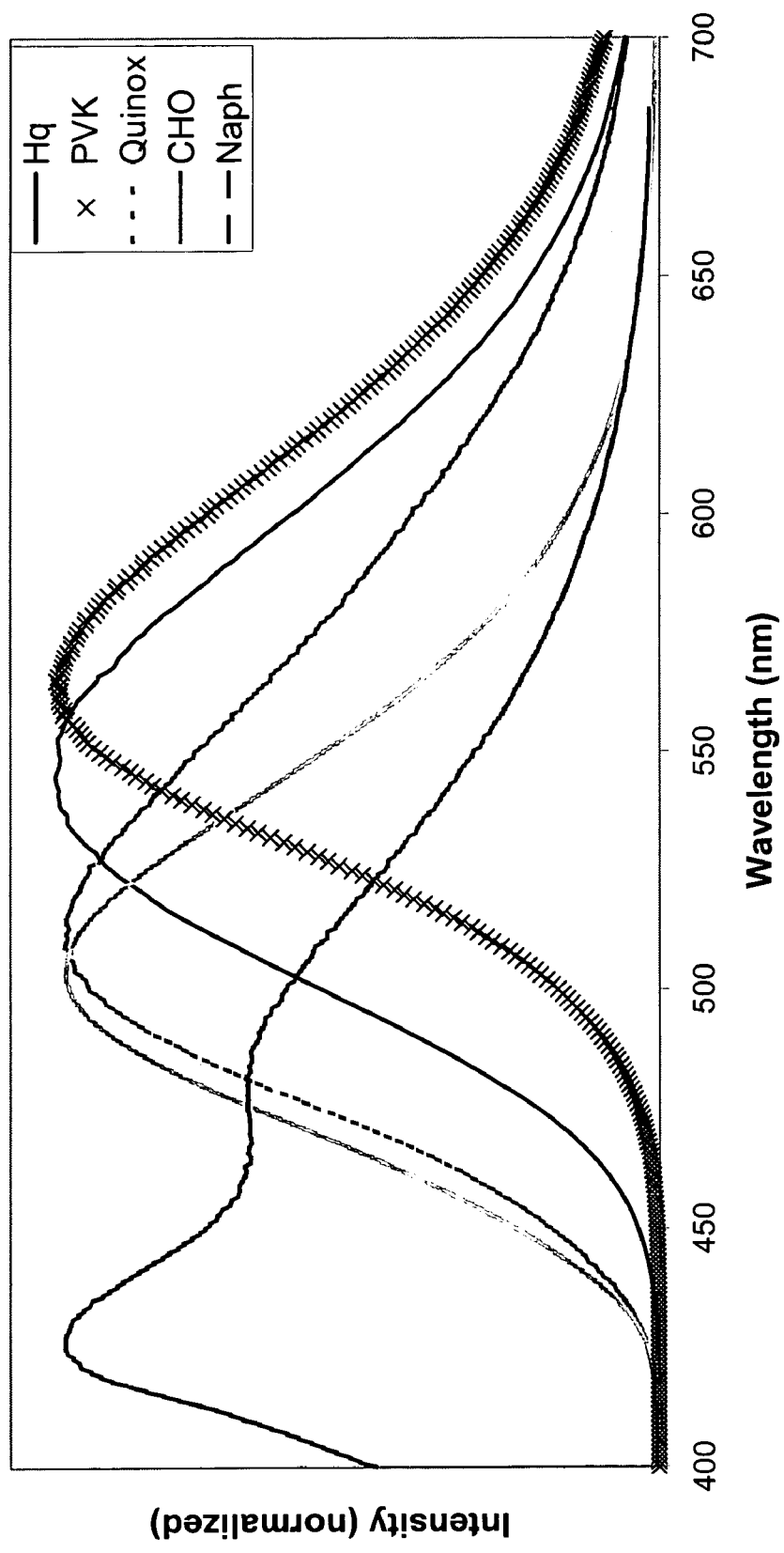
FIG. 10 illustrates the solution fluorescence spectra (normalized intensity vs. wavelength (nm)) of all $Znq_2$-functionalized copolymers, excited at 380 nm, except for the Naph copolymer which was excited at 330 nm.
Figure 11:
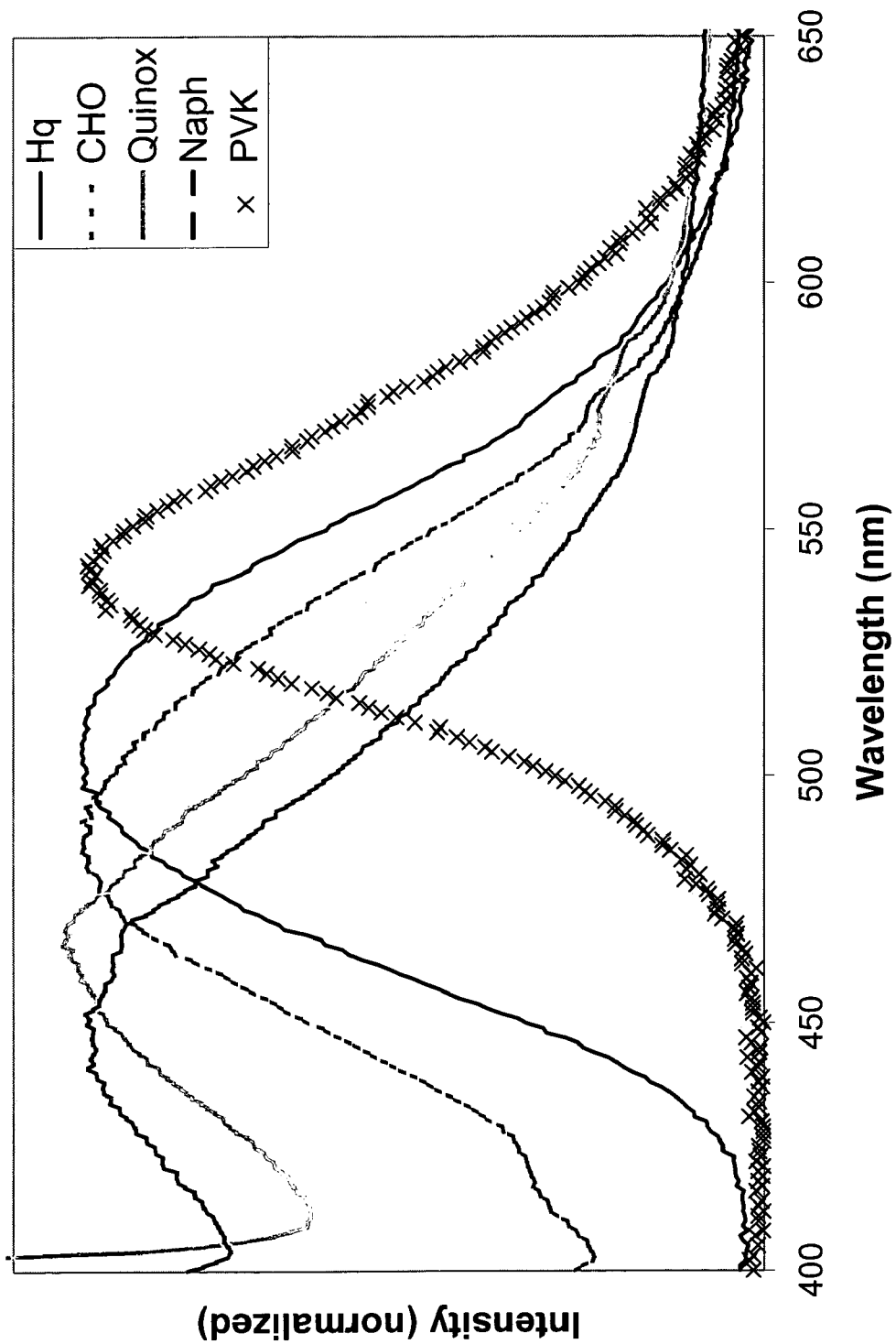
FIG. 11 demonstrates that the emission (normalized intensity vs. wavelength (nm)) of the $Znq_2$-functionalized copolymers can be tuned solid-state from blue (427 nm) to the yellow (565 nm) through modifications on the second functionalized quinoline.

All zinc-containing copolymers 18 were characterized using NMR, UV/Vis, and fluorescence spectroscopy, with the results being summarized in Table 8. The molecular weights of the copolymers ranged from about 8,000 to about 40,000, with polydispersities from about 1.5 and about 2.5 as determined by GPC. The UV/Vis and fluorescence spectra were recorded in dry chloroform. FIG. 10 illustrates the solution fluorescence spectra of all $Znq_2$-functionalized copolymers, excited at 380 nm, except for the Naph copolymer which was excited at 330 mn. FIG. 11 demonstrates that the emission of the $Znq_2$-functionalized copolymers can be tuned in solution from blue (427 nm) to the yellow (565 nm) through modifications on the second functionalized quinoline. These results further demonstrate that the fluorescence properties of the material can be tuned in solution and that the polymer backbone does not interfere with the optical properties of the $Znq_2$ moiety.

The relative quantum yields of the zinc-containing copolymers 18 were calculated based on $Alq_3$ as the standard and are summarized in Table 8. $Znq_2$-containing monomer was observed to have a higher quantum yield than $Alq_3$. The 1:1, 1:5, and 1:10 $Znq_2$-copolymers were observed to exhibit even higher quantum yields than their small molecule counterpart. It is not until the concentration of the $Znq_2$-monomer dropped below about 10 mol % of the copolymer that the quantum yields decrease below that of $Znq_2$. While not intending to be bound by theory, the increase in quantum yields going from $Znq_2$ to the 1:1 $Znq_2$-copolymer to the 1:5 $Znq_2$-copolymer indicates the possibility of some self-quenching occurring at higher $Znq_2$ concentrations.

TABLE 8

Photoluminescence and related date for $Znq_2$-containing monomers and polymers.

| Compound | Absorption $\lambda_{max}$ | Solution Emission $\lambda_{max}$ | Solid State Emission $\lambda_{max}$ | Relative Quantum Yields |
|---|---|---|---|---|
| $Alq_3$ | 381 | 525 | 519[a] | 1.0 |
| $Znq_2$ | 379 | 542 | 542[a] | 1.3 |
| 1:1 $Znq_2$ | 378 | 544 | 548 | 1.8 |
| 1:5 $Znq_2$ | 374 | 543 | 520 | 3.9 |
| 1:10 $Znq_2$ | 375 | 545 | 512 | 2.0 |

TABLE 8-continued

Photoluminescence and related date for $Znq_2$-containing monomers and polymers.

| Compound | Absorption $\lambda_{max}$ | Solution Emission $\lambda_{max}$ | Solid State Emission $\lambda_{max}$ | Relative Quantum Yields |
|---|---|---|---|---|
| 1:20 $Znq_2$ | 378 | 546 | 505 | 0.30 |
| CHO | 381 | 503 | 487 | 2.2 |
| PVK | 373 | 565 | 545 | 0.33 |
| Naph | 325 | 427 | 445 | 0.37 |
| Quinox | 379 | 510 | 467 | 0.44 |

[a]Reported in T. A. Hopkins, K. Meerholz, S. Shaheen, M. L. Anderson, A. Schmidt, B. Kippelen, A. B. Padias, J. H. K. Hall, N. Peyghambarian and N. R. Armstrong, Chem. Mater. 1996, 8, 344; which is incorporated herein by reference in its entirety.

To characterize the solid-state properties of all $Znq_2$-containing copolymers, thin films were spun on quartz slides, with thicknesses ranging between 200–400 nm as determined by ellipsometery. The fluorescence spectra were recorded at an excitation wavelength of 380 nm (Naph at 330 nm) and are shown in FIG. 11, with the $\lambda_{max}$ reported in Table 8. Similar to the solution studies, the emission colors of the films range from the blue to the yellow. The influence of the lumophore density on the solid-state properties was also investigated. The 1:1 copolymer emission, a high lumophore concentration, is red-shifted in comparison to the emission of the 1:20 copolymer. Regardless of the lumophore concentration and the quinoline ligand used, the emission of the thin films again indicated that the polymer backbone does not inhibit fluorescence, even in the solid-state. Conductivity of the films was measured using a four-point probe and resulted in conductivities ranging from 12 S/cm for the 1:1 $Znq_2$-copolymer to 3.6 S/cm for the 1:20 $Znq_2$-copolymers. The results obtained from these experiments suggested that the $Znq_2$-polymers were able to support a current, which indicates these materials are useful in electroluminescen't devices.

Definitions

In order to more clearly define the terms used herein, the following definitions are provided. To the extent that any definition or usage provided by any document incorporated herein by reference conflicts with the definition or usage provided herein, the definition or usage provided herein controls.

As used herein, the terms $Mq_n$-moiety, $Mq_n$-containing moiety, and the like refer to a chemical moiety which comprises an $Mq_n$ residue, an $Mq_n$-like residue, a functionalized $Mq_n$ residue, a functionalized $Mq_n$-like residue, or similar structures. Thus, $Mq_n$-moieties constitute that portion of the $Mq_n$-functionalized molecule, monomer, or polymer that includes the $Mq_n$ core group, regardless of the functionalization of the 8-hydroxyquinoline ligands and regardless of the heteroatom substitutions within the 8-hydroxyquinoline ligands.

The term 8-hydroxyquinoline residue is used to refer to, among other things, an 8-hydroxyquinoline ligand that can be non-functionalized; functionalized with at least one electron-donating group, at least one electron-withdrawing group, or a combination thereof; can be deprotonated; can be partially hydrogenated; and the like; or any combination of these. In the usual sense, the 8-hydroxyquinoline residue of this invention comprises a deprotonated 8-hydroxyquinoline, therefore $Mq_n$-containing monomers and polymers refer to metal (M) complexes in the $n^+$ oxidation state. This term is also used to refer to 8-hydroxyquinoline-like ligands such as, for example, ligands in which either another heteroatom is present in one of the 6-membered rings of the 8-hydroxyquinoline ligand, or a partially hydrogenated 8-hydroxyquinoline-like ligand. Examples of this type 8-hydroxyquinoline residue include, but are not limited to, the Naph and Quinox (also termed Quix) ligands illustrated in FIG. 3. This term also refers to 8-hydroxyquinoline ligands, or their heteroatom substituted analogs, that can be functionalized with at least one group independently selected from: a hydrocarbyl group, an oxygen group, a sulfur group, a nitrogen group, a phosphorus group, an arsenic group, a carbon group, a silicon group, a germanium group, a tin group, a lead group, a boron group, an aluminum group, an inorganic group, an organometallic group, or a substituted analog thereof, any one of which having from 1 to about 30 carbon atoms; a halide; hydrogen; or any combination thereof.

The terms polymerizable moiety, polymerizable unit, polymerizable residue, and the like refer to a chemical moiety containing a polymerizable functional group. Examples of polymerizable functional groups include, but are not limited to, alkenes, alkynes, butadienes, and the like, although viable polymerizable functional groups depending upon factors that include, but are not limited to, the polymerization method, polymerization catalyst, monomer containing that polymerizable functional group, and the like. Examples of polymerizable moieties, units, residues, and the like, include, but are not limited to norborene, norbornadiene, cyclopentene, cyclooctene, cyclooctadiene, or functionalized analogs thereof.

EXAMPLES

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to one of ordinary skill in the art without departing from the spirit of the present invention or the scope of the appended claims.

Example 1

General Synthetic and Characterization Details

Unless otherwise specified, all chemicals were purchased from Acros Organics or Aldrich and used without further purification. All reactions were performed in atmospheric conditions unless otherwise noted. Flash column chromatography was carried out on silica gel 60, 230–400 mesh (Whatman or Sorbent Tech). The $^1H$ ($^{13}C$) NMR spectra were recorded at 300 (75) MHz on a Varian Mercury 300 spectrometer. Chemical shifts are reported in ppm on the δ scale relative to the solvent residual proton signal. Mass spectra were obtained on a Micromass Quattro LC spectrometer or a VG-70se spectrometer. Elemental analyses were performed on a Perkin-Elmer CFINS/O Analyzer Series II 2400.

Differential scanning calorimetry (DSC) was performed under nitrogen using either a Perkin-Elmer DSC 7 equipped with an Intracooler II device, wherein the temperature program provided heating and cooling cycles between 0° C. and 300° C. at 20° C./min, or provided heating and cooling cycles between −30° C. and 150° C. at 10° C./min. Differential scanning calorimetry (DSC) was also performed under nitrogen using a Netzsch STA 409 PG DSC coupled with a Netzsch TG 209 thermal gravimetric analyzer, wherein the temperature program provided a heating rate of 20° C./min from room temperature up to 800° C. Thermogravimetric analysis (TGA) measurements were also performed using Netzsch TG 209 from 30 to 800° C. at 20° C./min.

For some samples, gel permeation chromatography (GPC) analyses were carried out using a Waters 1525 binary pump coupled to a Waters 2414 refractive index detector. The GPC was calibrated using polystyrene standards on a Styragel® HR 4 and HR 5E column set with $CH_2Cl_2$ as an eluent. For other samples, gel permeation chromatography (GPC) analyses were carried out using a Waters 1525 binary pump coupled to a Waters 410 refractive index detector. The GPC was calibrated using polystyrene standards on an American Polymer Standards 10µ particle size, linear mixed bed packing columns set with $CH_2Cl_2$ as an eluent.

The UV/Visible spectra were obtained on a Perkin-Elmer Lambda 19 UV/VIS/NIR Spectrometer. The fluorescence spectra were obtained on a Spex Fluorolog Spectrofluorometer. Ellipsometry measurements were taken on a J. A. Woollam Co. Inc. Spectroscopic Ellipsometer, M-2000VI.

Compounds 1–3 and 6 were synthesized from the following literature procedures: Clemo, G. R.; Howe, R. *J. Chem. Soc.* 1955, 3552–3553; Giraudi, G.; Baggiani, C.; Giovannoli, C.; Marletto, C.; Vanni, A. *Anal. Chim. Acta* 1999, 378, 225–233; and Stubbs, L. P.; Weck, M. *Chem. Eur. J* 2003, 9, 992–999; each of which is incorporated herein by reference in its entirety.

The modified 8-hydroxyquinoline ligands abbreviated as Naph, Quinox, Ph, CHO, and PVK were prepared from literature procedures, as described in: Meyers, A.; Weck, M. *Macromolecules* 2003, 36, 1766–1768; Freeman, S. K.; Spoerri, P. E. *J. Org. Chem.* 1951, 16, 438–442; Eck, T. D.; Wehry Jr., E. L.; Hercules, D. M. *J. Inorg. Nucl. Chem.* 1966, 28, 2439–2441; Hojjatie, M.; Muralidhara, S.; Dietz, M. L.; Freiser, H. *Synth. Comm.* 1989, 19, 2273–2282; and Clemo, G. R.; Howe, R. *J. Chem. Soc.* 1955, 3552–3553; each of which is incorporated herein by reference in its entirety. The remaining modified 8-hydroxyquinoline ligands used in this invention were commercially available.

Example 2

Preparation of 6-Bicyclo[2.2.1]hept-5-en-2-yl-hexylamine (4)

A solution of the nitrile 3 (1.052 g, 0.005 mol) in diethyl ether was added dropwise to a $LiAlH_4$ suspension (0.43 g, 0.011 mol in 40 mL diethyl ether) at 0° C. The mixture was allowed to warm to room temperature over a period of an hour, refluxed for 30 minutes, and then cooled back to room temperature. Water was added to neutralize any excess $LiAlH_4$. The ether layer was washed with water, 20% NaOH, brine, and dried over $Na_2SO_4$. The ether was removed to give a pale yellow liquid, which needed no further purification (0.726 g 67%). $^1H$ NMR (300 MHz, $CDCl_3$) δ6.07 (1H endo, dd, J=2.74, 5.49); 6.03–5.97 (2H exo, m); 5.87 (1H endo, J=2.74, 5.49); 2.70 (2H, s); 2.65 (2H, t, J=7.14); 1.94–1.74 (2H, m); 1.43–0.99 (12H, m); 0.46–0.40 (1H, m). $^{13}C$ NMR (75 MHz, $CDCl_3$) δ13 132.6; 49.8; 45.6; 42.7; 38.9; 34.9; 33.9; 32.6; 29.9; 28.8; 27.1. HRMS (EI): calcd for $C_{13}H_{23}N_1$ $[M]^+$ 193.1832, found 193.1852.

Example 3

Preparation of 5-[(6-Bicyclo[2.2.1]hept-5-en-2-yl-hexylimino)-methyl]-quinolin-8-ol (7)

Amine 4 (0.726 g, 0.00376 mol) and 5-formyl-8-hydroxyquinoline 6 (0.650 g, 0.00376 mol) were dissolved in 40 mL of benzene and refluxed for 18 hours. After cooling, the solvent was removed under reduced pressure to yield the product as an orange solid (1.308 g, 100%). $^1H$ NMR (300 MHz, $CDCl_3$) δ9.75 (1H, dd J=8.79, 1.64); 8.81 (1H, dd, J=1.64, 4.39); 8.59 (1H, s); 7.69 (1H, d, J=8.24); 7.56 (1H, dd, J=4.39, 8.79); 7.19 (1H, d, J=7.69); 6.10 (1H endo, dd, J=2.74, 5.49); 6.06–5.99 (2H exo, m); 5.91 (1H endo, dd, J=2.74, 5.94); 3.67 (2H, t, J=7.14); 2.74 (2H, s); 1.99–1.69 (4H, m); 1.42–1.01 (12H, m); 0.50–0.44 (1H, m). $^{13}C$ NMR (75 MHz, $CDCl_3$) δ160.8; 154.2; 148.1; 138.4; 137.0; 135.3; 133.0; 132.6; 127.0; 123.3; 123.2; 109.2; 62.9; 49.7; 45.6; 42.7; 38.9; 34.9; 32.6; 31.4; 29.9; 28.8; 27.6. HRMS (EI): calcd for $C_{23}H_{28}N_2O_1$ $[M]^+$ 348.2201, found 348.2186.

Example 4

Preparation of 5-[(6-Bicyclo[2.2.1]hept-5-en-2-yl-hexylamino)-methyl]-quinolin-8-ol (8)

Imine 7 was dissolved in 50 mL of dry methanol and 1 equivalent of $NaBH_4$ (0.136 g, 0.0036 mol) was added in small increments. After the addition was complete, the solution was allowed to stir for 10 minutes at room temperature. The solution was diluted with water and extracted three times with 20 mL of methylene chloride. The combined organic layers were washed with water, $NaHCO_3$, brine, and dried over $Na_2SO_4$. The solvent was removed under reduced pressure to yield a brown liquid. Purification by column chromatography (silica gel, 4:1 hexanes/ethyl acetate, then pure ethyl acetate, then 5% methanol in ethyl acetate) gave the product as a pale yellow solid (0.658 g, 50%). $^1H$ NMR (300 MHz, $CDCl_3$) δ8.75 (1H, dd, J=1.09, 4.39); 8.51 (1H, dd, J=1.09, 8.24); 7.46 (1H, dd, J=4.39, 8.24); 7.38 (1H, d, J=7.69); 7.08 (1H, d, J=7.69); 6.11 (1H endo, dd, J=2.74, 5.49); 6.06–5.99 (2H exo, m); 5.90 (1H endo, dd, J=2.74, 5.49); 4.10 (1H, s); 2.73 (2H, s); 2.71 (2H, t, J=7.14); 1.99–1.02 (12H, m); 0.49–0.43 (1H, m). $^{13}C$ NMR (75 MHz, $CDCl_3$) δ151.8; 147.6; 137.0; 136.3; 133.4; 132.6; 128.0; 127.4; 126.8; 121.8; 109.2; 51.2; 50.0; 49.7; 45.5; 42.7; 38.9; 34.9; 32.6; 30.2; 29.9; 28.8; 27.5. Anal. Calcd for $C_{23}H_{30}N_2O$: C, 78.88; H, 8.63; N, 8.00. Found C: 78.79, H: 8.72, N: 8.00.

Example 5

Preparation of the $Alq_3$-functionalized monomer 9

The formation of the $Alq_3$-functionalized monomer 9 was achieved by adding monomer 8, dissolved in 10 mL of dry THF, dropwise to ten equivalents of triethylaluminum, dissolved in 10 mL of dry THF, and stirring under argon for 2 hours. Then 20 equivalents of 8-hydroxyquinoline, dissolved in 10 mL THF was added dropwise to the monomer solution, and the solution was stirred overnight under argon. Any precipitate that formed was filtered off and the solvent was removed to yield a bright yellow solid. This product was used without further purification in the polymerization procedure.

Example 6

Preparation of 5-Nonyl-bicyclo[2.2.1]hept-2-ene (12)

An oven-dried 3-neck round bottom flask was charged with magnesium turnings (0.809 g, 0.033 mol) and 40 mL of dry THF. 5-Bromomethyl norbornene (6.001 g, 0.032 mol) was added dropwise at room temperature. The mixture was then heated to 50° C. for 18 hours. In a separate flask, 10 mL of dry THF, $Li_2CuCl_4$ (5 mL, 0.0005 mol), and 1-bromooctane (6 mL, 0.035 mol) were combined and placed in a −10° C. ice bath. The Grignard reagent, which was transferred via cannula into an addition funnel, was added dropwise to the cooled solution. After the addition was complete, the solution was warmed to room temperature and stirred for 18 hours. The solution was diluted with ether, washed with $NH_4Cl$, brine, and dried over $Na_2SO_4$. The solvent was removed and the product was distilled at 76° C. at 0.4 mbar to yield a clear, colorless liquid (4.88 g, 69%). $^1H$ NMR (300 MHz, $CDCl_3$) δ6.12 (1H endo, dd, J=2.74, 5.49); 6.09–5.99 (2H exo, m); 5.93 (1H endo, dd, J=2.74, 5.49); 2.75 (1H, s); 1.98–1.78 (2H, m); 1.40–1.07 (18H, m); 0.89 (3H, t, J=6.05); 0.52–0.45 (1H, m). $^{13}C$ NMR (75 MHz, $CDCl_3$) δ137.0; 132.6; 49.7; 45.6; 42.7; 38.9; 35.0; 32.6; 32.1; 30.1; 29.9; 29.8; 29.5; 28.9; 22.9; 14.3.

Example 7

Preparation of 5-[6-Bicyclo[2.2.1]hept-5-en-2-yl-hexylamino)-methyl]-8-quinolinato-(dihydroxy)-aluminum (14).

The monomer 5-[(6-Bicyclo[2.2.1]hept-5-en-2-yl-hexylamino)-methyl]-quinolin-8-ol (8) (0.025 g, 0.07 mmol) was dissolved in 5 mL benzene, and added dropwise to a solution of triethylaluminum (0.04 mL, 0.07 mmol) in 10 mL benzene, Scheme 5. The reaction was stirred for 2 hours under argon, the precipitate was filtered off, and the solvent was removed to yield a yellow solid 14 (0.03 g, 96% yield). $^1H$ NMR (300 MHz, $CDCl_3$) δ8.86 (0.5H, dd, $J_1$=4.94, 17.58); 8.68 (0.5H, m); 7.72 (1H, dd, J=3.29, 5.50); 7.54 (2H, m); 7.03 (1H, t, J=8.24); 6.11 (1H endo, dd, J=2.74, 5.49); 6.06–5.99 (2H exo, m); 5.90 (1H endo, dd, J=2.74, 5.49); 4.10 (1H, s); 2.73 (2H, s); 2.71 (2H, t, J=7.14); 1.99–(12H, m); 0.49–0.43 (1H, m). $^{13}C$ NMR (75 MHz, $CDCl_3$) δ137.0; 132.8; 51.2; 50.0; 49.7; 45.5; 42.7; 38.9; 34.9; 32.6; 30.2; 29.9; 28.8; 27.5.

Example 8

Preparation of 5-[6-Bicyclo[2.2.1]hept-5-en-2-yl-hexylamino)-methyl]-8-quinolinato-(diligand X)-aluminum (15a–15j)

Two equivalents of a modified 8-hydroxyquinoline ligand X, examples of which are shown in FIG. 3 and which are abbreviated as X in Scheme 5, were dissolved in benzene and added dropwise to one equivalent of the dihydroxy monomer 14, dissolved in 10 mL of benzene. The solution was allowed to stir under argon for two hours, followed by the removal of the solvent to yield a solid ranging in color from bright yellow to dark orange. The exceptions to this procedure are when X was 4-hydroxy-1,5-naphthyridine (Naph) or 8-hydroxyquinoline-5-sulfonic acid. ($SO_3H$) These compounds were dissolved in DMSO, while monomer 14 was dissolved in THF.

The resulting functionalized $Alq_3$-containing monomers provided by this procedure are shown in Table 1.

Example 9

General Polymerization Procedure

Monomers 9, 15 (15a–15j), and 12, as needed, were dissolved in chloroform in the desired ratio, the ruthenium catalyst 11 was dissolved in chloroform, and both solutions were combined. The polymerizations were monitored by NMR and were complete within 12 hours. All polymers were purified by repeated precipitation into methanol. Again, the exceptions to this procedure are when the functionalized monomer X was 4-hydroxy-1,5-naphthyridine or the 8-hydroxyquinoline-5-sulfonic acid. In these cases, the $AlqX_2$-monomer Naph and $SO_3H$ were dissolved in a 1:1 ratio of DMSO/chloroform.

Example 10

Solution Photoluminescence Studies

Approximately 5 mg of each of the polymers shown in Table 5 was dissolved in 10 mL of chloroform. Dilutions were made as needed. UV/Visible and fluorescence measurements were taken in a 1.0 cm quartz cell.

Example 11

Thin Film Fabrication and Characterization

The concentrations of the polymers in solution were varied from 15–100 mg of polymer per mL of chloroform. One drop of each solution was dropped onto a quartz slide spinning at 2000 rpm. The polymer solutions that showed the highest fluorescence intensity in the solid-state ranged from 30–50 mg/mL. The films made for the ellipsometry experiment were prepared in a similar manner using gold-coated glass slides (100 nm of Au) instead of quartz slides. The film thicknesses were measured by ellipsometry by collecting data every 5° from 65° to 75° and were fitted using a Cauchy film on gold model. The resistances of the films were measured using a Keithley 196 system and an Ai alessi four-point probe. The probe was lowered until it came in contact with the surface of the films and the resistance was recorded. Conductivity was determined based on the equation: $\sigma=0.221 (R*t)^{-1}$, where R is the resistance in ohms, t is the thickness of the film in centimeters, and σ is the conductivity in Siemens/cm. (See: Smits, F. M. *Bell Syst. Tech. J.* 1958, 710–718.)

Example 12

Spin-Casting Procedure

The copolymers prepared according to this invention were dissolved in chloroform at a concentration of approximately 30 mg/mL. Using a Specialty Coating Systems P-6000 spin coater, the solution was dropped onto an ITO-coated glass slide, spinning at 1200 rpm.

Example 13

Preparation of 5-[6-Bicyclo[2.2.1]hept-5-en-2-yl-hexylamino)-methyl]-8-quinolinato-(Zigand X)-zinc (2).

Monomer 8 (0.025 g, 0.07 mmol) was dissolved in 5 mL dry benzene and added dropwise to a solution of diethylzinc (0.04 mL, 0.07 mmol) in 10 mL dry benzene. The reaction was stirred for two hours under argon. The resulting precipitate was filtered off and the solvent was removed to yield a yellow solid which was used without further purification (0.03 g, 96% yield). One equivalent of the modified 8-hydroxyquinoline ligands X was dissolved in 10 mL dry benzene and added dropwise to one equivalent of the zinc-monomer, dissolved in 10 mL of dry benzene. The solution was allowed to stir under argon for two hours, followed by the removal of the solvent to yield a solid ranging in color from bright yellow to dark orange.

Example 14

Thin Film Fabrication and Characterization of $Znq_2$-Copolymers

The concentrations of the $Znq_2$-containing polymers in solution were varied from 15–100 mg of polymer per mL of dry chloroform. One drop of each solution was dropped onto a quartz slide spinning at 2000 rpm. The polymer solutions that showed the highest fluorescence intensity in the solid-state ranged from 30–50 mg/mL. The films made for the ellipsometry experiment were prepared in a similar manner using gold-coated glass slides (100 nm of Au) instead of quartz slides. The film thicknesses were measured by ellipsometry by collecting data every 5° from 65° to 75° and were fitted using a Cauchy film on gold model. The resistances of the films were measured using a Keithley 196 system and an Ai alessi four-point probe. The probe was lowered until it came in contact with the surface of the films and the resistance was recorded. Conductivity was determined based on the equation: $\sigma = 0.221\ (R*t)^{-1}$, where R is the resistance in ohms, t is the thickness of the film in centimeters, and $\sigma$ is the conductivity in Siemens/cm².

What is claimed is:

1. An $Alq_3$-functionalized compound comprising an olefinic, acetylenic, or diolefinic polymerizable moiety and an $Alq_3$-moiety, wherein q, in each instance, comprises an 8-hydroxyquinoline residue.

2. The $Alq_3$-functionalized compound of claim 1, wherein the $Alq_3$-moiety is functionalized with at least one electron-donating group, at least one electron-withdrawing group, or a combination thereof.

3. The $Alq_3$-functionalized compound of claim 1, wherein the $Alq_3$-moiety is functionalized with at least one group independently selected from: a hydrocarbyl group, an oxygen group, a sulfur group, a nitrogen group, a phosphorus group, an arsenic group, a carbon group, a silicon group, a germanium group, a tin group, a lead group, a boron group, an aluminum group, an inorganic group, an organometallic group, or a substituted analog thereof, any one of which having from 1 to about 30 carbon atoms; a halide; hydrogen; or any combination thereof.

4. The $Alq_3$-functionalized compound of claim 1, wherein the compound has the formula

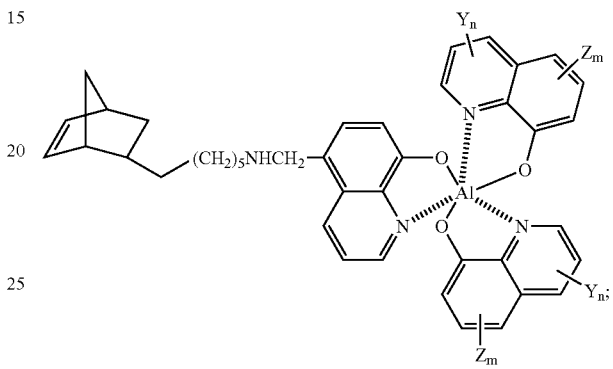

wherein Y and Z are independently selected from —F, —Cl, —Br, —I, —R¹, —CR¹=O, —CH=CHC(O)R¹, —C(O)R¹, —C(O)OR¹, —CN, —C(NR¹)R¹, —C(NR¹)OR¹, —CH₂C₆H₄X, —CH₂C₆H₃X₂, —CH₂C₆H₄R¹, —CH₂C₆H₃R¹₂, —CH₂CH₂C₆H₄X, —CH₂CH₂C₆H₃X₂, CH₂CH₂C₆H₄R¹, —CH₂CH₂C₆H₃R¹₂, —CH=CR¹₂, —OR¹, —SiR¹₃, —OSiR¹₃, NO₂, —NR¹₂, —N₃, —N=NR¹₂, —N=NR¹, —SR¹, —SX, —OSO₂R¹, —OSO₂R¹, —SCN, —SO₂R¹, —PR¹₂, —PX₂, —P(O)R¹₂, —P(OR¹)₂, —P(O)(OR¹)₂, —OSiR¹₃, —OPR¹₂, —OAlR¹₂, —AsR¹₂, —As(O)R¹₂, —As(OR¹)₂, —As(O)(OR¹)₂, SnR¹₃, OSnR¹₃, SnX¹₃, OSnX¹₃, —BR¹₂, —BX₂, —BR¹X, —SO₂X, —OAlX₂, —OSiX₃, —OPX₂, —OSO₂X, —AsX₂, or —As(O)X₂;

wherein R¹, in each instance, is independently selected from H or a substituted or unsubstituted hydrocarbyl group having from 1 to about 30 carbon atoms;

wherein X, in each instance, is independently selected from F, Cl, Br, I, H, OR¹, —SR¹, or NR¹₂; and wherein n and m are independently selected from an integer from 0 to 3.

5. The $Alq_3$-functionalized compound of claim 1, wherein the compound is selected from:

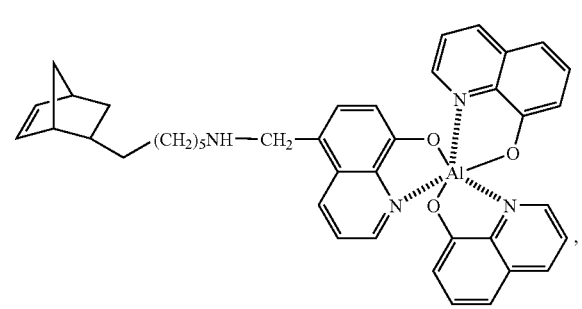

-continued
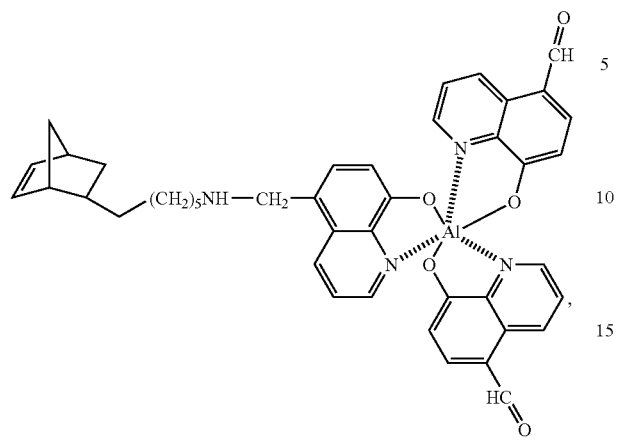
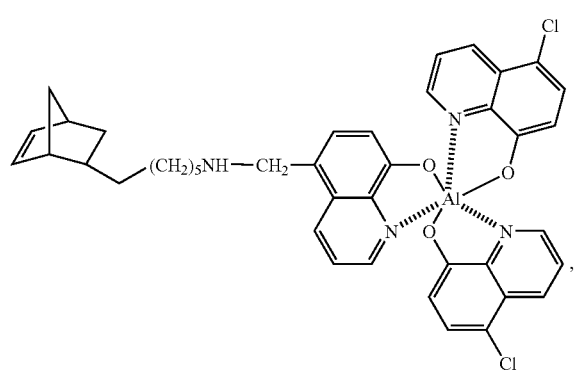
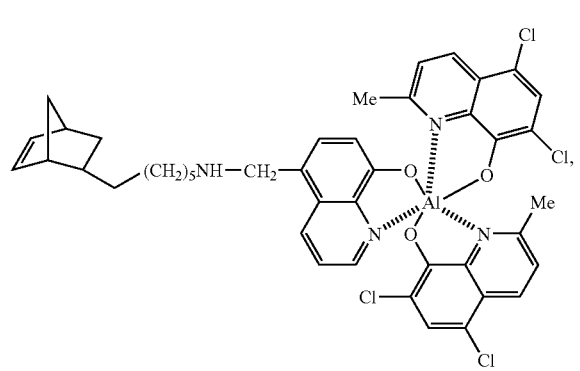
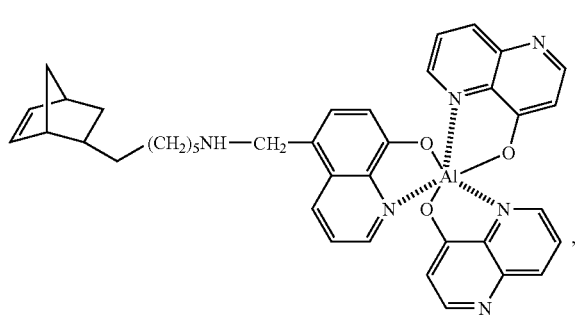
-continued
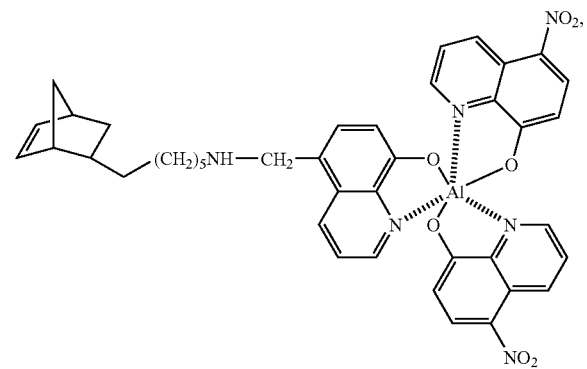
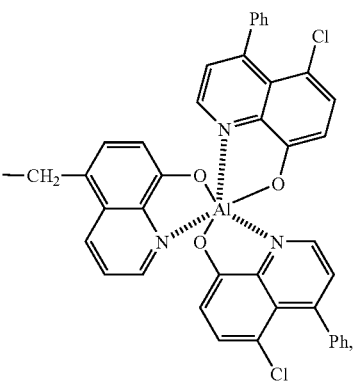
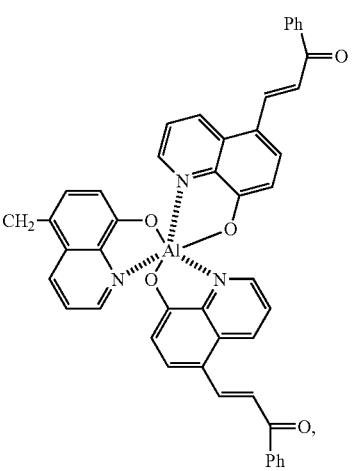
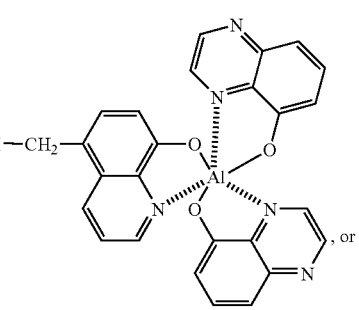

-continued

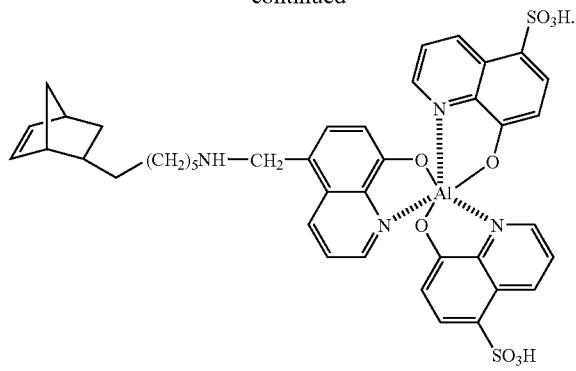

6. A light-emitting diode comprising the polymerization product of the $Alq_3$-functionalized compound of claim 1.

7. A composition comprising the polymerization product of an $Alq_3$-functionalized monomer, wherein the $Alq_3$-functionalized monomer comprises an olefinic, acetylenic, or diolefinic polymerizable moiety and an $Alq_3$-moiety, and wherein q, in each instance, comprises an 8-hydroxyquinoline residue.

8. The composition of claim 7, wherein the polymerization product is substantially non-crosslinked.

9. The composition of claim 7, wherein the $Alq_3$-moiety is functionalized with at least one electron-donating group, at least one electron-withdrawing group, or a combination thereof.

10. The composition of claim 7, wherein the polymerizable moiety is norbornene.

11. A light-emitting diode comprising the composition of claim 7.

12. A composition comprising the polymerization product of at least one $Alq_3$-functionalized monomer and at least one comonomer, wherein the $Alq_3$-functionalized monomer comprises an olefinic, acetylenic, or diolefinic polymerizable moiety and an $Alq_3$-moiety, and wherein q, in each instance, comprises an 8-hydroxyquinoline residue.

13. The composition of claim 12, wherein the polymerizable moiety is norbornene, norbornadiene, cyclopentene, cyclooctene, cyclooctadiene, or a substituted analog thereof.

14. The composition of claim 12, wherein the polymerizable moiety is norbornene or a substituted analog thereof.

15. The composition of claim 12, wherein the $Alq_3$-moiety is functionalized with at least one electron-donating group, at least one electron-withdrawing group, or a combination thereof.

16. The composition of claim 12, wherein the $Alq_3$-moiety is functionalized with at least one group independently selected from: a hydrocarbyl group, an oxygen group, a sulfur group, a nitrogen group, a phosphorus group, an arsenic group, a carbon group, a silicon group, a germanium group, a tin group, a lead group, a boron group, an aluminum group, an inorganic group, an organometallic group, or a substituted analog thereof, any one of which having from 1 to about 30 carbon atoms; a halide; hydrogen; or any combination thereof.

17. The composition of claim 12, wherein the $Alq_3$-moiety is functionalized with at least one group independently selected from —F, —Cl, —Br, —I, —$R^1$, —$CR^1$=O, —CH=CHC(O)$R^1$, —C(O)$R^1$, —C(O)O$R^1$, —CN, —C(N$R^1$)$R^1$, —C(N$R^1$)O$R^1$, —$CH_2C_6H_4X$, —$CH_2C_6H_3X_2$, —$CH_2C_6H_4R^1$, —$CH_2C_6H_3R^1_2$, —$CH_2CH_2C_6H_4X$, —$CH_2CH_2C_6H_3X_2$, $CH_2CH_2C_6H_4R^1$, —$CH_2CH_2C_6H_3R^1_2$, —CH=$CR^1_2$, —C≡$CR^1$, —O$R^1$, —OC(O)$R^1$, —Si$R^1_3$, —OSi$R^1_3$, $NO_2$, —$NR^1_2$, —$N_3$, —N=$CR^1_2$, —N=$NR^1$, —$SR^1$, —SX, —$OSO_2R^1$, —$OSO_2OR^1$, —SCN, —$SO_2R^1$, —$PR^1_2$, —$PX_2$, —P(O)$R^1_2$, —P(O$R^1$)$_2$, —P(O)(O$R^1$)$_2$, —OSi$R^1_3$, —OP$R^1_2$, —OAl$R^1_2$, —As$R^1_2$, —As(O)$R^1_2$, —As(O$R^1$)$_2$, —As(O)(O$R^1$)$_2$, Sn$R^1_3$, OSn$R^1_3$, Sn$X^1_3$, OSn$X^1_3$, —$BR^1_2$, —$BX_2$, —$BR^1X$, —$SO_2X$, —$OAlX_2$, —$OSiX_3$, —$OPX_2$, —$OSO_2X$, —$AsX_2$, or —As(O)$X_2$; wherein $R^1$, in each instance, is independently selected from H or a substituted or unsubstituted hydrocarbyl group having from 1 to about 30 carbon atoms; and wherein X, in each instance, is independently selected from F, Cl, Br, I, H, $OR^1$, —$SR^1$, or $NR^1_2$.

18. The composition of claim 12, wherein the $Alq_3$-moiety is functionalized by at least one group independently selected from alkyl, cycloalkyl, alkenyl, alkynyl, aryl, aralkyl, formyl, acyl, imide, amide, imine, alkoxide, aryloxide, alkylthiolate, arylthiolate, alkoxyalkyl, haloalkyl, carboxylate, or a substituted analog thereof, any one of which having up to about 30 carbon atoms.

19. The composition of claim 12, wherein the $Alq_3$-moiety is functionalized by at least one group independently selected from methyl, ethyl, propyl, cyclopropyl, n-butyl, tert-butyl, sec-butyl, isobutyl, cyclobutyl, amyl, isoamyl, pentyl, cyclopentyl, hexyl, cyclohexyl, cycloheptyl, heptyl, octyl, cyclooctyl, nonyl, decyl, dodecyl, 2-ethylhexyl, pentenyl, butenyl, benzyl, phenyl, tolyl, naphthyl, anthracenyl, F, Cl, Br, I, OMe, OEt, O-n-Pr, O-i-Pr, O-n-Bu, O-t-Bu, O-s-Bu, OPh, $OC_6H_4Me$, $OC_6H_3Me_2$, $NMe_2$, $NEt_2$, $NPh_2$, NHMe, NHEt, NHPh, —CH=O, —CH=CHC(O)Ph, or a substituted analog thereof, any one of which having up to about 30 carbon atoms.

20. The composition of claim 12, wherein the $Alq_3$-functionalized monomer further comprises a chemical spacer between the polymerizable moiety and the $Alq_3$-moiety, having between 1 and about 30 carbon atoms.

21. The composition of claim 20, wherein the chemical spacer is selected from —$(CH_2)_2NHCH_2$— or —$(CH_2)_n NR^1CH_2$—, wherein n is from 1 to about 12, and $R^1$ is selected from a hydrocarbyl or substituted hydrocarbyl having from 1 to about 30 carbon atoms.

22. The composition of claim 12, wherein the polymerization product comprises a block copolymer or a random copolymer.

23. The composition of claim 12, wherein the $Alq_3$-functionalized monomer is selected from:

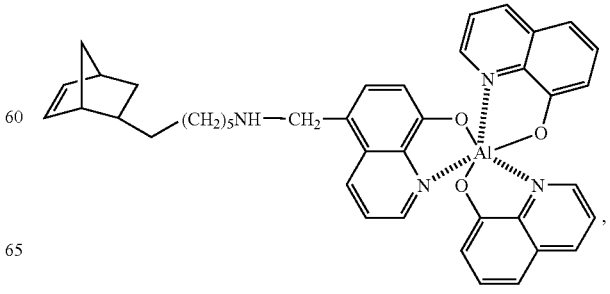

-continued
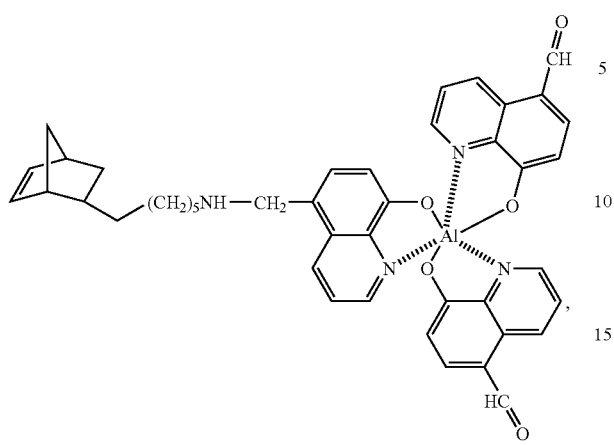
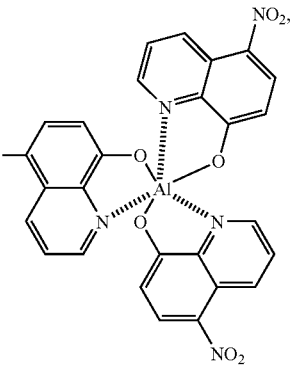
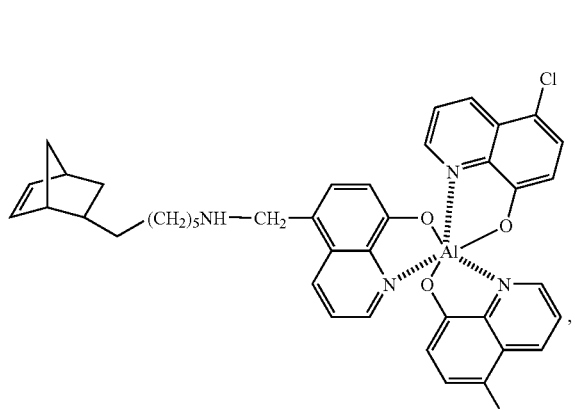
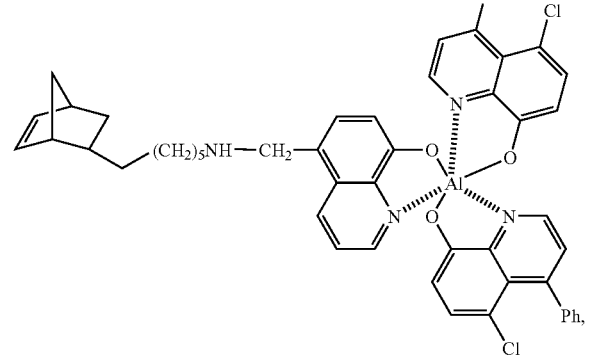
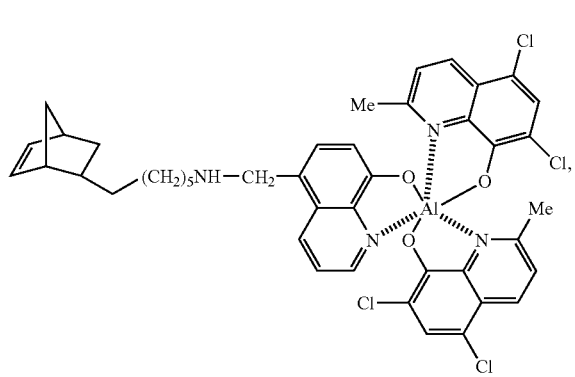
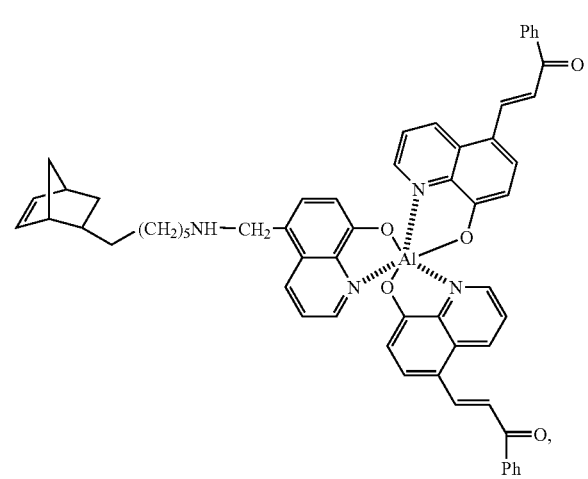
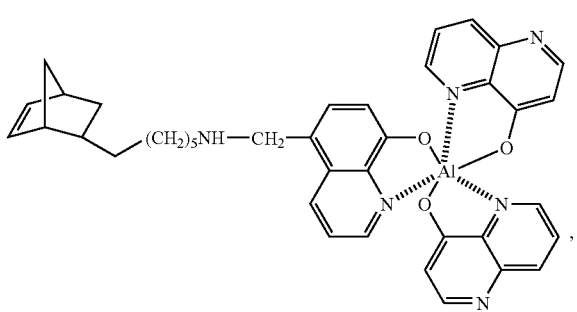
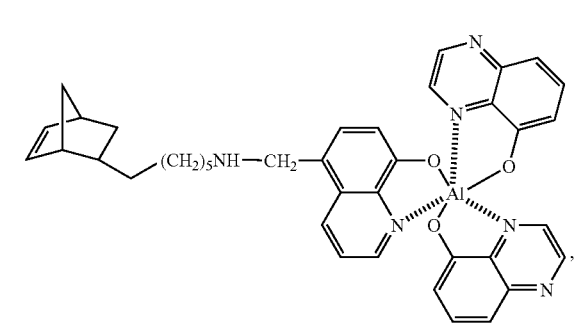

-continued

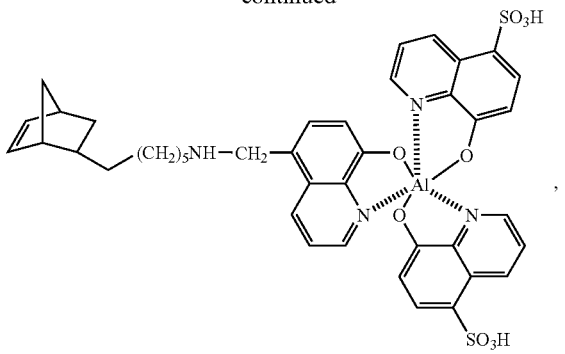

or any combination thereof.

24. The composition of claim 12, wherein the at least one comonomer comprises a compound with the formula

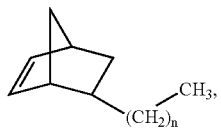

wherein n is an integer from 1 to about 12.

25. The composition of claim 12, wherein the polymerization product is characterized by a polydispersity (Mw/Mn) from about 1.5 to about 1.8.

26. A light-emitting diode comprising the composition of claim 12.

27. A method of making an $Alq_3$-functionalized polymer, comprising:
polymerizing an $Alq_3$-functionalized monomer in the presence or absence of at least one comonomer;
wherein the $Alq_3$-functionalized monomer comprises an olefinic, acetylenic, or diolefinic polymerizable moiety and an $Alq_3$-moiety; and
wherein q, in each instance, comprises an 8-hydroxyquinoline residue.

28. The method of claim 27, wherein the $Alq_3$-functionalized monomer is polymerized in the presence of at least one comonomer.

29. The method of claim 27, wherein the $Alq_3$-functionalized monomer is polymerized in the presence of at least one comonomer, and wherein the molar ratio of $Alq_3$-functionalized monomer to comonomer is from about 1:1 to about 1:100.

30. The method of claim 27, wherein the $Alq_3$-functionalized monomer is polymerized in the presence of at least one comonomer comprising

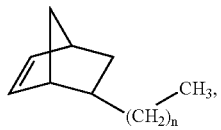

wherein n is an integer from 1 to about 12.

31. The method of claim 27, wherein the polymerizable moiety of the $Alq_3$-functionalized monomer is selected from norbornene, norbornadiene, cyclopentene, cyclooctene, cyclooctadiene, or a functionalized analog thereof.

32. The method of claim 27, wherein the method comprises a ring-opening metathesis polymerization (ROMP) method.

33. The method of claim 27, wherein the method comprises a radical polymerization method or a living radical polymerization method.

34. The method of claim 27, wherein the polymerization is conducted in the presence of a catalyst comprising a transition metal carbene compound.

35. The method of claim 27, wherein the polymerization is conducted in the presence of a catalyst comprising $Ru(CHPh)Cl_2[CHN_2(mesityl)_2C_2H_4](PCy_3)$.

36. The method of claim 27, wherein the $Alq_3$-moiety is functionalized with at least one group independently selected from: a hydrocarbyl group, an oxygen group, a sulfur group, a nitrogen group, a phosphorus group, an arsenic group, a carbon group, a silicon group, a germanium group, a tin group, a lead group, a boron group, an aluminum group, an inorganic group, an organometallic group, or a substituted analog thereof, any one of which having from 1 to about 30 carbon atoms; a halide; hydrogen; or any combination thereof.

37. The method of claim 27, wherein the $Alq_3$-moiety is functionalized with at least one group independently selected from —F, —Cl, —Br, —I, —$R^1$, —$CR^1$=O, —CH=CHC(O)$R^1$, —C(O)$R^1$, —C(O)O$R^1$, —CN, —C(N$R^1$)$R^1$, —C(N$R^1$)O$R^1$, —$CH_2C_6H_4X$, —$CH_2C_6H_3X_2$, —$CH_2C_6H_4R^1$, —$CH_2C_6H_3R^1_2$, —$CH_2CH_2C_6H_4X$, —$CH_2CH_2C_6H_3X_2$, —$CH_2CH_2C_6H_4R^1$, —$CH_2CH_2C_6H_3R^1_2$, —CH=$CR^1_2$, —C≡$CR^1$, —O$R^1$, —OC(O)$R^1$, —$SiR^1_3$, —$OSiR^1_2$, —$NO_2$, —$NR^1_2$, —$N_3$, —N=$CR^1_2$, —N=$NR^1$, —$SR^1$, —SX, —$OSO_2R^1$, —$OSO_2OR^1$, —SCN, —$SO_2R^1$, —$PR^1_2$, —$PX_2$, —P(O)$R^1_2$, —P(O$R^1$)$_2$, —P(O)(O$R^1$)$_2$, —$OSiR^1_3$, —$OPR^1_2$, —$OAlR^1_2$, —$AsR^1_2$, —As(O)$R^1_2$, —As(O$R^1$)$_2$, —As(O)(O$R^1$)$_2$, $SnR^1_3$, $OSnR^1_3$, $SnX^1_3$, $OSnX^1_3$, —$BR^1_2$, —$BX_2$, —$BR^1X$, —$SO_2X$, —$OAlX_2$, —$OSiX_3$, —$OPX_2$, —$OSO_2X$, —$AsX_2$, or —As(O)$X_2$; wherein $R^1$, in each instance, is independently selected from H or a substituted or unsubstituted hydrocarbyl group having from 1 to about 30 carbon atoms; and wherein X, in each instance, is independently selected from F, Cl, Br, I, H, $OR_1$, —$SR_1$, or $NR^1_2$.

38. The method of claim 27, wherein the $Alq_3$-moiety is functionalized by at least one group independently selected from alkyl, cycloalkyl, alkenyl, alkynyl, aryl, aralkyl, formyl, acyl, imide, amide, imine, alkoxide, aryloxide, alkylthiolate, arylthiolate, alkoxyalkyl, haloalkyl, carboxylate, or a substituted analog thereof, any one of which having up to about 30 carbon atoms.

39. The method of claim 27, wherein the $Alq_3$-moiety is functionalized by at least one group independently selected from methyl, ethyl, propyl, cyclopropyl, n-butyl, tert-butyl, sec-butyl, isobutyl, cyclobutyl, amyl, isoamyl, pentyl, cyclopentyl, hexyl, cyclohexyl, cycloheptyl, heptyl, octyl, cyclooctyl, nonyl, decyl, dodecyl, 2-ethylhexyl, pentenyl, butenyl, benzyl, phenyl, tolyl, naphthyl, anthracenyl, F, Cl, Br, I, OMe, OEt, O-n-Pr, O-i-Pr, O-n-Bu, O-t-Bu, O-s-Bu, OPh, $OC_6H_4Me$, $OC_6H_3Me_2$, $NMe_2$, $NEt_2$, $NPh_2$, NHMe, NHEt, NHPh, —CH=O, —CH=CHC(O)Ph, or a substituted analog thereof, any one of which having up to about 30 carbon atoms.

40. The method of claim 27, wherein the $Alq_3$-functionalized monomer further comprises a chemical spacer between the polymerizable moiety and the $Alq_3$-moiety, having between 1 and about 30 carbon atoms.

41. The method of claim 40, wherein the chemical spacer is selected from —(CH$_2$)$_n$NHCH$_2$— or —(CH$_2$)$_2$NR$^1$CH$_2$—, wherein n is from 1 to about 12, and R$^1$ is selected from a hydrocarbyl or substituted hydrocarbyl having from 1 to about 30 carbon atoms.

42. The method of claim 27, wherein the polymerization product comprises a block copolymer.

43. The method of claim 27, wherein the Alq$_3$-functionalized monomer is selected from:

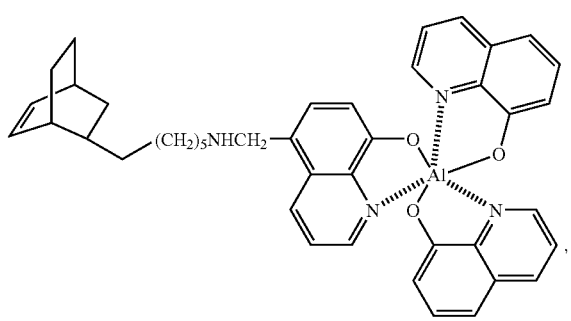

,

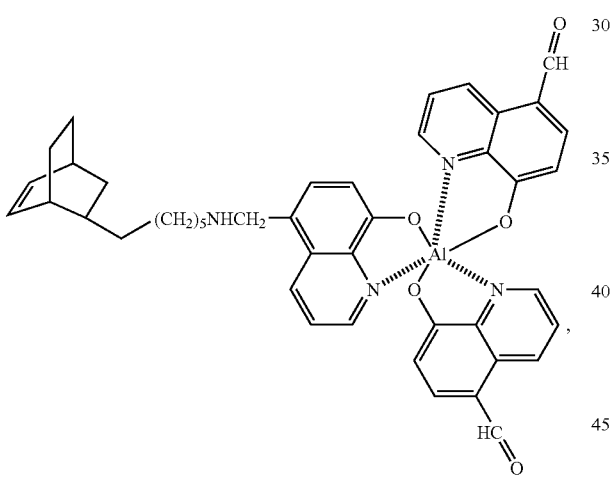

,

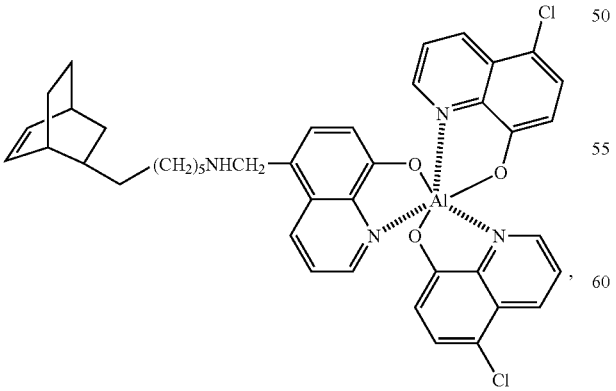

,

-continued

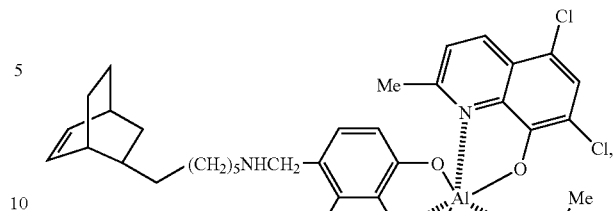

,

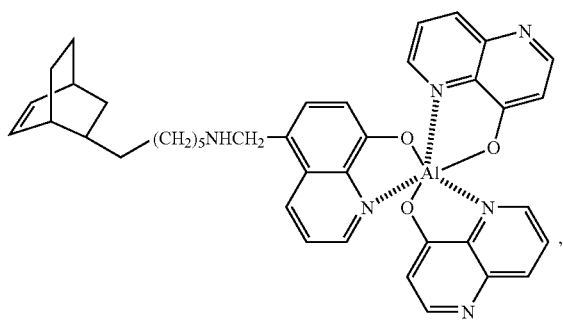

,

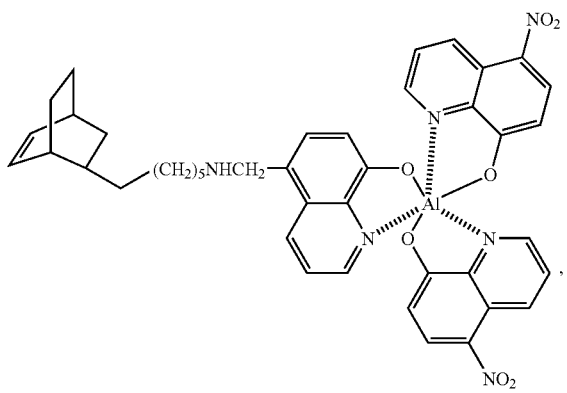

,

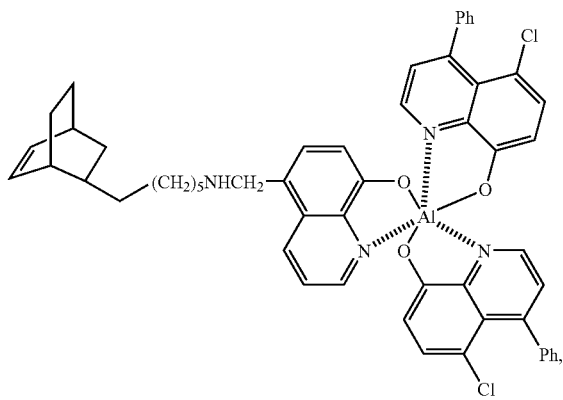

,

-continued

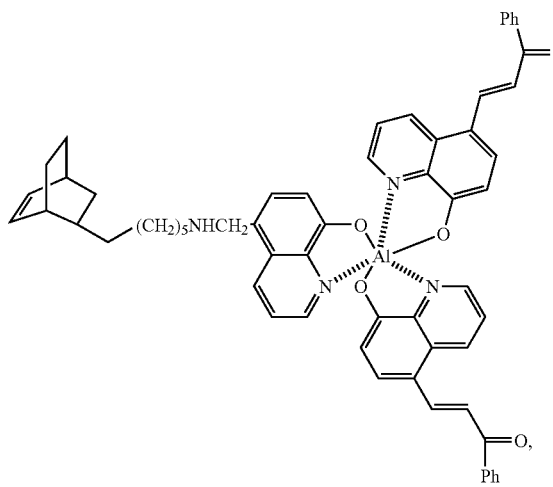

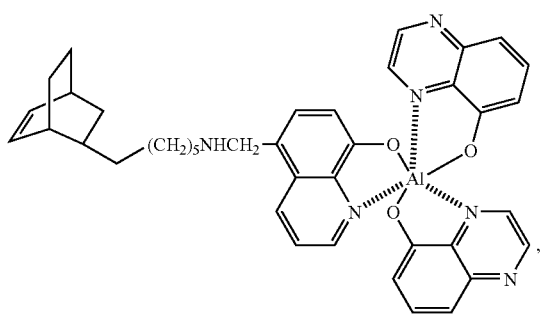

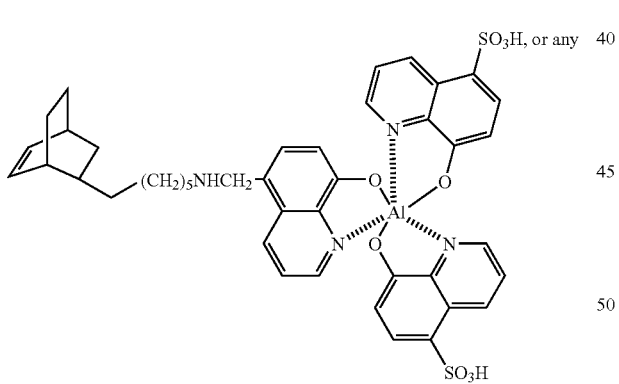

combination thereof.

44. A method of functionalizing a polymer with an Alq₃ moiety, comprising:
providing an Alq₃-functionalized monomer; and
polymerizing an Alq₃-functionalized monomer in the presence or absence of at least one comonomer;
wherein the Alq₃-functionalized monomer comprises an olefinic, acetylenic, or diolefinic polymerizable moiety and an Alq₃-moiety; and wherein q, in each instance, comprises an 8-hydroxyquinoline residue.

45. A compound having the formula

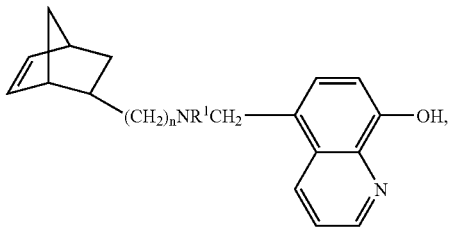

wherein: n is from 1 to about 12; and $R^1$ is selected from H, a hydrocarbyl, or a substituted hydrocarbyl having from 1 to about 30 carbon atoms.

46. A composition comprising the polymerization product of:
1) a compound having the formula

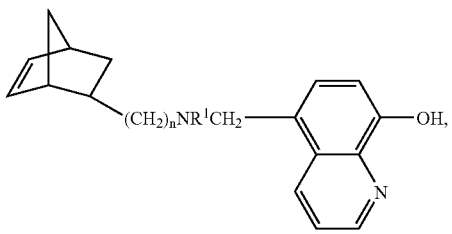

wherein: n is from 1 to about 12; and $R^1$ is selected from H, a hydrocarbyl, or a substituted hydrocarbyl having from 1 to about 30 carbon atoms; and
2) at least one optional comonomer having up to about 30 carbon atoms.

47. The composition of claim 46, wherein the at least one comonomer comprises a compound with the formula

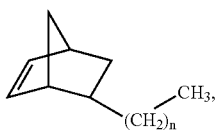

wherein n is an integer from 1 to about 12.

48. An $Mq_n$-functionalized compound comprising an olefinic, acetylenic, or diolefinic polymerizable moiety and an $Mq_n$-moiety, wherein q, in each instance, comprises an 8-hydroxyquinoline residue, and M is selected from Mg, Zn, Al, Ga, or In; and n is selected from 2 or 3 according to the valence of the metal.

49. The $Mq_n$-functionalized compound of claim 48, wherein the $Mq_n$-moiety is functionalized with at least one electron-donating group, at least one electron-withdrawing group, or a combination thereof.

50. The $Mq_n$-functionalized compound of claim 48, wherein the $Mq_n$-moiety is functionalized with at least one group independently selected from: a hydrocarbyl group, an oxygen group, a sulfur group, a nitrogen group, a phosphorus group, an arsenic group, a carbon group, a silicon group, a germanium group, a tin group, a lead group, a boron group, an aluminum group, an inorganic group, an organometallic group, or a substituted analog thereof, any one of which having from 1 to about 30 carbon atoms; a halide; hydrogen; or any combination thereof.

51. The $Mq_n$-functionalized compound of claim 48, wherein the compound has the formula

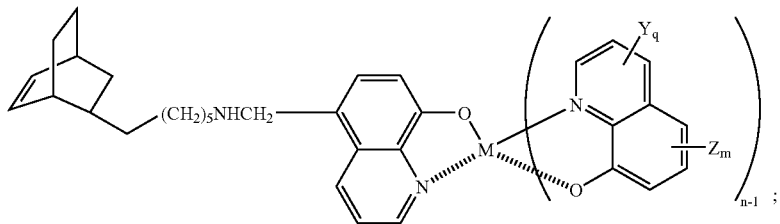

wherein Y and Z are independently selected from —F, —Cl, —Br, —I, —R¹, —CR¹=O, —CH=CHC(O)R¹, —C(O)R¹, —C(O)OR¹, —CN, —C(NR¹)R¹, —C(NR¹)OR¹, —CH₂C₆H₄X, —CH₂C₆H₃X₂, —CH₂C₆H₄R¹, —CH₂C₆H₃R¹₂, —CH₂CH₂C₆H₄X, —CH₂CH₂C₆H₃X₂, CH₂CH₂C₆H₄R¹, —CH₂CH₂C₆H₃R¹₂, —CH=CR¹₂, —C≡CR¹, —OR¹, —OC(O)R¹, —SiR¹₃, —OSiR¹₂, —NO₂, —NR¹₂, —N₃, —N=CR¹₂, —N=NR¹, —SR¹, —SX, —OSO₂R¹, —OSO₂OR¹, —SCN, —SO₂R¹, —PR¹₂, —PX₂, —P(O)R¹₂, —P(OR¹)₂, —P(O)(OR¹)₂, —OSiR¹₃, —OPR¹₂, —OAlR¹₂, —AsR¹₂, —As(O)R¹₂, —As(OR¹)₂, —As(O)(OR¹)₂, SnR¹₃, OSnR¹₃, SnX¹₃, OSnX¹₃, —BR¹₂, —BX₂, —BR¹X, —SO₂X, —OAlX₂, —OSiX₃, —OPX₂, —OSO₂X, —AsX₂, or —As(O)X₂;

wherein R¹, in each instance, is idependently selected from H or a substituted or unsubstituted hydrocarbyl group having from 1 to about 30 carbon atoms;

wherein X, in each instance, is independently selected from F, Cl, Br, I, H, OR¹, —SR¹, or NR¹₂; and wherein q and m are independently selected from an integer from 0 to 3.

52. The Mq$_n$-functionalized compound of claim 48, wherein:

the compound has the formula

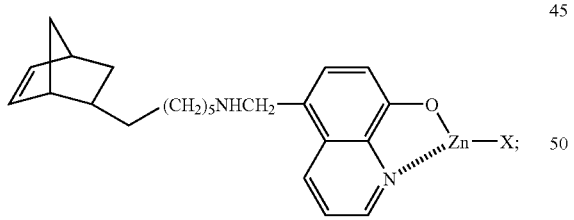

X is selected from an 8-hydroxyquinoline residue selected

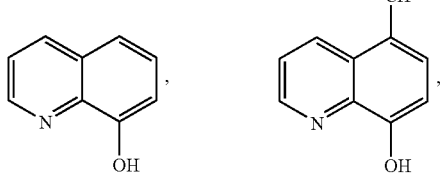

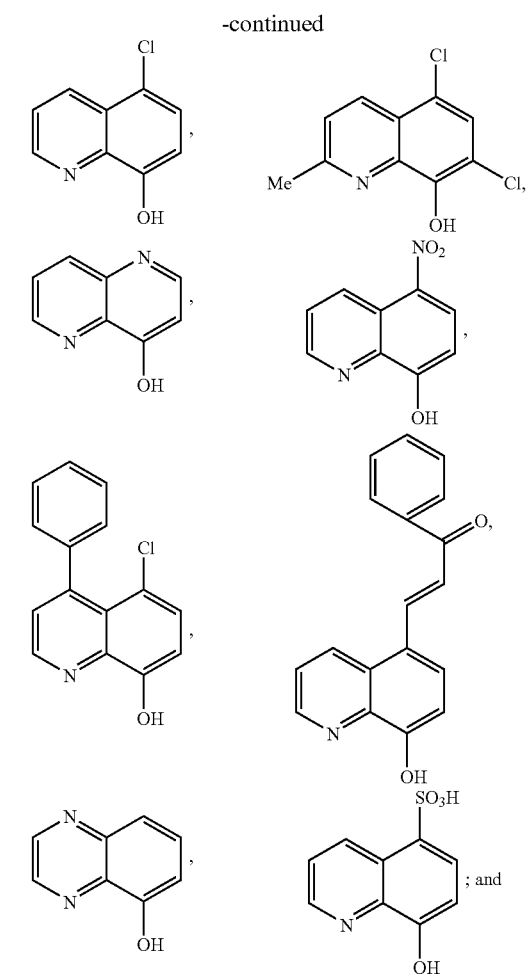

and wherein the 8-hydroxyquinoline residue has been deprotonated.

53. A method of making a Mq$_n$-functionalized polymer, comprising:

preparing a q$_n$-functionalized monomer;

polymerizing the monomer in the presence or absence of a comonomer to form a q$_n$-functionalized polymer; and reacting the polymer with a metal complex to form a Mq$_n$-functionalized polymer;

wherein M is selected from Mg, Zn, Al, Ga, or In; and n is selected from 2 or 3 according to the valence of the metal.

* * * * *